(12) United States Patent
Yoshida et al.

(10) Patent No.: US 11,981,682 B2
(45) Date of Patent: May 14, 2024

(54) SUBSTITUTED CYCLOPENTA[c]PYRROLES AS ABHD6 ANTAGONISTS

(71) Applicant: ONO PHARMACEUTICAL CO., LTD., Osaka (JP)

(72) Inventors: Atsushi Yoshida, Osaka (JP); Ryuichi Hyakutake, Osaka (JP); Nozomu Nagashima, Osaka (JP); Ryosuke Misu, Osaka (JP); Shohei Mori, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 18/472,970

(22) Filed: Sep. 22, 2023

(65) Prior Publication Data
US 2024/0010658 A1 Jan. 11, 2024

Related U.S. Application Data

(63) Continuation of application No. PCT/JP2022/016679, filed on Mar. 31, 2022.

(30) Foreign Application Priority Data

Apr. 1, 2021 (JP) ................. 2021-062790

(51) Int. Cl.
| | | |
|---|---|---|
| *A61K 31/403* | (2006.01) | |
| *A61P 29/00* | (2006.01) | |
| *C07D 209/52* | (2006.01) | |
| *C07D 405/14* | (2006.01) | |
| *C07D 409/14* | (2006.01) | |
| *C07D 417/14* | (2006.01) | |
| *C07D 487/04* | (2006.01) | |
| *C07D 495/04* | (2006.01) | |
| *C07D 495/14* | (2006.01) | |
| *C07D 513/04* | (2006.01) | |

(52) U.S. Cl.
CPC ............ *C07D 495/14* (2013.01); *A61P 29/00* (2018.01); *C07D 405/14* (2013.01); *C07D 409/14* (2013.01); *C07D 417/14* (2013.01); *C07D 487/04* (2013.01); *C07D 495/04* (2013.01); *C07D 513/04* (2013.01)

(58) Field of Classification Search
CPC ............................. A61K 31/403; C07D 209/52
USPC .......................................... 514/412; 548/452
See application file for complete search history.

(56) References Cited

U.S. PATENT DOCUMENTS

| | | |
|---|---|---|
| 2010/0130558 A1 | 5/2010 | Stewart et al. |
| 2011/0275650 A1 | 11/2011 | Cravatt et al. |
| 2014/0163077 A1 | 6/2014 | Madiraju et al. |
| 2016/0137649 A1 | 5/2016 | Jones et al. |
| 2020/0339547 A1 | 10/2020 | Lindsley et al. |
| 2021/0188820 A1 | 6/2021 | Lindsley et al. |

FOREIGN PATENT DOCUMENTS

| | | |
|---|---|---|
| JP | 2012-508737 A | 4/2012 |
| JP | 2012-509940 A | 4/2012 |
| JP | 2014-524411 A | 9/2014 |
| JP | 2016-525092 A | 8/2016 |
| JP | 2021-500345 A | 1/2021 |
| JP | 2021-503443 A | 2/2021 |

OTHER PUBLICATIONS

International Search Report (PCT/ISA/210) dated Jun. 14, 2022 from the International Searching Authority in International Application No. PCT/JP2022/016679.
Written Opinion (PCT/ISA/237) dated Jun. 14, 2022 from the International Searching Authority in International Application No. PCT/JP2022/016679.
Deng, Hui, et al., "Therapeutic potential of targeting α/β-Hydrolase domain-containing 6 (ABHD6)", European Journal of Medicinal Chemistry, vol. 198, (2020), 112353, 15 pages. https://doi.org/10.1016/j.ejmech.2020.112353.

*Primary Examiner* — Douglas M Willis
(74) *Attorney, Agent, or Firm* — Sughrue Mion, PLLC

(57) ABSTRACT

A drug is provided, which containing, as an active ingredient, a compound having ABHD6 inhibitory activity in prevention and/or treatment of a disease associated with ABHD6. A compound of formula (I-A) or a pharmaceutically acceptable salt thereof has ABHD6 inhibitory activity and therefore is useful as a pharmaceutical ingredient having potent ABHD6 inhibitory activity in the prevention and/or treatment of a disease associated with ABHD6:

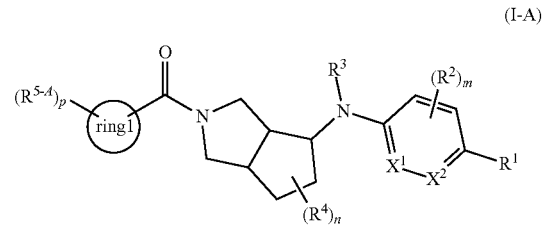

(I-A)

in which all symbols represent the same meaning as the symbols described in the specification.

4 Claims, No Drawings

SUBSTITUTED CYCLOPENTA[c]PYRROLES AS ABHD6 ANTAGONISTS

CROSS-REFERENCE TO RELATED APPLICATIONS

This is a bypass continuation of PCT International Application No. PCT/JP2022/016679 filed on Mar. 31, 2022, which claims priority to Japanese Patent Application No. 2021-062790 filed on Apr. 1, 2021, the contents of all which are incorporated herein by reference in their entirety.

FIELD

The present disclosure relates to a compound having ABHD6 inhibitory activity or a pharmaceutically acceptable salt thereof. Specifically, the present disclosure relates to a medicament containing a compound represented by general formula (I-A), or a pharmaceutically acceptable salt thereof (hereinafter, the compound is referred to as a compound of the present disclosure):

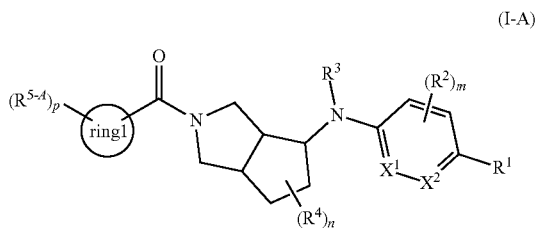

(I-A)

wherein all symbols represent the same meaning as the symbols described later.

BACKGROUND ART

ABHD6 (alpha/beta-hydrolase domain containing 6) is known as a serine hydrolase, and is one of metabolic enzymes of 2-arachidonoylglycerol (2-AG), which is an endogenous cannabinoid. 2-AG serves as a key lipid precursor of the eicosanoid signaling pathway and also functions as an endogenous signaling lipid for the activation of cannabinoid receptors 1 and 2 (CB1 and CB2, respectively). Thus, ABHD6 and 2-AG are known to be involved in the regulation of various physiological processes including pain sensation, neurotransmission, inflammation, insulin secretion, brown adipogenesis, food intake, autoimmune disorders, neurological diseases, and metabolic diseases (Non-Patent Document 1).

It is also known that inhibiting ABHD6 significantly reduces neuroinflammation and exerts neuroprotection in animal models of traumatic brain injury and multiple sclerosis. It is believed that inhibition of ABHD6 is useful for the prevention and/or treatment of various inflammatory and neurological diseases without causing central side effects by the cannabinoid system (Non-Patent Document 2).

On the other hand, Patent Document 1 states that the compound represented by the following general formula (A) is a compound having mAChR receptor antagonistic activity.

General formula (A) is as follows:

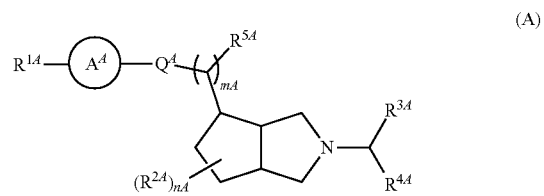

(A)

wherein ring $A^A$ represents a 5- to 6-membered heteroaryl ring having 1 to 3 heteroatoms selected from N, O, and S, $Q^A$ represents $NR^{aA}$ or O, mA represents 0, 1, or 2, $R^{1A}$ is selected from heteroaryl, aryl, heterocyclyl, cycloalkyl, halogen, $-OR^{bA}$, $-NR^{cA}R^{dA}$ and $NHCOR^{eA}$, nA represents 1 or 2, $R^{2A}$ is selected from hydrogen, a C1-4 alkyl group, halogen, and $-OR^{fA}$, $R^{3A}$ is selected from hydrogen and a C1-4 alkyl group, $R^{4A}$ is selected from $-(CR^{gA}R^{hA})_{pA}-Y^{A'}$, hydrogen, a C1-8 alkyl group, and a C1-8 alkenyl group, $R^{5A}$ is selected from hydrogen, a C1-4 alkyl group, halogen, a C1-4 haloalkyl group, a C1-4 alkoxy group, and a C1-4 haloalkoxy group, $Y^{A'}$ is selected from cycloalkyl, cycloalkenyl, heterocycle, aryl, and heteroaryl, $p^A$ represents an integer of 0 to 4, and the definition of groups was partially excerpted.

In addition, it is described that the compound represented by the following general formula (B) in Patent Document 2 is a compound having a FAAH inhibitory action.

General formula (B) is as follows:

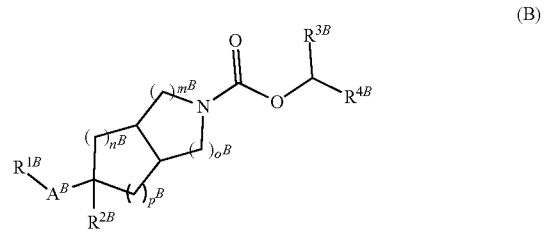

(B)

wherein $R^{2B}$ represents hydrogen, fluorine, hydroxyl, cyano, trifluoromethyl, a C1-6 alkyl group, a C1-6 alkoxy group, or a $NR^{8B}R^{9B}$ group, $m^B$, $n^B$, $o^B$ and $p^B$ each independently represent numbers ranging from 0 to 3, and each of $m^B+o^B$ and $n^B+p^B$ is 4 or less, $A^B$ represents a covalent bond, an oxygen atom, a C1-6 alkylene group, or an —O—C1-6 alkylene group (in this case, the terminal represented by the oxygen atom is bonded to the group $R^{1B}$, and the terminal represented by the alkylene group is bonded to a bicyclic carbon), $R^{1B}$ is unsubstituted or represents $R^{5B}$ which is substituted with one or more $R^{6B}$s and/or $R^{7B}$s, $R^{5B}$ represents a group selected from phenyl, pyridyl, pyridazinyl, pyrimidinyl, pyrazinyl, triazinyl, naphthyl, quinolyl, isoquinolyl, phthalazinyl, quinazolinyl, quinoxalinyl, cinnolinyl, naphthyridinyl, benzothiazolyl, benzoxazolyl, benzimidazolyl, benzisothiazolyl, benzisoxazolyl, indazolyl, and benzotriazolyl, $R^{3B}$ represents hydrogen, a fluorine atom, a C1-6 alkyl group, or a trifluoromethyl group, $R^{4B}$ represents a 5-membered heterocyclic ring selected from furyl, pyrrolyl, thienyl, thiazolyl, isothiazolyl, oxazolyl, isoxazolyl, pyrazolyl, oxadiazolyl, thiadiazolyl, imidazole, triazolyl, and tetrazolyl, and the definition of groups was partially excerpted.

In addition, it is described that the compound represented by the following general formula (C) in Patent Document 3 is a compound having a Ca channel inhibitory action.

General formula (C) is as follows:

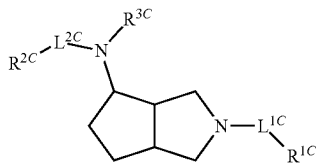

(C)

wherein $L^{1C}$ is C(O), S(O)$_2$, SO$_2$N(R$^4$), C(O)O, or —(CR$^{aC}$R$^{bC}$)$_{mC}$—, $R^{1C}$ is alkyl, G$^{1C}$, —CH(G$^{1C}$)$_2$, —(CR$^{aC}$R$^{bC}$)$_{mC}$-G$^{1C}$, —(CR$^{aC}$R$^{bC}$)$_{mC}$—CH(G$^{1C}$)$_2$, —(CR$^{eC}$R$^{fC}$)$_{nC}$—N(R$^{5C}$)$_2$, —(CR$^{eC}$R$^{fC}$)$_{nC}$—N(R$^{5C}$)—C(O)O(alkyl), —(CR$^{eC}$R$^{fC}$)$_{nC}$—N(R$^{5C}$)—C(O)(alkyl) or —(CR$^{eC}$R$^{fC}$)$_{nC}$—N(R$^{5C}$)—SO$_2$R$^{6C}$, and or $L^{1C}$-$R^{1C}$ together are hydrogen, alkyl, hydroxyalkyl, G$^{1C}$, or —CH(G$^{1C}$)$_2$, $L^{2C}$ is —(CR$^{eC}$R$^{fC}$)$_{pC}$—, C(O), C(O)N(R$^{4C}$), S(O)$_2$, SO$_2$N(R$^{5C}$), or C(O)O, $R^{2C}$ is alkyl, G$^{2C}$, —C(R$^{cC}$)(G$^{2C}$)(G$^{3C}$), —(CR$^{cC}$R$^{dC}$)$_{pC}$-G$^{2C}$, —(CR$^{cC}$R$^{dC}$)$_{pC}$—CH(G$^{2C}$)(G$^{3C}$), —(CR$^{gC}$R$^{hC}$)$_{qC}$—N(R$^{5C}$)—C(O)O(alkyl), —(CR$^{gC}$R$^{hC}$)$_{qC}$—N(R$^{5C}$)—C(O)O-G$^{2C}$, —(CR$^{gC}$R$^{hC}$)$_{qC}$—N(R$^{5C}$)—C(O)(alkyl), —(CR$^{gC}$R$^{hC}$)$_{qC}$—N(R$^{5C}$)—SO$_2$R$^{6C}$, —(CR$^{gC}$R$^{hC}$)$_{qC}$—N(R$^{4C}$)(R$^{5C}$), —(CR$^{gC}$R$^{hC}$)$_{qC}$—N(R$^{5C}$)—C(O)N(R$^{5C}$)-(alkyl) or —(CR$^{gC}$R$^{hC}$)$_{qC}$—N(R$^{5C}$)—C(O)N(R$^{5C}$)-G$^{2C}$, and or $L^{2C}$-$R^{2C}$ together are alkyl, G$^{2C}$ or —C(R$^{cC}$)(G$^{2C}$)(G$^{3C}$), $G^{1C}$, $G^{2C}$ and $G^{3C}$ are each independently aryl, cycloalkyl, cycloalkenyl, heteroaryl, or heterocyclic; $G^{1C}$, $G^{2C}$ and $G^{3C}$ are each independently unsubstituted or substituted with one, two, three, four or five substituents; and $G^{1C}$ is other than quinoline, quinazolinedione or pyridopyrimidinedione;

$R^{3C}$ represents hydrogen, alkyl, haloalkyl, cycloalkyl or cycloalkylalkyl, and the definition of groups was partially excerpted.

However, none of the prior art documents describe or suggest that the compound of the present disclosure has ABHD6 inhibitory activity.

RELATED DOCUMENTS

Patent Documents

[Patent Document 1] WO 2019/089676 A
[Patent Document 2] WO 2010/130944 A
[Patent Document 3] WO 2010/062927 A Non-Patent Documents

[Non-Patent Document 1] European Journal of Medicinal Chemistry, Vol. 198, article No. 112353, 2020

[Non-Patent Document 2] Journal of Neuroinflammation, Vol. 15, article No. 9, 2018

SUMMARY

Problems to be Solved

An object of the present invention is to provide a compound having inhibitory activity on ABHD6.

Means for Solving the Problems

As a result of intensive studies to solve the above problems, the present inventors have found that a compound represented by general formula (I-A) described later has potent inhibitory activity on ABHD6.

That is, one aspect of the present disclosure provides the following embodiments and the like:

[1] A compound represented by general formula (I-A) or a pharmaceutically acceptable salt thereof:

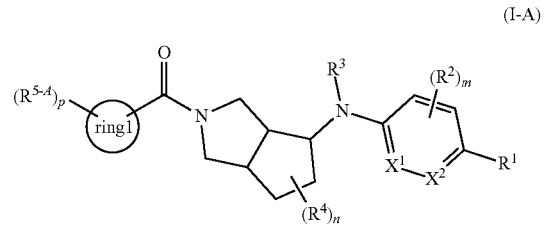

(I-A)

wherein $X^1$ and $X^2$ each independently represent (1) CH, (2) CR$^X$, or (3) N, provided that at least one of $X^1$ and $X^2$ represents N, $R^1$ represents a halogen atom, $R^X$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group, $R^2$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group, when m is 2 or more, a plurality of R$^2$s may be the same or different, $R^3$ represents (1) a hydrogen atom, (2) a C1-6 alkyl group, (3) a C1-6 haloalkyl group, (4) a 3- to 10-membered cyclic group, (5) —(C1-6 alkylene)-(3- to 10-membered cyclic group), (6) —(C1-6 haloalkylene)-(3- to 10-membered cyclic group), wherein one to two carbon atoms in the C1-6 alkyl group, the C1-6 haloalkyl group, the C1-6 alkylene, and the C1-6 haloalkylene may be replaced with an oxygen atom or an optionally oxidized sulfur atom, the 3- to 10-membered cyclic group in R$^3$ may be substituted with one to five R$^{301}$s, $R^{301}$ represents (1) a halogen atom, (2) a C1-4 alkyl group, (3) a C1-4 alkoxy group, (4) a C1-4 haloalkyl group, (5) a C1-4 haloalkoxy group, (6) COOR$^{302}$, (7) CONR$^{303}$R$^{304}$, (8) a C3-6 cycloalkyl group, (9) a hydroxyl group, (10) a nitro group, (11) a cyano group, (12) —NR$^{305}$R$^{306}$, (13) —SR$^{307}$, (14) —SOR$^{308}$, (15) —SO$_2$R$^{309}$, or (16) an oxo group, when two or more R$^{301}$s are substituted, a plurality of R$^{301}$s may be the same or different, R$^{302}$, R$^{303}$, R$^{304}$, R$^{305}$, R$^{306}$, R$^{307}$, R$^{308}$, or R$^{309}$ each independently represent (1) a hydrogen atom or (2) a C1-4 alkyl group, when R$^2$ represents (2) to (9) in R$^2$, and R$^3$ represents a C1-6 alkyl group, R$^2$ and R$^3$, together with an atom to which R$^2$ and R$^3$ are bonded, may form a 5- to 6-membered cyclic group, R$^4$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, or (9) a C1-6 haloalkoxy group, when n is 2 or more, a plurality of R$^4$s may be the same or different, when two R$^4$s present on the same carbon atom represent a C1-6 alkyl group, the two R$^4$s, together with a carbon atom to which the two R$^4$s are bonded, may form a C3-6 cycloalkyl group, ring 1 represents a 3- to 15-membered cyclic group, R$^{5\text{-}A}$ represents (1) a halogen atom, (2) a C1-6 alkyl group, (3) a C2-6 alkenyl group, (4) a C2-6 alkynyl group, (5) a C1-6 alkoxy group, (6) a C1-6 alkylthio group, (7) a C1-6 alkylsulfinyl group, (8) a C1-6 alkylsulfonyl group, (9) a C2-6 acyl group, (10) a 3- to 6-membered cyclic group, (11) -L$^{R5}$-(3- to 6-membered cyclic group), (12) a hydroxyl group, (13) a nitro group, (14) a cyano group, (15) an oxo group, (16) —NR$^{501}$R$^{502}$, (17) —COOR$^{503}$, (18) —CONR$^{504}$R$^{505}$, or (19) —SO$_2$NR$^{506}$R$^{507}$, wherein one to two carbon atoms in the C1-6 alkyl group, the C2-6 alkenyl group, the C2-6 alkynyl group, the C1-6 alkoxy group, the C1-6 alkylthio group, the C1-6 alkylsulfinyl group, the C1-6 alkylsulfonyl group, and the C2-6 acyl group may be replaced with an oxygen atom or an optionally oxidized sulfur atom, when p is 2 or more, a plurality of R$^{5\text{-}A}$s may be the same or different, the groups (2) to (11) in R$^{5\text{-}A}$ may be substituted with one to nine R$^{508}$s, R$^{508}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —NR$^{509}$R$^{510}$, when two or more R$^{501}$s are substituted, a plurality of R$^{508}$s may be the same or different, L$^{R5}$ represents (1) —O—, (2) —(C1-4 alkylene)-, (3) —O—(C1-4 alkylene)-, (4) —(C1-4 alkylene)-O—, (5) —NR$^{511}$— or (6) —SO$_{0\text{-}2}$—, R$^{501}$, R$^{502}$, R$^{503}$, R$^{504}$, R$^{505}$, R$^{506}$, R$^{507}$, R$^{509}$, R$^{510}$, or R$^{511}$ each independently represent (1) a hydrogen atom, (2) a C1-6 alkyl group, (3) a C2-6 acyl group, or (4) a C1-6 alkylsulfonyl group, m represents an integer of 0 to 2, n represents an integer of 0 to 5, and p represents an integer of 0 to 5.

[2] A compound represented by general formula (I) or a pharmaceutically acceptable salt thereof:

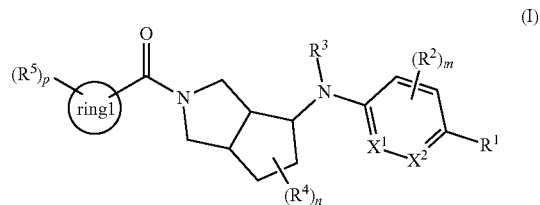

wherein R$^5$ represents (1) a halogen atom, (2) a C1-6 alkyl group, (3) a C2-6 alkenyl group, (4) a C2-6 alkynyl group, (5) a C1-6 alkoxy group, (6) a C1-6 alkylthio group, (7) a C1-6 alkylsulfinyl group, (8) a C1-6 alkylsulfonyl group, (9) a C2-6 acyl group, (10) a 3- to 6-membered cyclic group, (11) -L$^{R5}$-(3- to 6-membered cyclic group), (12) a hydroxyl group, (13) a nitro group, (14) a cyano group, (15) an oxo group, (16) —NR$^{501}$R$^{502}$, (17) —COOR$^{503}$, (18) —CONR$^{504}$R$^{505}$, or (19) —SO$_2$NR$^{506}$R$^{507}$, when p is two or more, a plurality of R$^5$s may be the same or different, the groups (2) to (11) in R$^5$ may be substituted with one to nine R$^{508}$s, and other symbols represent the same meaning as the symbols described in the above [1].

[3] A pharmaceutical composition containing the compound or the pharmaceutically acceptable salt thereof according to the above [1] or [2] as an active ingredient, and a pharmaceutically acceptable carrier

[4] The pharmaceutical composition according to the above [3], which is an ABHD6 inhibitor.

Effects of the Invention

The compound of the present disclosure has inhibitory activity on ABHD6, and thus the compound of the present disclosure is useful as an agent for preventing and/or treating a disease associated with ABHD6.

EMBODIMENTS FOR CARRYING OUT THE INVENTION

Hereinafter, the present disclosure will be described in detail.

In the present specification, examples of the halogen atom include fluorine, chlorine, bromine, and iodine atoms.

In the present specification, examples of the C1-4 alkyl group include methyl, ethyl, propyl, butyl groups, and isomers thereof.

In the present specification, examples of the C1-6 alkyl group include methyl, ethyl, propyl, butyl, pentyl, hexyl groups, and isomers thereof.

In the present specification, examples of the C2-6 alkenyl group include ethenyl, propenyl, butenyl, butadienyl, pentenyl, pentadienyl, hexenyl, hexadienyl groups, and isomers thereof.

In the present specification, examples of the C2-6 alkynyl group include ethynyl, propynyl, butynyl, butadiynyl, pentynyl, pentadiynyl, hexynyl, hexadiynyl groups, and isomers thereof.

In the present specification, examples of the C1-4 alkylene include methylene, ethylene, propylene, butylene, and isomers thereof.

In the present specification, examples of the C1-6 alkylene include methylene, ethylene, propylene, butylene, pentylene, hexylene, and isomers thereof.

In the present specification, the C1-4 haloalkyl group means, for example, an alkyl group substituted with one or more halogen atoms. Specific examples of the C1-4 haloalkyl group include a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, a 4-bromobutyl group, and isomers thereof.

In the present specification, the C1-6 haloalkyl group means, for example, an alkyl group substituted with one or more halogen atoms. Specific examples of the C1-6 haloalkyl group include a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, a 4-bromobutyl group, a 5,5,5-trifluoropentyl group, a 6,6,6-trifluorohexyl group, and isomers thereof.

In the present specification, the C1-6 haloalkylene means, for example, alkylene substituted with one or more halogen atoms. Specific examples of the C1-6 haloalkylene include fluoromethylene, chloromethylene, bromomethylene, iodomethylene, difluoromethylene, 1-fluoroethylene, 2-fluoroethylene, 2-chloroethylene, pentafluoroethylene, 1-fluoropropylene, 2-chloropropylene, 3-fluoropropylene, 3-chloropropylene, 4-bromobutylene, 5-fluoropentylene, 6-fluorohexylene, and isomers thereof.

In the present specification, the C2-6 haloalkenyl group means, for example, an alkenyl group substituted with one or more halogen atoms. Specific examples of the C2-6 haloalkenyl group include a 1-fluoroethenyl group, a 2-fluoroethenyl group, a 2-chloroethenyl group, a 1-fluoropropenyl group, a 2-chloropropenyl group, a 3-fluoropropenyl group, a 3-chloropropenyl group, a 4-bromobutenyl group, a 5,5,5-trifluoropentenyl group, a 6,6,6-trifluorohexenyl group, and isomers thereof.

In the present specification, the C2-6 haloalkynyl group means, for example, an alkynyl group substituted with one or more halogen atoms. Specific examples of the C2-6 haloalkynyl group include a 2-fluoroethynyl group, a 2-chloroethynyl group, a 3-fluoropropynyl group, a 3-chloropropynyl group, a 4-bromobutynyl group, a 5,5,5-trifluoropentynyl group, a 6,6,6-trifluorohexynyl group, and isomers thereof.

In the present specification, examples of the C1-4 alkoxy group includes methoxy, ethoxy, propoxy, butoxy groups, and isomers thereof.

In the present specification, examples of the C1-6 alkoxy group includes methoxy, ethoxy, propoxy, butoxy, pentyloxy, hexyloxy groups, and isomers thereof.

In the present specification, the C1-4 haloalkoxy group means, for example, an alkoxy group substituted with one or more halogen atoms. Specific examples of the C1-4 haloalkoxy group include a fluoromethoxy group, a chloromethoxy group, a bromomethoxy group, an iodomethoxy group, a difluoromethoxy group, a trifluoromethoxy group, a 1-fluoroethoxy group, a 2-fluoroethoxy group, a 2-chloroethoxy group, a pentafluoroethoxy group, a 1-fluoropropoxy group, a 2-chloropropoxy group, a 3-fluoropropoxy group, a 3-chloropropoxy group, a 4,4,4-trifluorobutoxy group, a 4-bromobutoxy group, and isomers thereof.

In the present specification, the C1-6 haloalkoxy group means, for example, an alkoxy group substituted with one or more halogen atoms. Specific examples of the C1-6 haloalkoxy group include a fluoromethoxy group, a chloromethoxy group, a bromomethoxy group, an iodomethoxy group, a difluoromethoxy group, a trifluoromethoxy group, a 1-fluoroethoxy group, a 2-fluoroethoxy group, a 2-chloroethoxy group, a pentafluoroethoxy group, a 1-fluoropropoxy group, a 2-chloropropoxy group, a 3-fluoropropoxy group, a 3-chloropropoxy group, a 4,4,4-trifluorobutoxy group, a 4-bromobutoxy group, a 5,5,5-trifluoropentyloxy group, a 6,6,6-trifluorohexyloxy group, and isomers thereof.

In the present specification, examples of the C1-6 alkylthio group include methylthio, ethylthio, propylthio, butylthio, pentylthio, hexylthio groups, and isomers thereof.

In the present specification, examples of the C1-6 alkylsulfinyl group include methylsulfinyl, ethylsulfinyl, propylsulfinyl, butylsulfinyl, pentylsulfinyl, hexylsulfinyl groups, and isomers thereof.

In the present specification, examples of the C1-6 alkylsulfonyl group include methylsulfonyl, ethylsulfonyl, propylsulfonyl, butylsulfonyl, pentylsulfonyl, hexylsulfonyl groups, and isomers thereof.

In the present specification, examples of the C3-6 cycloalkyl group include cyclopropyl, cyclobutyl, cyclopentyl, and cyclohexyl groups.

In the present specification, examples of the C2-6 acyl group include ethanoyl, propanoyl, butanoyl, pentanoyl, hexanoyl groups, and isomers thereof.

In the present specification, the 3- to 6-membered cyclic group represents a C3-6 carbocyclic ring and a 3- to 6-membered heterocyclic ring.

In the present specification, examples of the C3-6 carbocyclic ring include cyclopropane, cyclobutane, cyclopentane, cyclohexane, cyclobutene, cyclopentene, cyclohexene, cyclobutadiene, cyclopentadiene, cyclohexadiene, and benzene rings.

In the present specification, examples of the 3- to 6-membered heterocyclic ring include aziridine, azetidine, oxirane, oxetane, thiirane, thietane, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxadiazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane, dithiolane, and dithiane rings.

In the present specification, the 5- to 6-membered cyclic group represents a C5-6 carbocyclic ring and a 5- to 6-membered heterocyclic ring.

In the present specification, examples of the C5-6 carbocyclic ring include cyclopentane, cyclohexane, cyclopentene, cyclohexene, cyclopentadiene, cyclohexadiene, and benzene rings.

In the present specification, examples of the 5- to 6-membered heterocyclic ring include pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxadiazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane, dithiolane, and dithiane rings.

In the present specification, the 3- to 10-membered cyclic group represents a C3-10 carbocyclic ring and a 3- to 10-membered heterocyclic ring.

In the present specification, examples of the C3-10 carbocyclic ring include cyclopropane, cyclobutane, cyclopentane, cyclohexane, cycloheptane, cyclooctane, cyclononane, cyclodecane, cyclobutene, cyclopentene, cyclohexene, cycloheptene, cyclooctene, cyclononene, cyclodecene, cyclobutadiene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, bicyclo[1.1.1]pentane, bicyclo[2.1.1]hexane, bicyclo[2.1.1]hexene, bicyclo[2.2.1]heptane, bicyclo[2.2.1]heptene, bicyclo[3.1.1]heptane, bicyclo[3.1.1]heptene, bicyclo[2.2.2]octane, bicyclo[2.2.2]octene, bicyclo[3.2.1]octane, and bicyclo[3.2.1]octene rings.

In the present specification, examples of the 3- to 10-membered heterocyclic ring include the 3- to 6-membered heterocyclic rings, and azepine, diazepine, oxepin, thiepin, oxazepine, oxadiazepine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, dihydroazepine, tetrahydroazepine, perhydroazepine, dihydrodiazepine, tetrahydrodiazepine, perhydrodiazepine, dihydrooxepin, tetrahydrooxepin, perhydrooxepin, dihydrothiepin, tetrahydrothiepin, perhydrothiepin, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxaindane, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azabicyclo[3.2.1]octane, oxabicyclo[3.2.1]octane, thieno[3,2-c]pyrazole, thieno[2,3-c]pyrazole, thieno[2,3-d]thiazole, thieno[2,3-d][1.2.3]triazole, dihydropyrano[3,4-d]thiazole, dihydrothieno[2,3-b]pyran, dihydrothieno[3,2-c]pyran, dihydrothieno[3,2-b]pyran, dihydrothieno[3,2-c]thiopyran, tetrahydrothieno[3,2-b]pyridine, tetrahydrothieno[3,2-c]pyridine, and thieno[3,2-c]pyridine rings.

In the present specification, the 3- to 15-membered cyclic group represents a C3-15 carbocyclic ring and a 3- to 15-membered heterocyclic ring.

In the present specification, examples of the C3-15 carbocyclic ring include the C3-10 carbocyclic rings, and heptalene, biphenylene, as-indacene, s-indacene, acenaphthylene, acenaphthene, fluorene, phenalene, phenanthrene, and anthracene rings.

In the present specification, examples of the 3- to 15-membered heterocyclic ring include the 3- to 10-membered heterocyclic rings and benzoxadiazepine, benzothiadiazepine, benzoxazepine, benzothiazepine, benzodiazepine, dihydrobenzodiazepine, tetrahydrobenzodiazepine, benzodioxepane, dihydrobenzoxazepine, tetrahydrobenzoxazepine, benzoxepin, benzothiepine, benzazepine, dihydrobenzazepine, tetrahydrobenzazepine, perimidine, β-carboline, dihydrocarbazole, tetrahydrocarbazole, dihydrodibenzofuran, dihydrodibenzothiophene, tetrahydrodibenzofuran, tetrahydrodibenzothiophene, carbazole, dibenzofuran, dibenzothiophene, phenothiazine, phenoxazine, phenoxathiin, thianthrene, phenazine, phenanthroline, xanthene, dihydroacridine, tetrahydroacridine, acridine, phenanthridine, and dihydropyrrolo[1,2-b]thieno[2,3-d]pyrazole rings.

In the present specification, "one to two carbon atoms may be replaced with an oxygen atom or an optionally oxidized sulfur atom" means that one or two carbon atoms ($—CH_2—$) at a structurally possible position in the substituent may be replaced with an oxygen atom (—O—) or an optionally oxidized sulfur atom (—S—, —SO—, or $—SO_2—$). Specific examples of such a group in the case of the C1-6 alkyl group include a $CH_3—O—CH_2—$ group, a $CH_3—CH_2—O—CH_2—$ group, a $CH_3—O—CH_2—CH_2—$ group, a $CH_3—O—CH_2—CH_2—CH_2—$ group, a $CH_3—CH_2—O—CH_2—CH_2—$ group.

In the present disclosure, $X^1$ and $X^2$ are preferably N.

In the present disclosure, $R^1$ is preferably a chlorine atom or a bromine atom.

In the present disclosure, $R^2$ is preferably a halogen atom, a C1-6 alkyl group, a C1-6 alkoxy group, a C1-6 haloalkyl group, or a cyano group, and more preferably a chlorine atom, a methoxy group, a trifluoromethyl group, or a cyano group.

In the present disclosure, $R^X$ is preferably a halogen atom, a C1-6 alkyl group, a C1-6 alkoxy group, a C1-6 haloalkyl group, or a cyano group, and more preferably a chlorine atom, a methoxy group, a trifluoromethyl group, or a cyano group.

In the present disclosure, $R^3$ is preferably a hydrogen atom, a C1-6 alkyl group, a C1-6 haloalkyl group, a 3- to 10-membered cyclic group, or —CH$_2$-(3- to 10-membered cyclic group), and more preferably a hydrogen atom, a C1-6 alkyl group, a C1-6 haloalkyl group, a cyclopropyl group, —CH$_2$-benzene, —CH$_2$-pyridine, or —CH$_2$-imidazo[2,1-b]thiazole.

In the present disclosure, $R^4$ is preferably a halogen atom or a C1-6 alkyl group, and more preferably a fluorine atom or a methyl group.

In the present disclosure, ring 1 is preferably a 3- to 10-membered cyclic group or a ring structure selected from the group consisting of:

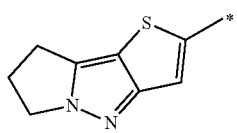

wherein the * mark represents a bonding position with a carbonyl group.

Ring 1 is more preferably a ring structure selected from the group consisting of:

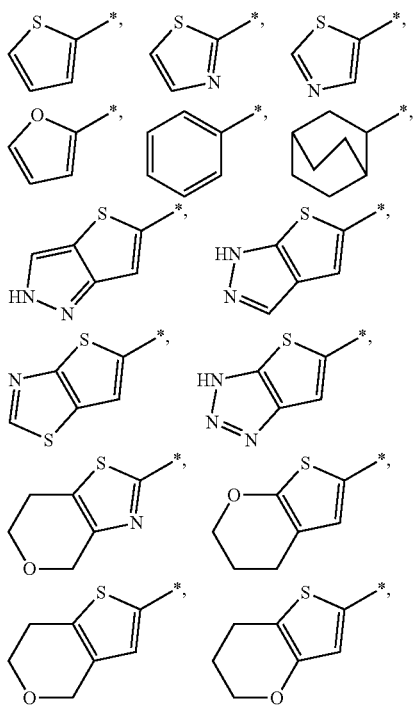

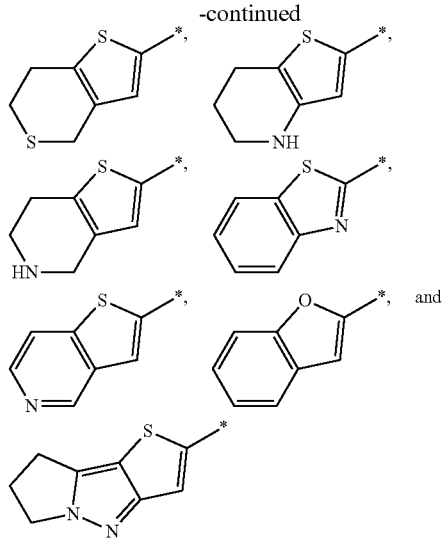

wherein the * mark represents a bonding position with a carbonyl group, and a hydrogen atom represented by NH may be replaced with $R^{5-A}$ or $R^5$.

Ring 1 is still more preferably a ring structure selected from the group consisting of:

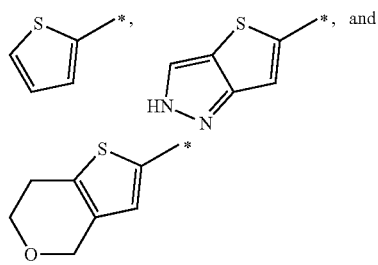

wherein the * mark represents a bonding position with a carbonyl group, and a hydrogen atom represented by NH may be replaced with $R^{5-A}$ or $R^5$.

In the present disclosure, $R^5$ is preferably a halogen atom, a C1-6 alkyl group, a C1-6 alkoxy group, a C1-6 haloalkyl group, a C1-6 haloalkoxy group, a 3- to 6-membered cyclic group, an oxo group, —NR$^{501}$R$^{502}$, or —COOR$^{503}$, more preferably a C1-6 alkyl group, a C1-6 alkoxy group, a C1-6 haloalkyl group, a C1-6 haloalkoxy group, a cyclopropyl group, a furan ring, an N-methylpyrazole ring, an oxo group, a dimethylamino group, or —COOCH$_3$, and still more preferably a C1-6 alkyl group, a C1-6 haloalkyl group, a C1-6 haloalkoxy group, or a cyclopropyl group.

In the present disclosure, $R^{5-A}$ is preferably a halogen atom, a C1-6 alkyl group, a C1-6 alkoxy group, a C1-6 haloalkyl group, a C1-6 haloalkoxy group, a 3- to 6-membered cyclic group, an oxo group, —NR$^{501}$R$^{502}$, or —COOR$^{503}$, more preferably a C1-6 alkyl group, a C1-6 alkoxy group, a C1-6 haloalkyl group, a C1-6 haloalkoxy group, a cyclopropyl group, a furan ring, an N-methylpyrazole ring, an oxo group, a dimethylamino group, or —COOCH$_3$, and still more preferably a C1-6 alkyl group, a C1-6 haloalkyl group, a C1-6 haloalkoxy group, or a cyclopropyl group.

In the present disclosure, m is preferably 0 or 1.
In the present disclosure, n is preferably 0, 1, or 2.
In the present disclosure, p is preferably 0, 1, or 2.

In the present disclosure, the compound represented by general formula (I-A) or general formula (I) is preferably a compound represented by general formula (I-1):

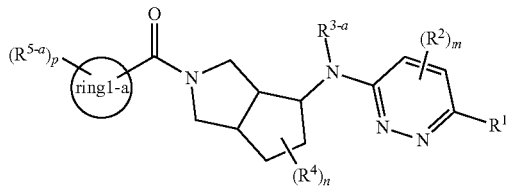

(I-1)

wherein R$^{3-a}$ represents (1) a hydrogen atom, (2) a C1-6 alkyl group, (3) a C1-6 haloalkyl group, (4) a cyclopropyl group, or (5) —CH$_2$-Q, Q represents (1) benzene, (2) pyridine, or (3) imidazo[2,1-b]thiazole, ring 1-a represents a ring structure selected from the group consisting of the following ring structures;

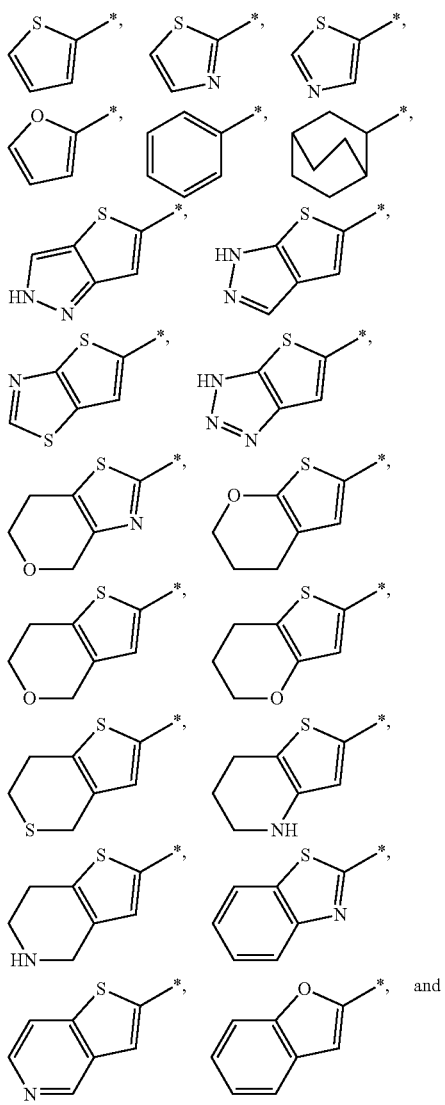

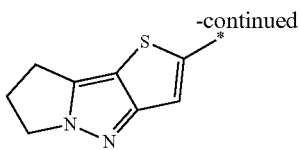

wherein the * mark represents a bonding position with a carbonyl group, and a hydrogen atom represented by NH may be replaced with R$^{5-a}$, R$^{5-a}$ represents (1) a C1-6 alkyl group, (2) a C1-6 alkoxy group, (3) a C1-6 haloalkyl group, (4) a C1-6 haloalkoxy group, (5) a cyclopropyl group, (6) a furan ring, (7) an N-methylpyrazole ring, (8) an oxo group, (9) a dimethylamino group, or (10) —COOCH$_3$, and other symbols represent the same meaning as the above symbols.

In the present disclosure, the compound represented by general formula (I-A) is preferably a combination of the preferred definitions of X$^1$, X$^2$, R$^1$, R$^2$, R$^3$, R$^4$, R$^{5-A}$, ring 1, n, m, and p.

In the present disclosure, the compound represented by general formula (I) is preferably a combination of the preferred definitions of X$^1$, X$^2$, R$^1$, R$^2$, R$^3$, R$^4$, R$^5$, ring 1, n, m, and p.

In the present disclosure, another embodiment of the compound represented by general formula (I-A) or general formula (I) is most preferably an example compound described in Examples described later or a pharmaceutically acceptable salt thereof.

All isomers are included in the present disclosure unless otherwise indicated. For example, the alkyl group, the alkoxy group, the alkylene group, and the like include linear groups and branched groups thereof. In addition, isomers (E-, Z-, cis-, and trans-forms) in a double bond, a ring, and a fused ring, isomers (R-, S-forms, α-, β-forms, enantiomer, and diastereomer) due to the presence of an asymmetric carbon, optically active substances (D-, L-, d-, and l-forms) having optical rotation, polar substances obtained through chromatographic separation (high-polarity substances and low-polarity substances), equilibrium compounds, rotational isomers, mixtures of these at an appropriate ratio, and racemic mixtures are all included in the present disclosure. In addition, all isomers by tautomerism are also included in the present disclosure.

In the present specification, the compound described as "rel-" in the compound name indicates that the steric configurations of a plurality of stereogenic centers are relative configurations.

In the present disclosure, unless otherwise specified, the symbol:

⫶⫶⫶ represents that a substituent is bonded to the back side of the paper surface (that is, α-configuration), the symbol:

▰ represents that a substituent is bonded to the front side of the paper surface (that is, β-configuration), and the symbol:

⁄ represents a mixture of α- and β-configurations at an appropriate ratio, as would be apparent to those skilled in the art.

[Salt]

The compound represented by general formula (I-A) is converted into a salt by a known method.

The salt is a pharmaceutically acceptable salt.

The salt is preferably water-soluble.

Examples of the pharmaceutically acceptable salt include, acid addition salts, alkali metal salts, alkaline earth metal salts, ammonium salts, and amine salts.

Examples of the acid addition salt include inorganic acid salts such as hydrochloride, hydrobromide, hydroiodide, sulfate, phosphate, and nitrate, or organic acid salts such as acetate, lactate, tartrate, benzoate, citrate, methanesulfonate, ethanesulfonate, trifluoroacetate, benzenesulfonate, toluenesulfonate, isethionate, glucuronate, and gluconate.

Examples of the alkali metal salt include a potassium salt and a sodium salt.

Examples of the alkaline earth metal salt include a calcium salt and a magnesium salt.

Examples of the ammonium salt include a tetramethylammonium salt.

Examples of the amine salt include a triethylamine salt, a methylamine salt, a dimethylamine salt, a cyclopentylamine salt, a benzylamine salt, a phenethylamine salt, a piperidine salt, a monoethanolamine salt, a diethanolamine salt, a tris(hydroxymethyl)aminomethane salt, a lysine salt, an arginine salt, and an N-methyl-D-glucamine salt.

In addition, the compound of the present disclosure can be converted into an N-oxide by any method. The N-oxide represents a compound obtained by oxidizing a nitrogen atom of the compound represented by general formula (I-A).

The compound represented by general formula (I-A) and a pharmaceutically acceptable salt thereof may exist in a non-solvated form or in a solvated form with a pharmaceutically acceptable solvent such as water or ethanol. The solvate is preferably a hydrate. The compound represented by general formula (I-A) and a pharmaceutically acceptable salt thereof can be converted into a solvate.

The compound represented by general formula (I-A) can form a cocrystal with an appropriate cocrystal former. The cocrystal is preferably a pharmaceutically acceptable cocrystal that is formed with a pharmaceutically acceptable cocrystal former. The cocrystal is typically defined as a crystal in which two or more different molecules are formed by intermolecular interaction that is different from ionic bonds. The cocrystal may be a complex of a neutral molecule and a salt. The cocrystal can be prepared by a known method, for example, by melting crystallization, recrystallization from a solvent, or physically pulverizing the components together. Suitable cocrystal formers include those described in WO 2006/007448.

In the present disclosure, all references to the compound of the present disclosure include a compound represented by general formula (I-A), a pharmaceutically acceptable salt thereof, an N-oxide thereof, a solvate thereof (for example, a hydrate), or a cocrystal thereof, or an N-oxide of a pharmaceutically acceptable salt of the compound represented by general formula (I-A), a solvate thereof (for example, a hydrate), or a cocrystal thereof.

[Prodrug]

The prodrug of the compound represented by general formula (I-A) refers to a compound that is converted into the compound represented by general formula (I-A) through a reaction with an enzyme, gastric acid, or the like in vivo. Examples of the prodrug of the compound represented by general formula (I-A) include: compounds in which an amino group is acylated, alkylated, or phosphorylated (for example, compounds in which the amino group of the compound represented by general formula (I-A) is eicosanoylated, alanylated, pentylaminocarbonylated, (5-methyl-2-oxo-1,3-dioxolen-4-yl)methoxycarbonylated, tetrahydrofuranylated, pyrrolidyl methylated, pivaloyloxymethylated, acetoxymethylated, tert-butylated, or the like) in the case where the compound represented by general formula (I-A) has an amino group; compounds in which a hydroxyl group is acylated, alkylated, phosphorylated, or borated (for example, compounds in which the hydroxyl group of the compound represented by general formula (I-A) is acetylated, palmitoylated, propanoylated, pivaloylated, succinylated, fumarylated, alanylated, dimethylaminomethylcarbonylated, or the like) in the case where the compound represented by general formula (I-A) has a hydroxyl group; and compounds in which a carboxy group is esterified or amidated (for example, compounds in which the carboxy group of the compound represented by general formula (I-A) is ethyl esterified, phenyl esterified, carboxymethyl esterified, dimethylaminomethyl esterified, pivaloyloxymethyl esterified, 1-{(ethoxycarbonyl)oxy}ethyl esterified, phthalidyl esterified, (5-methyl-2-oxo-1,3-dioxolen-4-yl)methyl esterified, 1-{[(cyclohexyloxy)carbonyl]oxy}ethyl esterified, methylamidated, or the like) in the case where the compound represented by general formula (I-A) has a carboxy group. These compounds can be produced by a method known per se. The prodrug of the compound represented by general formula (I-A) may be either a hydrate or a non-hydrate. In addition, the prodrug of the compound represented by general formula (I-A) may be a compound that is converted into the compound represented by general formula (I-A) under a physiological condition as described in "Development of Pharmaceuticals", Vol. 7, "Molecular Design", pp. 163 to 198, published by Hirokawa Shoten, 1990.

Furthermore, each atom constituting the compound represented by general formula (I-A) may be substituted with an isotope thereof (for example, $^{2}$H, $^{3}$H, $^{11}$C $^{13}$C, $^{14}$C, $^{15}$N, $^{16}$N, $^{17}$O, $^{18}$O, $^{18}$F, $^{35}$S, $^{36}$Cl, $^{77}$Br, and $^{125}$I) or the like.

[Method for Producing Compound of Present Disclosure]

The compound of the present disclosure can be produced by appropriately improving known methods, for example, methods shown below, methods equivalents thereto, the method described in Comprehensive Organic Transformations: A Guide to Functional Group Preparations, 3rd Edition (Richard C. Larock, John Wiley & Sons Inc, 2018), the methods described in Examples or the like, and using a combination thereof. A salt may be used as the starting material thereof. The order of carrying out each reaction can be appropriately changed depending on the protecting group introduced and reaction conditions.

In addition, a compound having an amino group, a carboxyl group, or a hydroxyl group can be produced, if necessary, by performing a known deprotection reaction after an appropriate reaction step, by using a compound protected with a protecting group commonly used for these groups. The protecting group is, for example, the protecting groups described in T. W. Greene, Protective Groups in Organic Synthesis, Wiley, New York, 5th Edition, 2014.

Examples of the protecting group of a carboxyl group include methyl, ethyl, tert-butyl, trichloroethyl, benzyl (Bn), phenacyl, p-methoxybenzyl, trityl, and 2-chlorotrityl.

Examples of the protecting group of an amino group or a tetrazolyl group include a benzyloxycarbonyl group, a tert-butoxycarbonyl group, an allyloxycarbonyl (Alloc) group, a 1-methyl-1(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, and a 2-(trimethylsilyl)ethoxymethyl (SEM) group.

Examples of the protecting group of a hydroxyl group or hydroxamic acid include methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc).

The deprotection reaction is known, and can be performed by, for example, the following methods: (1) a deprotection reaction by alkaline hydrolysis;

(2) a deprotection reaction under an acidic condition;
(3) a deprotection reaction by hydrogenolysis;
(4) a deprotection reaction of a silyl group;
(5) a deprotection reaction by using a metal; and
(6) a deprotection reaction by using a metal complex.
These methods are specifically described as follows.

(1) The deprotection reaction by alkaline hydrolysis is performed, for example, at 0 to 40° C., in an organic solvent (for example, methanol, tetrahydrofuran (hereinafter, THF), and dioxane), by using a hydroxide of an alkali metal (for example, sodium hydroxide, potassium hydroxide, and lithium hydroxide), a hydroxide of an alkaline earth metal (for example, barium hydroxide and calcium hydroxide), a carbonate (for example, sodium carbonate and potassium carbonate), or an aqueous solution or mixture thereof.

(2) The deprotection reaction under an acidic condition is performed, for example, at 0 to 100° C., in an organic solvent (for example, dichloromethane, chloroform, dioxane, ethyl acetate, methanol, isopropyl alcohol, THF, and anisole), in an organic acid (for example, acetic acid, trifluoroacetic acid, methanesulfonic acid, and p-tosylic acid) or an inorganic acid (for example, hydrochloric acid and sulfuric acid), or a mixture thereof (for example, hydrogen bromide/acetic acid), in the presence or absence of 2,2,2-trifluoroethanol.

(3) The deprotection reaction by hydrogenolysis is performed, for example, at 0 to 200° C., in a solvent (for example, an ether-based solvent such as THF, dioxane, dimethoxyethane, and diethyl ether; an alcohol-based solvent such as methanol and ethanol; a benzene-based solvent such as benzene and toluene; a ketone-based solvent such as acetone and methyl ethyl ketone; a nitrile-based solvent such as acetonitrile; an amide-based solvent such as N,N-dimethylformamide (hereinafter, DMF); water, ethyl acetate, acetic acid, or a mixed solvent of two or more thereof), in the presence of a catalyst (for example, palladium-carbon, palladium black, palladium hydroxide-carbon, platinum oxide, and Raney nickel), under a hydrogen atmosphere under normal pressure or pressure, or in the presence of ammonium formate.

(4) The deprotection reaction of a silyl group is performed, for example, at 0 to 40° C., in an organic solvent (for example, THF and acetonitrile) miscible with water, by using tetrabutylammonium fluoride. In addition, the deprotection reaction is performed, for example, at −10 to 100° C., in an organic acid (for example, acetic acid, trifluoroacetic acid, methanesulfonic acid, and p-tosylic acid) or an inorganic acid (for example, hydrochloric acid and sulfuric acid), or a mixture thereof (for example, hydrogen bromide/acetic acid).

(5) The deprotection reaction using a metal is performed, for example, at 0 to 40° C., in an acidic solvent (for example, a mixed solution of acetic acid, a buffer solution having a pH of 4.2 to 7.2, or a solution thereof with an organic solvent such as THF), in the presence of powdery zinc while applying ultrasonic waves if necessary.

(6) The deprotection reaction using a metal complex is performed, for example, at 0 to 40° C., in an organic solvent (for example, dichloromethane, DMF, THF, ethyl acetate, acetonitrile, dioxane, and ethanol), water, or a mixed solvent thereof, in the presence of a trapping reagent (for example, tributyltin hydride, triethylsilane, dimedone, morpholine, diethylamine, and pyrrolidine), an organic acid (for example, acetic acid, formic acid, and 2-ethylhexanoic acid), and/or an organic acid salt (for example, sodium 2-ethylhexanoate and potassium 2-ethylhexanoate), in the presence or absence of a phosphine-based reagent (for example, triphenylphosphine), by using a metal complex (for example, tetrakistriphenylphosphine palladium(0), bis(triphenylphosphine)palladium(II) dichloride, palladium(II) acetate, and tris(triphenylphosphine)rhodium(I) chloride).

The compound represented by general formula (I-A) can be produced by Reaction Scheme 1.

Reaction scheme 1

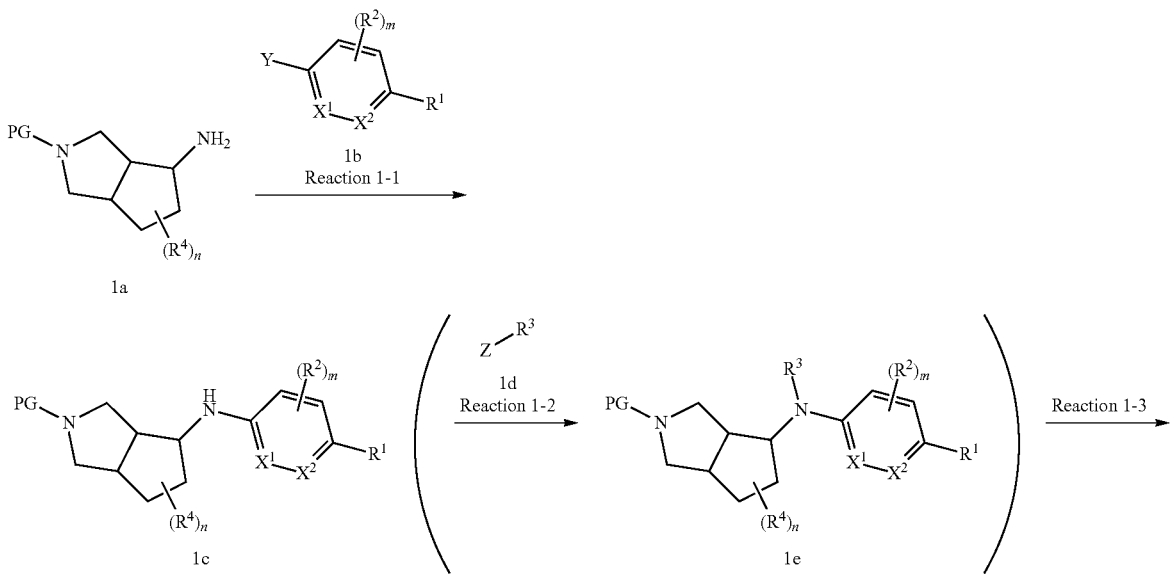

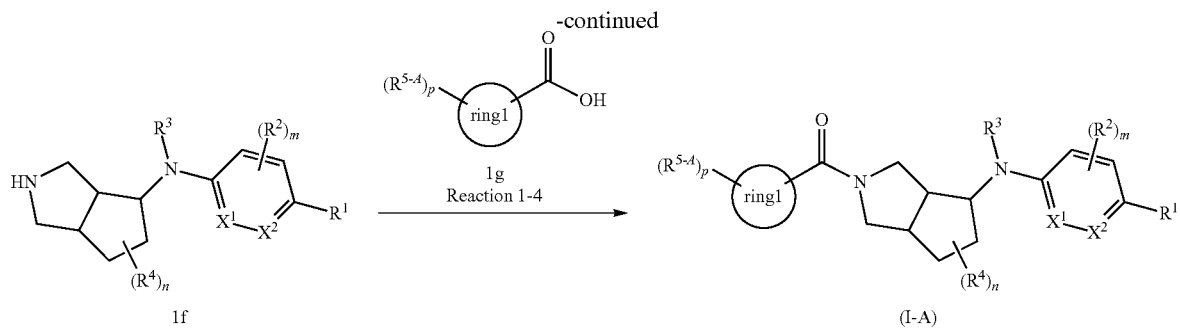

wherein PG represents a protecting group of an amino group, Y represents a halogen atom, Z represents a halogen atom, and other symbols represent the same meaning as described above.

In Reaction Scheme 1, Reaction 1-1 is a halogen substitution reaction or a cross-coupling reaction. The halogen substitution reaction is known, and is performed, for example, through reaction at 0 to 200° C., in an organic solvent (DMF, dimethyl sulfoxide, chloroform, dichloromethane, diethyl ether, THF, methyl t-butyl ether, and the like), in the presence of a base (sodium ethylate, sodium hydroxide, potassium hydroxide, triethylamine, diisopropylethylamine, sodium carbonate, sodium bicarbonate, potassium carbonate, cesium carbonate, tripotassium phosphate, cesium fluoride, barium hydroxide, tetrabutylammonium fluoride, and the like), or an aqueous solution or mixture thereof.

The cross-coupling reaction is known, and is performed, for example, through reaction at room temperature to 120° C., in an organic solvent (benzene, toluene, DMF, dioxane, THF, methanol, acetonitrile, dimethoxyethane, acetone, and the like), in the presence of a base (sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide, tetrabutylammonium fluoride, and the like), or an aqueous solution or mixture thereof and a catalyst (tetrakis(triphenylphosphine)palladium (Pd(PPh$_3$)$_4$), bis(triphenylphosphine)palladium dichloride (PdCl$_2$(PPh$_3$)$_2$), palladium acetate (Pd(OAc)$_2$), palladium black, 1,1'-bis(diphenylphosphinoferrocene)dichloropalladium (PdCl$_2$(dppf)$_2$), diallylpalladium dichloride (PdCl$_2$(allyl)$_2$), phenylbis(triphenylphosphine)palladium iodide (PhPdI(PPh$_3$)$_2$), and the like).

In Reaction Scheme 1, Reaction 1-2 is an N-alkylation reaction. The N-alkylation reaction is known, and is performed, for example, through reaction at 0 to 100° C., in an organic solvent (DMF, dimethyl sulfoxide, chloroform, dichloromethane, diethyl ether, THF, methyl t-butyl ether, and the like), in the presence of a hydroxide of an alkali metal (sodium hydroxide, potassium hydroxide, lithium hydroxide, and the like), a hydroxide of an alkaline earth metal (barium hydroxide, calcium hydroxide, and the like), a carbonate (sodium carbonate, potassium carbonate, and the like), or an aqueous solution or mixture thereof.

In Reaction Scheme 1, Reaction 1-3 is a deprotection reaction, and can be performed in the same manner as described above.

In Reaction Scheme 1, Reaction 1-4 is an amidation reaction. The amidation reaction is known, and examples thereof include:

(1) a method using an acid halide;
(2) a method using a mixed acid anhydride; and
(3) a method using a condensing agent. These methods are specifically described as follows.

(1) The method using an acid halide is performed, for example, by reacting a carboxylic acid with an acid halogenating agent (oxalyl chloride, thionyl chloride, and the like) at −20° C. in an organic solvent (chloroform, dichloromethane, diethyl ether, THF, and the like) or in the absence of a solvent to reflux temperature, and reacting the obtained acid halide with an amine at 0 to 40° C. in the presence of a base (pyridine, triethylamine, dimethylaniline, dimethylaminopyridine, diisopropylethylamine, and the like) in an organic solvent (chloroform, dichloromethane, diethyl ether, THF, and the like). Alternatively, the method can also be performed by reacting the obtained acid halide with an amine at 0 to 40° C. by using an alkali aqueous solution (sodium bicarbonate water, sodium hydroxide solution, and the like) in an organic solvent (dioxane, THF, and the like).

(2) The method using a mixed acid anhydride is performed, for example, by reacting a carboxylic acid with an acid halide (pivaloyl chloride, tosyl chloride, mesyl chloride, and the like) or an acid derivative (ethyl chloroformate, isobutyl chloroformate, and the like) at 0 to 40° C. in an organic solvent (chloroform, dichloromethane, diethyl ether, THF, and the like) or in the absence of a solvent in the presence of a base (pyridine, triethylamine, dimethylaniline, dimethylaminopyridine, diisopropylethylamine, and the like), and reacting the obtained mixed acid anhydride with an amine at 0 to 40° C. in an organic solvent (chloroform, dichloromethane, diethyl ether, THF, and the like).

(3) The method using a condensing agent is performed, for example, by reacting a carboxylic acid with an amine at 0 to 40° C., in an organic solvent (chloroform, dichloromethane, DMF, diethyl ether, THF, and the like) or in the absence of a solvent, in the presence or absence of a base (pyridine, triethylamine, dimethylaniline, dimethylaminopyridine, and the like), by using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodine, 1-propylphosphonic acid cyclic anhydride (1-propanephosphonic acid cyclic anhydride, propyl phosphonic acid (PPA), or the like), and the like, O-(7-azabenzotriazol-1-yl)-N,N,N',N'-tetramethyluronium hexafluorophosphate (HATU), in the presence or absence of 1-hydroxybenztriazole (HOBt).

All of these reactions (1), (2), and (3) are desirably performed under an inert gas (argon, nitrogen, or the like) atmosphere under an anhydrous condition.

The compound represented by general formula 1a can be produced by Reaction Scheme 2.

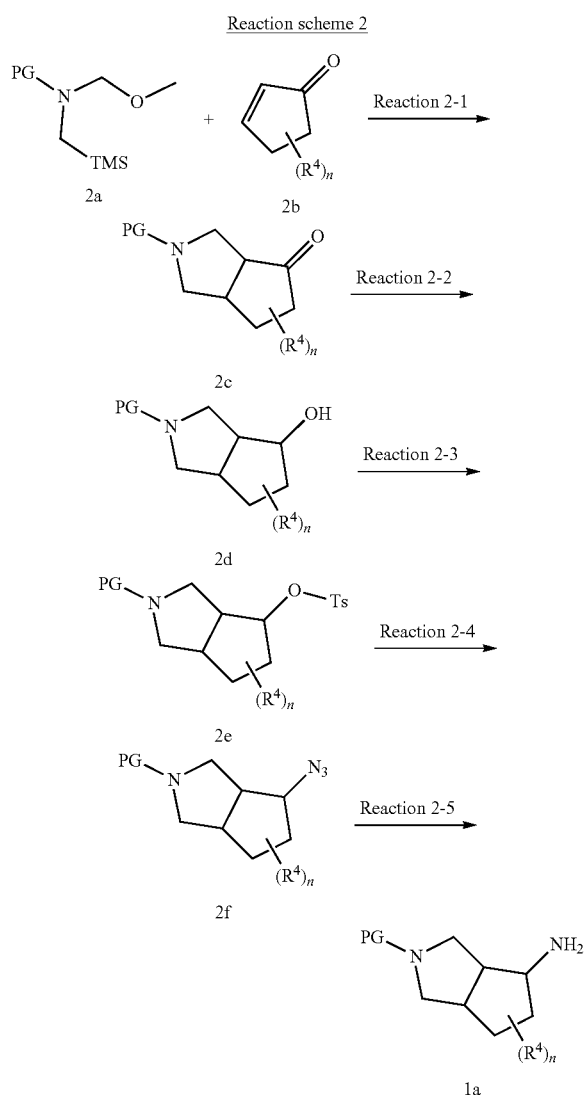

Reaction scheme 2

In Reaction Scheme 2, all symbols represent the same meaning as the symbols described above.

In Reaction Scheme 2, Reaction 2-1 is a cyclization reaction, and is performed, for example, at 0 to 100° C., in an organic solvent (DMF, dimethyl sulfoxide, chloroform, dichloromethane, diethyl ether, THF, methyl t-butyl ether, and the like), in the presence of an acid (trifluoroacetic acid and the like).

In Reaction Scheme 2, Reaction 2-2 is a reduction reaction of a carbonyl group, and is performed at 0 to 40° C., in an organic solvent (dichloroethane, dichloromethane, DMF, THF, a mixture thereof, and the like), in the presence of a reducing agent (such as sodium borohydride).

In Reaction Scheme 2, Reaction 2-3 is a tosylation reaction, and can be performed by reacting p-toluenesulfonyl chloride at 0 to 100° C., in an organic solvent (for example, dichloromethane, diethyl ether, THF, acetonitrile, benzene, toluene), in the presence of a base (for example, pyridine, triethylamine, dimethylaniline, dimethylaminopyridine, and diisopropylethylamine).

In Reaction Scheme 2, Reaction 2-4 is an azidation reaction, and can be performed, for example, by reacting sodium azide at 0 to 100° C., in an organic solvent (DMF, dimethyl sulfoxide, chloroform, dichloromethane, diethyl ether, THF, methyl t-butyl ether, and the like).

In Reaction Scheme 2, Reaction 2-5 is a reduction reaction of an azide group, and is performed at 0 to 200° C., in an organic solvent (for example, THF, dioxane, dimethoxyethane, diethyl ether, methanol, ethanol, benzene, toluene, acetone, methyl ethyl ketone, acetonitrile, DMF, ethyl acetate, acetic acid, or a mixed solvent of two or more thereof), in the presence of a hydrogenation catalyst (palladium-carbon, palladium black, palladium, palladium hydroxide, platinum dioxide, platinum-carbon, nickel, Raney nickel, ruthenium chloride, and the like), in the presence or absence of an acid (hydrochloric acid, sulfuric acid, hypochlorous acid, boric acid, tetrafluoroboric acid, acetic acid, p-toluenesulfonic acid, oxalic acid, trifluoroacetic acid, formic acid, and the like), under a hydrogen atmosphere under normal pressure or pressure.

In each reaction in the present specification, the compounds represented by general formula 1b, general formula 1d, general formula 1g, general formula 2a, and general formula 2b used as starting materials are known, or can be easily produced by combining known methods, for example, the methods described in Comprehensive Organic Transformations: A Guide to Functional Group Preparations, 3rd Edition (Richard C. Larock, John Wiley & Sons Inc, 2018) and the like, or methods obtained by partially modifying known methods or the like.

Among the compounds of the present disclosure, a compound having optical activity can be produced by using a starting material or reagent having optical activity, or by optically separating a racemic intermediate and then converting to the present disclosure compound therefrom, or optically separating a racemic form of the compound of the present disclosure.

This optical separation is known, and examples thereof include a method in which a salt, a complex, or the like is formed with another optically active compound, and then a target compound is isolated after recrystallization or directly separated using a chiral column or the like.

In the reactions in the present specification, a reaction involving heating can be performed using a water bath, an oil bath, a sand bath, or a microwave, as would be apparent to those skilled in the art.

In the reactions in the present specification, a solid-phase supported reagent that is supported on a polymer (for example, polystyrene, polyacrylamide, polypropylene, polyethylene glycol, and the like) may be appropriately used.

In the reactions in the present specification, the reaction product can be purified by ordinary purification means, for example, distillation under normal pressure or reduced pressure, high-performance liquid chromatography using silica gel or magnesium silicate, thin-layer chromatography, methods using an ion-exchange resin or a scavenger resin, column chromatography, washing, and recrystallization. The purification may be performed for each reaction or may be performed after completion of some reactions.

[Toxicity]

The toxicity of the compound of the present disclosure is low, and therefore can be used as a medicament safely.

[Application to Medicament]

The compound of the present disclosure has inhibitory activity on ABHD6, and thus the compound of the present disclosure is useful as an agent for preventing and/or treating diseases associated with ABHD6, for example, pain, neurological diseases, inflammatory diseases, autoimmune diseases, metabolic diseases, and malignant tumors.

More specifically, examples of the pain include pain associated with osteoarthritis, cancer pain, pain associated with chemotherapy, chronic low back pain, low back pain associated with osteoporosis, fracture pain, pain associated with rheumatoid arthritis, neuropathic pain, post-herpetic pain, pain associated with diabetic neuropathy, pain associated with fibromyalgia, pain associated with pancreatitis, pain associated with interstitial cystitis or bladder pain syndrome, pain associated with endometriosis, pain associated with irritable bowel syndrome, migraine, and pain associated with pulpitis.

Examples of the neurological disease include tremor, dyskinesia, dystonia, spasticity, compressive and obsessive behavior, depression, mental disorders including anxiety disorder (for example, panic disorder, acute stress disorder, post-traumatic stress disorder, obsessive-compulsive disorder, agoraphobia, social phobia), mood disorder, epilepsy, traumatic brain injury, spinal cord injury, multiple sclerosis, encephalomyelitis, Parkinson's disease, Huntington's disease, Alzheimer's disease, and sleep disorder.

Examples of the inflammatory disease include arthritis, rheumatoid arthritis, osteoarthritis, spondylitis, gout, vasculitis, Crohn's disease, and irritable bowel syndrome.

Examples of the autoimmune disease include psoriasis, amyotrophic lateral sclerosis (ALS), multiple sclerosis, Sjögren's syndrome, systemic lupus erythematosus, and AIDS.

Examples of the metabolic disease include obesity, metabolic syndrome, dyslipidemia, diabetes, and fatty liver.

Examples of the malignant tumor include breast cancer, ovarian cancer, large bowel cancer (for example, colon cancer), lung cancer (for example, non-small cell lung cancer), prostate cancer, head and neck cancer (for example, oral squamous cell cancer, head and neck squamous cell cancer, pharyngeal cancer, laryngeal cancer, tongue cancer, thyroid cancer, and acoustic schwannoma), lymphoma (for example, B-cell lymphoma and T-cell lymphoma), uveal malignant melanoma, thymoma, mesothelioma, esophageal cancer, gastric cancer, duodenal cancer, hepatocellular cancer, bile duct cancer, gallbladder cancer, pancreatic cancer, renal cell cancer, renal pelvic and ureteral cancer, bladder cancer, penile cancer, testicular cancer, uterine cancer, vaginal cancer, vulvar cancer, skin cancer (for example, malignant melanoma), malignant bone tumor, soft tissue sarcoma, chondrosarcoma, leukemia (for example, acute myelogenous leukemia, acute lymphocytic leukemia, chronic myelogenous leukemia, and chronic lymphocytic leukemia), myelodysplastic syndrome, brain tumor or multiple myeloma.

In the present specification, the prevention and/or treatment of a malignant tumor includes, for example, (a) a treatment for reducing the proliferation of cancer cells, (b) a treatment for attenuating symptoms resulting from cancer and improving the quality of life of a cancer patient, (c) a treatment for reducing the dose of other anticancer agents or cancer therapeutic adjuvants that have already been administered, (d) a treatment for suppressing the progression of cancer, (e) a treatment for suppressing the recurrence of cancer, and/or (f) a treatment for prolonging the survival of a cancer patient. In addition, "suppressing the progression of cancer" means to delay the progression of cancer, stabilize symptoms associated with cancer, and reverse the progression of symptoms. "Suppressing the recurrence" means to prevent cancer recurrence in a patient whose cancer lesion has completely or substantially eliminated or removed by cancer treatment or cancer surgical resection.

In the use of the compound of the present disclosure for the purpose of preventing and/or treating the above-mentioned diseases, the substance that acts as an active ingredient, is usually formulated together with a pharmaceutically acceptable carrier such as various additives or solvents, and then administered systemically or topically, orally or parenterally. Here, the pharmaceutically acceptable carrier means a substance other than the active ingredient, which is generally used for pharmaceutical preparation. The pharmaceutically acceptable carrier preferably does not exhibit a pharmacological action at the dosage of the preparation, is harmless, and does not interfere with the therapeutic effect of the active ingredient. The pharmaceutically acceptable carrier can also be used for the purpose of, for example, enhancing the usefulness of the active ingredient and the preparation, facilitating the formulation, stabilizing the quality, or improving the usability. Specifically, substances described in "Japanese Pharmaceutical Excipients Directory" published in 2000 by Yakuji Nippo Limited (edited by International Pharmaceutical Excipients Council Japan) and the like may be appropriately selected according to the purpose.

The compound of the present disclosure can be administered to a mammal (preferably human, more preferably a human patient) in a pharmaceutically effective amount.

Since the dosage of the compound of the present disclosure depends on age, body weight, symptom, desired therapeutic effect, route of administration, period of treatment, and the like, the dosage inevitably varies. The compound of the present disclosure is generally administered orally in the range of 0.1 ng to 1,000 mg per patient per administration, or parenterally administered or continuously administered intravenously in the range of 0.01 ng to 100 mg per patient per administration.

Needless to say, the dosage varies depending on various conditions as described above. Therefore, a dosage smaller than the above dosage may be sufficient, or a dosage beyond the above range may be required.

Examples of the dosage form thereof include preparations for oral administration (for example, tablets, capsules, granules, powders, oral solutions, syrups, and oral jellies), preparations for oral cavity (for example, oral tablets, oral sprays, oral semisolids, and oral rinses), preparations for injection (for example, injectables), preparations for dialysis (for example, dialysis agents), preparations for inhalation (for example, inhalants), preparations for ophthalmic application (for example, eye drops and ophthalmic ointments), preparations for otologic application (for example, ear drops), preparations for nasal application (for example, nose drops), preparations for rectum (for example, suppositories, semisolids for rectum, and enemas for rectal application), preparations for vagina (for example, vaginal tablets and vaginal suppositories), and preparations for skin (for example, external solid agents, external liquid agents, sprays, ointments, creams, gels, and patches).

[Preparation for Oral Administration]

Examples of the preparation for oral administration include tablets, capsules, granules, powders, oral solutions, syrups, and oral jellies. The preparation for oral administration includes rapidly disintegrating preparations in which the releasability of the active ingredient from the preparation is not particularly adjusted; and controlled-release preparations such as enteric-coated preparations and sustained-release preparations in which the releasability is adjusted according to the purpose by unique formulation design and formulation method. The enteric-coated preparation refers to a preparation designed to release the active ingredient mainly in the small intestine without releasing the active ingredient in the stomach, for the purpose of preventing the degradation of the active ingredient in the stomach or reducing the irritation of the active ingredient to the stomach. The enteric-coated preparation can be usually produced by coating with an acid-insoluble enteric-coated base. The sustained-release preparation refers to a preparation in which the release rate, release time, and release site of the active ingredient from the preparation are adjusted for the purpose of reducing the number of administrations or attenuating side effects. The sustained-release preparation can be usually produced by using an appropriate sustained-release agent. Among preparations for oral administration, capsules, granules, tablets, and the like can be coated with an appropriate coating agent such as a saccharide, a sugar alcohol, or a polymer compound, for the purpose of, for example, facilitating ingestion or preventing degradation of the active ingredient.

(1) Tablet

The tablet is a solid preparation that is administered orally and has a certain shape. The tablet includes those generally referred to as tablets, such as uncoated tablets, film-coated tablets, sugar-coated tablets, multilayer tablets, and dry-coated tablets, as well as orally rapidly disintegrating tablets, chewable tablets, effervescent tablets, dispersible tablets, and soluble tablets. In the production of the uncoated tablet, the following method (a), (b), or (c) is usually used:

(a) Additives such as an excipient, a binder, and a disintegrant are added to the active ingredient and mixed to prepare a homogeneous mixture, the mixture is granulated by an appropriate method using water or a solution containing a binder, then a lubricant or the like is added to the granulated product and mixed, and the resulting mixture was compression-molded;

(b) Additives such as an excipient, a binder, and a disintegrant are added to the active ingredient and mixed to prepare a homogeneous mixture, and the mixture is directly compression-molded; or the active ingredient, a lubricant, and the like are added to granules prepared in advance with additives to prepare a homogeneous mixture, and then the mixture is compression-molded; and (c) Additives such as an excipient and a binder are added to the active ingredient and mixed to prepare a homogeneous mixture, a kneaded product obtained by wetting the mixture with a solvent is poured into a predetermined mold and molded, and then the molded product is dried by an appropriate method.

The film-coated tablet can be usually produced by thinly coating an uncoated tablet with an appropriate coating agent such as a polymer compound. The sugar-coated tablet can be usually produced by coating an uncoated tablet with a coating agent containing a saccharide or a sugar alcohol. The multilayer tablet can be produced by forming layers of powder particles having different compositions and compression-molding the layered powder particles by an appropriate method. The dry-coated tablet can be produced by covering an inner core tablet with an outer layer having a composition different from that of the inner core tablet. The tablet can also be an enteric-coated tablet or a sustained-release tablet by a known appropriate method. The orally rapidly disintegrating tablet, the chewable tablet, the effervescent tablet, the dispersible tablet, and the soluble tablet are those in which unique functions are imparted to the tablets by appropriate selection of additives, and can be produced according to the above-described methods for producing the tablet. Incidentally, the orally rapidly disintegrating tablet refers to a tablet that can be taken by being rapidly dissolved or disintegrated in the oral cavity; the chewable tablet refers to a tablet that is chewed and taken; the effervescent tablet refers to a tablet that dissolves or disperses while rapidly foaming in water; the dispersible tablet refers to a tablet that is taken by being dispersed in water; and the soluble tablet refers to a tablet that is taken by being dissolved in water. The effervescent tablet can be produced by using an appropriate acidic substance, a carbonate, a bicarbonate, or the like as an additive.

(2) Capsule

The capsule is a preparation in which ingredients are filled in a capsule or encapsulated with a capsule base, and includes hard capsules, soft capsules, and the like. The hard capsule can be produced by adding an additive such as an excipient to the active ingredient and mixing them to prepare a homogeneous mixture, or forming the mixture into particles or a molded product by an appropriate method, and filling, in a capsule, the mixture, the particles, or the molded product as it is or after each content is slightly molded. The soft capsule can be produced by encapsulating a mixture of the active ingredient and an additive in a certain shape with an appropriate capsule base such as gelatin having increased plasticity by adding glycerin, D-sorbitol, or the like. The capsule may be an enteric-coated capsule or a sustained-release capsule prepared by a known appropriate method, and a colorant, a preservative, or the like may be added to the capsule base.

(3) Granule

The granule is a preparation granulated in a granular form, and includes effervescent granules and the like in addition to those generally referred to as granules. In the production of the granule, the following method (a), (b), or (c) is usually used:

(a) An excipient, a binder, a disintegrant, or other additives are added to a powdery active ingredient and mixed to prepare a homogeneous mixture, and then the mixture is granulated by an appropriate method;

(b) An additive such as an excipient is added to the active ingredient prepared in a granular form in advance, and mixed to prepare a homogeneous mixture; and (c) An additive such as an excipient is added to the active ingredient prepared in a granular form in advance and mixed, and the mixture is then formed into granules by an appropriate method.

The granule may be coated as necessary, and may be an enteric-coated granule or a sustained-release granule prepared by a known appropriate method. The effervescent granule can be produced by using an appropriate acidic substance, a carbonate, a bicarbonate, or the like as an additive. The effervescent granule refers to a granule that dissolves or disperses while rapidly foaming in water. The granule can also be made into a fine granule by adjusting the size of the particle.

(4) Powder

The powder is a powdery preparation, and can be usually produced by adding an excipient or other additives to the active ingredient and mixing them to prepare a homogeneous mixture.

(5) Oral Solution

The oral solution is a liquid or flowable viscous gel preparation, and includes, in addition to those generally referred to as oral solutions, an elixir, a suspension, an emulsion, a lemonade, and the like. The oral solution can be usually produced by adding an additive and purified water to the active ingredient, followed by mixing, uniformly dissolving or emulsifying or suspending, and filtering as necessary. The elixir refers to a clear liquid oral solution containing sweet and aromatic ethanol. The elixir can be usually produced by adding ethanol, purified water, a flavoring agent, and white sugar, other saccharides or a sweetener to a solid active ingredient or a leachate thereof, dissolving components, and preparing a clear liquid by filtration or other methods. The suspension refers to an oral solution in which the active ingredient is finely and homogeneously suspended. The suspension can be usually produced by adding a suspending agent or other additives and purified water or oil to a solid active ingredient, and performing suspension by an appropriate method to homogenize the entire active ingredient. The emulsion refers to an oral solution in which the active ingredient is finely and homogeneously emulsified. The emulsion can be usually produced by adding an emulsifier and purified water to a liquid active ingredient, and performing emulsification by an appropriate method to homogenize the mixture. The lemonade refers to a clear liquid oral solution having a sweet taste and a sour taste.

(6) Syrup

The syrup is a viscous liquid preparation or solid preparation containing a saccharide or sweetener, and includes preparations for syrup and the like. The syrup can be usually produced by adding the active ingredient to a solution of white sugar, other saccharides or a sweetener, or a single syrup, followed by dissolving, mixing, suspending, or emulsifying, and if necessary, boiling the mixed liquid, followed by hot filtration. The preparation for syrup refers to a granular or powdery preparation that becomes a syrup when water is added, and may also be referred to as a dry syrup. The preparation for syrup can be usually produced using a saccharide or a sweetener as an additive in accordance with the method for producing the granule or powder.

(7) Oral Jelly

The oral jelly is a formed gel preparation having no fluidity, and can be usually produced by adding an additive and a polymer gel base to the active ingredient and mixing them, gelatinizing the mixture by an appropriate method, and forming the resulting gel into a certain shape.

[Preparation for Injection]

(1) Injectable

The injectable is a solution, a suspension or an emulsion, or a solid sterile preparation to be dissolved or suspended when used, which is administered subcutaneously, intramuscularly, or directly administered to a body tissue such as blood vessel or an organ. The injectable includes a lyophilized injectable, a powder injectable, a filled syringe, a cartridge, an infusion, an embedded injectable, a long acting injectable, and the like, in addition to those generally referred to as injectables. In the production of the injectable, the following method (a), or (b) is usually used:

(a) A homogeneous solution is prepared by dissolving, suspending, or emulsifying the active ingredient as it is or a mixture obtained by adding an additive to the active ingredient, in water for injection, another aqueous solvent, a non-aqueous solvent or the like. Then, the prepared solution is filled in a container for injection, and then the container is sealed, followed by sterilization; and (b) A homogeneous solution is prepared by dissolving, suspending, or emulsifying the active ingredient as it is or a mixture obtained by adding an additive to the active ingredient, in water for injection, another aqueous solvent, a non-aqueous solvent or the like. Then, the prepared solution is aseptically filtrated or aseptically prepared, the resulting solution is filled in a container for injection, and the container is sealed.

The lyophilized injectable can be usually produced by dissolving the active ingredient as it is or a mixture of the active ingredient and an additive such as an excipient, in water for injection, aseptically filtering the solution, filling the solution in a container for injection, and then lyophilizing the solution, or directly filling the solution in a container after lyophilizing the solution in a dedicated container. The powder injectable can be usually produced by crystallizing a powder subjected to aseptic filtration to prepare a powder, and if necessary, adding a sterilized additive to the prepared powder, and filling the powder in a container for injection. A filled syringe can be usually produced by preparing a solution, a suspension, or an emulsion with the active ingredient as it is or with the active ingredient and an additive, and then filling the prepared solution, suspension, or emulsion in a glass syringe. The cartridge refers to an injectable used by inserting a cartridge filled with a drug solution into a dedicated syringe. The cartridge filled with the drug solution can be usually produced by preparing a solution, a suspension, or an emulsion with the active ingredient as it is or with the active ingredient and an additive, and filling the prepared solution, suspension, or emulsion into the cartridge. The infusion refers to 100 mL or more of injectable usually administered intravenously. The embedded injectable refers to a solid or gel-like injection which is applied subcutaneously, intramuscularly or the like by using an implantation tool or by surgery, for the purpose of releasing the active ingredient over a long period of time. The embedded injectable can be usually produced by using a biodegradable polymer compound and forming the compound into a pellet, microsphere, or gel. The long acting injectable refers to an injectable which is applied intramuscularly or the like for the purpose of releasing the active ingredient over a long period of time. The sustained injectable can be usually produced by dissolving or suspending the active ingredient in a vegetable oil or the like, or preparing a microsphere suspension containing a biodegradable polymer compound.

The compound of the present disclosure may also be administered as a concomitant drug in combination with another drug for:

1) complementation and/or enhancement of the prophylactic and/or therapeutic effects of the compound;
2) improvement of kinetics and absorption, and reduction in dosage; and/or
3) attenuation of side effects of the compound.

With respect to a combination drug comprising the compound of the present invention and other drug, may be administered in the form of a blending drug in which both ingredients are blended in one preparation, or may be administered in the form of separate preparations. Administration in this separate preparations includes simultaneous administration and administration by time difference. In addition, administration by time difference may be performed by administering the compound of the present disclosure first and then administering another drug later, or by administering another drug first and then administering the compound of the present disclosure later. The administration methods of the drugs may be the same or different.

The disease for which the above combination drug has a prophylactic and/or therapeutic effect is not particularly limited as long as it is a disease for which the prophylactic and/or therapeutic effect of the compound of the present disclosure are complemented and/or enhanced.

Other drugs for complementing and/or enhancing the prophylactic and/or therapeutic effect of the compound of the present disclosure on pain include, for example, acetaminophen, non-steroidal anti-inflammatory drugs, opioid drugs, antidepressant drugs, antiepileptic drugs, N-methyl-D-aspartate antagonists, muscle relaxants, antiarrhythmic drugs, steroid drugs, and bisphosphonate drugs.

Examples of the non-steroidal anti-inflammatory drug include aspirin preparations such as sasapyrine, sodium salicylate, aspirin, and aspirin-dialuminate formulation, diflunisal, indomethacin, suprofen, ufenamate, dimethylisopropyl azulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napageln ointment, epirizole, tiaramide hydrochloride, tinolidine hydrochloride, emorfazone, sulpyrine, Migrenin, Saridon, Sedes G, Amipylo-N, solbone, a pyrine cold remedy, acetaminophen, phenacetin, dimetotiazine mesylate, meloxicam, celecoxib, rofecoxib, valdecoxib, a simetride blending drug, and a non-pyrine cold remedy.

Examples of the opioid drug include codeine, fentanyl, hydromorphone, levorphanol, meperidine, methadone, morphine, oxycodone, oxymorphone, propoxyphene, and tramadol.

Examples of the antidepressant drug include tricyclic antidepressant drugs (for example, amitriptyline hydrochloride, imipramine hydrochloride, clomipramine hydrochloride, dosulepin hydrochloride, nortriptyline hydrochloride, lofepramine hydrochloride, trimipramine maleate, and amoxapine), tetracyclic antidepressant drugs (for example, maprotiline hydrochloride, mianserin hydrochloride, and setiptiline maleate), monoamine oxidase (MAO) inhibitors (safrazine hydrochloride), serotonin and noradrenaline reuptake inhibitors (SNRI) (for example, milnacipran hydrochloride and venlafaxine hydrochloride), selective serotonin reuptake inhibitors (SSRI) (for example, fluvoxamine maleate, paroxetine hydrochloride, fluoxetine hydrochloride, and citalopram hydrochloride), and serotonin reuptake inhibitors (for example, trazodone hydrochloride).

Examples of the antiepileptic drug include phenobarbital, pridomine, phenytoin, ethosuximide, zonisamide, nitrazepam, clonazepam, carbamazepine, sodium valproate, acetazolamide, and sulthiame.

Examples of the N-methyl-D-aspartate antagonist include ketamine hydrochloride, amantadine hydrochloride, memantine hydrochloride, dextromethorphan, and methadone.

Examples of the muscle relaxant include succinylcholine, suxamethonium, vecuronium bromide, pancuronium bromide, and dantrolene sodium.

Examples of the antiarrhythmic drug include procainamide, disopyramide, cibenzoline, pirmenol, lidocaine, mexiletine, aprindine, pilsicainide, flecainide, propafenone, propranolol, atenolol, bisoprolol, amiodarone, sotalol, verapamil, diltiazem, and bepridil.

Examples of the steroid drug include, as an external medicine, clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, beclomethasone dipropionate, and fludroxycortide.

Examples of the internal medicine or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, and betamethasone.

Examples of the inhalant include beclomethasone dipropionate, fluticasone propionate, budesonide, flunisolide, triamcinolone, ST-126P, ciclesonide, dexamethasone palomithionate, mometasone furancarbonate, prasterone sulfonate, deflazacort, methylprednisolone suleptanate, and methylprednisolone sodium succinate.

Examples of the bisphosphonate drug include etidronate, pamidronate, alendronate, risedronate, zoledronate, and minodronate.

Any two or more of the other drugs may be administered in combination.

In addition, other drugs that complement and/or enhance the prophylactic and/or therapeutic effect of the compound of the present disclosure include not only those that have been found to date but also those that will be found in the future based on the mechanism described above.

Unless defined otherwise, all technical, scientific terms, and abbreviations used herein have the same meaning as commonly understood by one of ordinary skill in the art to which this invention belongs.

In addition, in the present specification, all contents of all patent documents and non-patent documents or references explicitly cited may be cited herein as part of the present specification.

In one aspect, the present disclosure provides the following embodiments.

[1] A compound represented by general formula (I-A) or a pharmaceutically acceptable salt thereof:

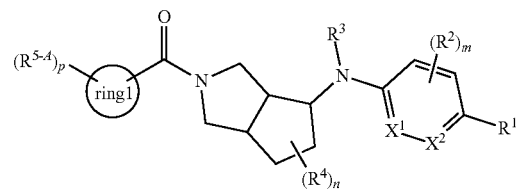

(I-A)

wherein $X^1$ and $X^2$ each independently represent (1) CH, (2) $CR^X$, or (3) N, provided that at least one of $X^1$ and $X^2$ represents N, $R^1$ represents a halogen atom,
$R^X$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group,
$R^2$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group,
when m is 2 or more, a plurality of $R^2$s may be the same or different,
$R^3$ represents (1) a hydrogen atom, (2) a C1-6 alkyl group, (3) a C1-6 haloalkyl group, (4) a 3- to 10-membered cyclic group, (5) —(C1-6 alkylene)-(3- to 10-membered cyclic group), (6) —(C1-6 haloalkylene)-(3- to 10-membered cyclic group), wherein one to two carbon atoms in the C1-6 alkyl group, the C1-6 haloalkyl group, the C1-6 alkylene, and the C1-6 haloalkylene may be replaced with an oxygen atom or an optionally oxidized sulfur atom,
the 3- to 10-membered cyclic group in $R^3$ may be substituted with one to five $R^{301}$s,
$R^{301}$ represents (1) a halogen atom, (2) a C1-4 alkyl group, (3) a C1-4 alkoxy group, (4) a C1-4 haloalkyl group, (5) a C1-4 haloalkoxy group, (6) COOR$^{302}$, (7) CONR$^{303}$R$^{304}$, (8) a C3-6 cycloalkyl group, (9) a hydroxyl group, (10) a nitro group, (11) a cyano group, (12) —NR$^{305}$R$^{306}$, (13) —SR$^{307}$, (14) —SOR$^{308}$, (15) —SO$_2$R$^{309}$, or (16) an oxo group,
when two or more $R^{301}$s are substituted, a plurality of $R^{301}$s may be the same or different,
$R^{302}$, $R^{303}$, $R^{304}$, $R^{305}$, $R^{306}$, $R^{307}$, $R^{308}$, or $R^{309}$ each independently represent (1) a hydrogen atom or (2) a C1-4 alkyl group,
when $R^2$ represents (2) to (9) in $R^2$, and $R^3$ represents a C1-6 alkyl group, $R^2$ and $R^3$, together with an atom to which $R^2$ and $R^3$ are bonded, may form a 5- to 6-membered cyclic group,
$R^4$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, or (9) a C1-6 haloalkoxy group,
when n is 2 or more, a plurality of $R^4$s may be the same or different,
when two $R^4$s present on the same carbon atom represent a C1-6 alkyl group, the two $R^4$s, together with a carbon atom to which the two $R^4$s are bonded, may form a C3-6 cycloalkyl group,
ring 1 represents a 3- to 15-membered cyclic group,
$R^{5-A}$ represents (1) a halogen atom, (2) a C1-6 alkyl group, (3) a C2-6 alkenyl group, (4) a C2-6 alkynyl group, (5) a C1-6 alkoxy group, (6) a C1-6 alkylthio group, (7) a C1-6 alkylsulfinyl group, (8) a C1-6 alkylsulfonyl group, (9) a C2-6 acyl group, (10) a 3- to 6-membered cyclic group, (11) -L$^{R5}$-(3- to 6-membered cyclic group), (12) a hydroxyl group, (13) a nitro group, (14) a cyano group, (15) an oxo group, (16) —NR$^{501}$R$^{502}$, (17) —COOR$^{503}$, (18) —CONR$^{504}$R$^{505}$, or (19) —SO$_2$NR$^{506}$R$^{507}$, wherein one to two carbon atoms in the C1-6 alkyl group, the C2-6 alkenyl group, the C2-6 alkynyl group, the C1-6 alkoxy group, the C1-6 alkylthio group, the C1-6 alkylsulfinyl group, the C1-6 alkylsulfonyl group, and the C2-6 acyl group may be replaced with an oxygen atom or an optionally oxidized sulfur atom,
when p is 2 or more, a plurality of $R^{5-A}$s may be the same or different,
the groups (2) to (11) in $R^{5-A}$ may be substituted with one to nine $R^{508}$s,
$R^{508}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —NR$^{509}$R$^{510}$,
when two or more $R^{508}$s are substituted, a plurality of $R^{508}$s may be the same or different,
$L^{R5}$ represents (1) —O—, (2) —(C1-4 alkylene)-, (3) —O—(C1-4 alkylene)-, (4) —(C1-4 alkylene)-O—, (5) —NR$^{511}$—, or (6) —SO$_{0-2}$—,
$R^{501}$, $R^{502}$, $R^{503}$, $R^{504}$, $R^{505}$, $R^{506}$, $R^{507}$, $R^{509}$, $R^{510}$, or $R^{511}$ each independently represent (1) a hydrogen atom, (2) a C1-6 alkyl group, (3) a C2-6 acyl group, or (4) a C1-6 alkylsulfonyl group,
m represents an integer of 0 to 2,
n represents an integer of 0 to 5, and
p represents an integer of 0 to 5.

[2] A compound represented by general formula (I) or a pharmaceutically acceptable salt thereof:

wherein
$X^1$ and $X^2$ each independently represent (1) CH, (2) CR$^X$, or (3) N, provided that at least one of $X^1$ and $X^2$ represents N,
$R^1$ represents a halogen atom,
$R^X$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group,
$R^2$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, (9) a C1-6 haloalkoxy group, or (10) a cyano group,
when m is 2 or more, a plurality of $R^2$s may be the same or different,
$R^3$ represents (1) a hydrogen atom, (2) a C1-6 alkyl group, (3) a C1-6 haloalkyl group, (4) a 3- to 10-membered cyclic group, (5) —(C1-6 alkylene)-(3- to 10-membered cyclic group), (6) —(C1-6 haloalkylene)-(3- to 10-membered cyclic group), wherein one to two carbon atoms in the C1-6 alkyl group, the C1-6 haloalkyl group, the C1-6 alkylene, and the C1-6 haloalkylene may be replaced with an oxygen atom or an optionally oxidized sulfur atom,
the 3- to 10-membered cyclic group in $R^3$ may be substituted with one to five $R^{301}$s,
$R^{301}$ represents (1) a halogen atom, (2) a C1-4 alkyl group, (3) a C1-4 alkoxy group, (4) a C1-4 haloalkyl group, (5) a C1-4 haloalkoxy group, (6) COOR$^{302}$, (7) CONR$^{303}$R$^{304}$, (8) a C3-6 cycloalkyl group, (9) a hydroxyl group, (10) a nitro group, (11) a cyano group, (12) —NR$^{305}$R$^{306}$, (13) —SR$^{307}$, (14) —SOR$^{308}$, (15) —SO$_2$R$^{309}$, or (16) an oxo group, when two or more R$^{301}$s are substituted, a plurality of R$^{301}$s may be the same or different, R$^{302}$, R$^{303}$, R$^{304}$, R$^{305}$, R$^{306}$, R$^{307}$, R$^{308}$, or R$^{309}$ each independently represent (1) a hydrogen atom or (2) a C1-4 alkyl group, when R$^2$ represents (2) to (9) in R$^2$, and R$^3$ represents a C1-6 alkyl group, R$^2$ and R$^3$, together with an atom to which R$^2$ and R$^3$ are bonded, may form a 5- to 6-membered cyclic group, R$^4$ represents (1) a halogen atom, (2) a C1-6 alkyl group, (3) a C2-6 alkenyl group, (4) a C2-6 alkynyl group, (5) a C1-6 alkoxy group, (6) a C1-6 haloalkyl group, (7) a C2-6 haloalkenyl group, (8) a C2-6 haloalkynyl group, or (9) a C1-6 haloalkoxy group, when n is 2 or more, a plurality of R$^4$s may be the same or different, when two R$^4$s present on the same carbon atom represent a C1-6 alkyl group, the two R$^4$s, together with a carbon atom to which the two R$^4$s are bonded, may form a C3-6 cycloalkyl group, ring 1 represents a 3- to 15-membered cyclic group, R$^5$ represents (1) a halogen atom, (2) a C1-6 alkyl group, (3) a C2-6 alkenyl group, (4) a C2-6 alkynyl group, (5) a C1-6 alkoxy group, (6) a C1-6 alkylthio group, (7) a C1-6 alkylsulfinyl group, (8) a C1-6 alkylsulfonyl group, (9) a C2-6 acyl group, (10) a 3- to 6-membered cyclic group, (11) -L$^{R5}$-(3- to 6-membered cyclic group), (12) a hydroxyl group, (13) a nitro group, (14) a cyano group, (15) an oxo group, (16) —NR$^{501}$R$^{502}$, (17) —COOR$^{503}$, (18) —CONR$^{504}$R$^{505}$, or (19) —SO$_2$NR$^{506}$R$^{507}$, when p is two or more, a plurality of R$^5$s may be the same or different, the groups (2) to (11) in R$^5$ may be substituted with one to nine R$^{508}$s, R$^{508}$ represents (1) a halogen atom, (2) a C1-4 alkyl group, (3) a C1-4 alkoxy group, (4) a C2-6 acyl group, (5) a C3-6 cycloalkyl group, (6) a hydroxyl group, or (7) —NR$^{509}$R$^{510}$, when two or more R$^{508}$s are substituted, a plurality of R$^{508}$s may be the same or different, L$^{R5}$ represents (1) —O—, (2) —(C1-4 alkylene)-, (3) —O—(C1-4 alkylene)-, (4) —(C1-4 alkylene)-O—, (5) —NR$^{511}$—, or (6) —SO$_{0-2}$—, R$^{501}$, R$^{502}$, R$^{503}$, R$^{504}$, R$^{505}$, R$^{506}$, R$^{507}$, R$^{509}$, R$^{510}$, or R$^{511}$ each independently represent (1) a hydrogen atom, (2) a C1-6 alkyl group, (3) a C2-6 acyl group, or (4) a C1-6 alkylsulfonyl group, m represents an integer of 0 to 2, n represents an integer of 0 to 5, and p represents an integer of 0 to 5.

[3] The compound or the pharmaceutically acceptable salt thereof according to the above [1] or [2], wherein ring 1 is a 3- to 10-membered cyclic group, or

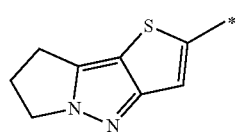

wherein the * mark represents a bonding position with a carbonyl group.

[4] The compound or the pharmaceutically acceptable salt thereof according to the above [1] or [3], wherein ring 1 represents a ring structure selected from the group consisting of the following ring structures;

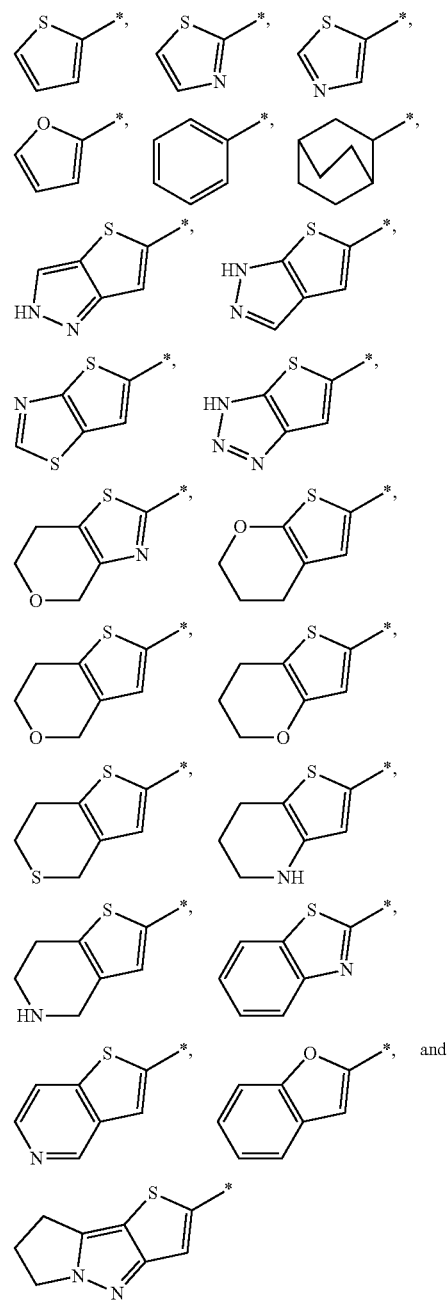

wherein the * mark represents a bonding position with a carbonyl group, and a hydrogen atom represented by NH may be replaced with R$^{5-4}$.

[5] The compound or the pharmaceutically acceptable salt thereof according to the above [2] or [3], wherein ring 1 represents a ring structure selected from the group consisting of the following ring structures;

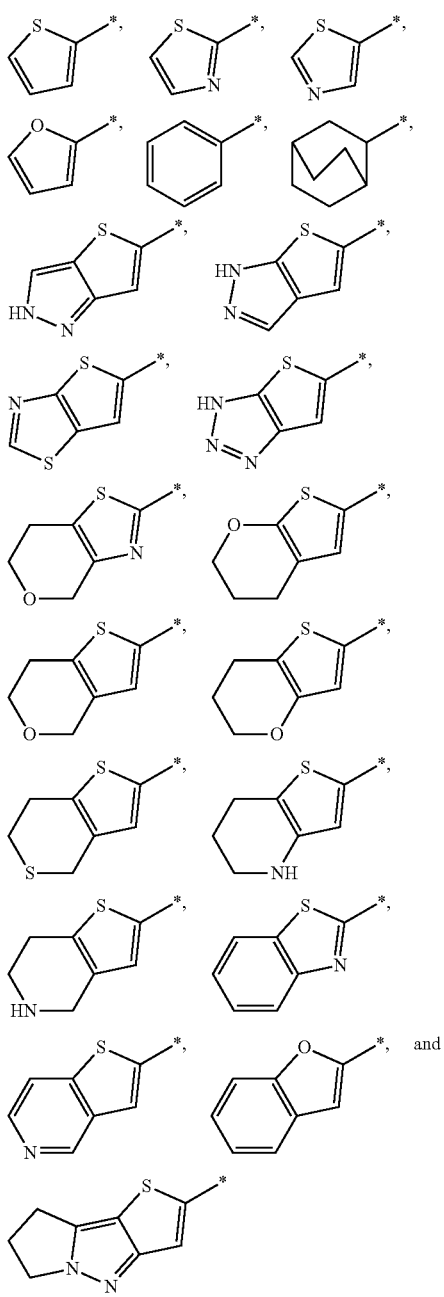

wherein the * mark represents a bonding position with a carbonyl group, and a hydrogen atom represented by NH may be replaced with $R^5$.

[6] The compound or the pharmaceutically acceptable salt thereof according to any one of the above [1] to [5], wherein ring 1 represents a ring structure selected from the group consisting of the following ring structures

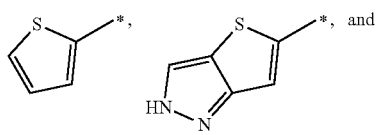

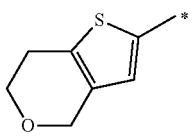

wherein the * mark represents a bonding position with a carbonyl group, and a hydrogen atom represented by NH may be replaced with $R^{5-A}$ or $R^5$.

[7] The compound or the pharmaceutically acceptable salt thereof according to any one of the above [1] to [6], wherein $R^{5-A}$ or $R^5$ is (1) a halogen atom, (2) a C1-6 alkyl group, (3) a C1-6 alkoxy group, (4) a C1-6 haloalkyl group, (5) a C1-6 haloalkoxy group, (6) a 3- to 6-membered cyclic group, (7) an oxo group, (8) —$NR^{501}R^{502}$, or (9) —$COOR^{503}$.

[8] The compound or the pharmaceutically acceptable salt thereof according to any one of the above [1] to [7], wherein $R^{5-A}$ or $R^5$ is (1) a C1-6 alkyl group, (2) a C1-6 alkoxy group, (3) a C1-6 haloalkyl group, (4) a C1-6 haloalkoxy group, (5) a cyclopropyl group, (6) a furan ring, (7) an N-methylpyrazole ring, (8) an oxo group, (9) a dimethylamino group, or (10) —$COOCH_3$.

[9] The compound or the pharmaceutically acceptable salt thereof according to any one of the above [1] to [8], wherein $R^3$ is (1) a hydrogen atom, (2) a C1-6 alkyl group, (3) a C1-6 haloalkyl group, (4) a 3- to 10-membered cyclic group, or (5) —$CH_2$-(3- to 10-membered cyclic group).

[10] The compound or the pharmaceutically acceptable salt thereof according to any one of the above [1] to [9], wherein $R^3$ represents (1) a hydrogen atom, (2) a C1-6 alkyl group, (3) a C1-6 haloalkyl group, (4) a cyclopropyl group, or (5) —$CH_2$-Q, and Q is (1) benzene, (2) pyridine, or (3) imidazo[2,1-b]thiazole.

[11] The compound or the pharmaceutically acceptable salt thereof according to any one of the above [1] to [10], wherein $X^1$ and $X^2$ are both N.

[12] The compound or the pharmaceutically acceptable salt thereof according to any one of the above [1] to [11], wherein the compound represented by general formula (I-A) or general formula (I) is a compound represented by general formula (I-1):

(I-1)

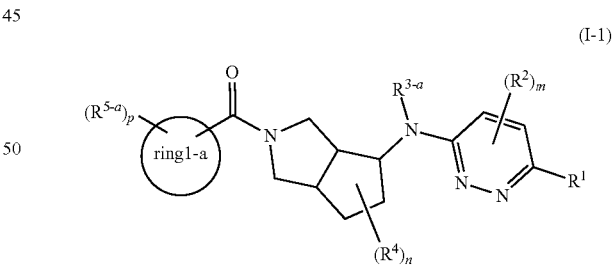

wherein $R^{3-a}$ represents (1) a hydrogen atom, (2) a C1-6 alkyl group, (3) a C1-6 haloalkyl group, (4) a cyclopropyl group, or (5) —$CH_2$-Q, ring 1-a represents a ring structure selected from the group consisting of the following ring structures;

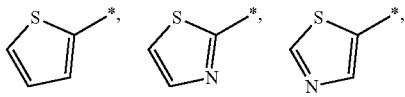

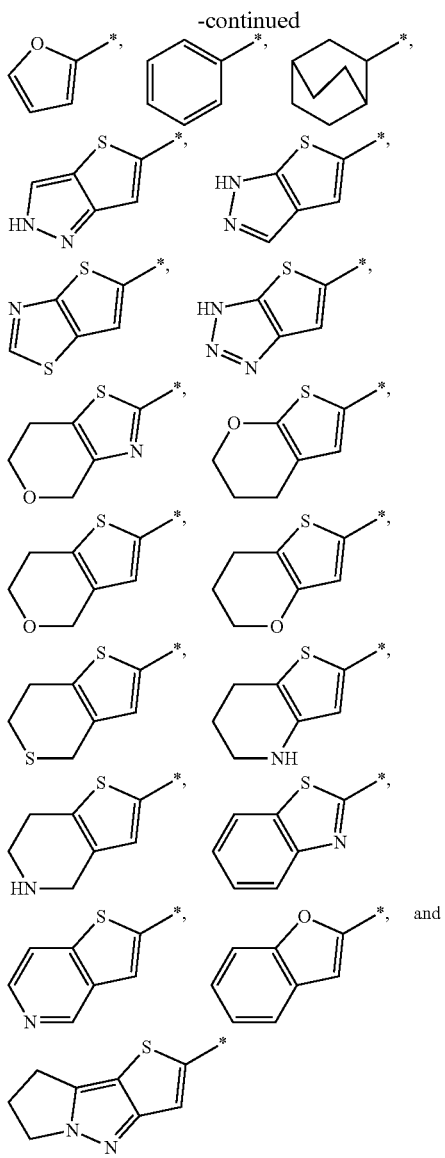

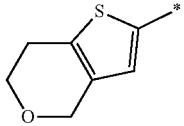

wherein the * mark represents a bonding position with a carbonyl group, and a hydrogen atom represented by NH may be replaced with R$^{5-a}$.

[14] The compound or the pharmaceutically acceptable salt thereof according to the above [1] or [2], wherein the compound represented by general formula (I-A) or general formula (I) is a compound selected from the group consisting of:

(1) {(3aS,4R,6aR)-4-[(6-chloro-3-pyridazinyl)amino]hexahydrocyclopenta[c]pyrrol-2(1H)-yl}[5-(difluoromethyl)-2-thienyl]methanone, (2) {(3aS,4R,6aR)-4-[(6-chloro-3-pyridazinyl)amino]hexahydrocyclopenta[c]pyrrol-2(1H)-yl}(5-methyl-2-thienyl)methanone, (3) [(3aS,4R,6aR)-4-[(6-chloro-3-pyridazinyl)amino]hexahydrocyclopenta[c]pyrrol-2(1H)-yl](6,7-dihydro-4H-thieno[3,2-c]pyran-2-yl)methanone, (4) [(3aS,4R,6aR)-4-[(6-bromo-3-pyridazinyl)amino]hexahydrocyclopenta[c]pyrrol-2(1H)-yl](5-methyl-2-thienyl)methanone, (5) [(3aS,4R,6aR)-4-[(6-bromo-3-pyridazinyl)amino]hexahydrocyclopenta[c]pyrrol-2(1H)-yl](6,7-dihydro-4H-thieno[3,2-c]pyran-2-yl)methanone, (6) [(3aS,4R,6aR)-4-[(6-bromo-3-pyridazinyl)amino]hexahydrocyclopenta[c]pyrrol-2(1H)-yl](2-methyl-2H-thieno[3,2-c]pyrazol-5-yl)methanone, (7) [(3aS,4R,6aR)-4-[benzyl(6-bromo-3-pyridazinyl)amino]hexahydrocyclopenta[c]pyrrol-2(1H)-yl](5-methyl-2-thienyl)methanone, (8) rel-6-chloro-3-({(3aS,4R,6aR)-2-[(5-methyl-2-thienyl)carbonyl]octahydrocyclopenta[c]pyrrol-4-yl}amino)-4-pyridazinecarbonitrile, (9) {(3aR,4R,6aS)-4-[(6-chloro-3-pyridazinyl)amino]-3a-fluorohexahydrocyclopenta[c]pyrrol-2(1H)-yl}(6,7-dihydro-4H-thieno[3,2-c]pyran-2-yl)methanone, and

(10) [(3aR,6R,6aS)-6-[(6-bromo-3-pyridazinyl)amino]-4,4-difluorohexahydrocyclopenta[c]pyrrol-2(1H)-yl],(6,7-dihydro-4H-thieno[3,2-c]pyran-2-yl)methanone.

[15] The compound or the pharmaceutically acceptable salt thereof according to the above [1] or [2], wherein the compound represented by general formula (I-A) or general formula (I) is a compound selected from the group consisting of:

(1) [(3aS,4R,6aR)-4-[(6-bromo-3-pyridazinyl)(methyl)amino]hexahydrocyclopenta[c]pyrrol-2(1H)-yl](5-methyl-2-thienyl)methanone, (2) [(3aS,4R,6aR)-4-[(6-bromo-3-pyridazinyl)(methyl)amino]hexahydrocyclopenta[c]pyrrol-2(1H)-yl]{5-[2-(2-fluoroethoxy)ethyl]-2-thienyl}methanone, (3) [(3aS,4R,6aR)-4-[(6-bromo-3-pyridazinyl)(methyl)amino]hexahydrocyclopenta[c]pyrrol-2(1H)-yl][5-(2-fluoroethoxy)-2-thienyl]methanone, and (4) [(3aS,4R,6aR)-4-{(6-bromo-3-pyridazinyl)[2-(2-fluoroethoxy)ethyl]amino}hexahydrocyclopenta[c]pyrrol-2(1H)-yl](5-methyl-2-thienyl)methanone.

[16] A pharmaceutical composition containing the compound or the pharmaceutically acceptable salt thereof according to any one of the above [1] to [15] as an active ingredient, and a pharmaceutically acceptable carrier.

wherein the * mark represents a bonding position with a carbonyl group, and a hydrogen atom represented by NH may be replaced with R$^{5-a}$, R$^{5-a}$ represents (1) a C1-6 alkyl group, (2) a C1-6 alkoxy group, (3) a C1-6 haloalkyl group, (4) a C1-6 haloalkoxy group, (5) a cyclopropyl group, (6) a furan ring, (7) an N-methylpyrazole ring, (8) an oxo group, (9) a dimethylamino group, or (10) —COOCH$_3$, and other symbols represent the same meaning as the symbols described in the above [1], [2], or [10].

[13] The compound or the pharmaceutically acceptable salt thereof according to the above [12], wherein ring 1-a represents a ring structure selected from the group consisting of the following ring structures;

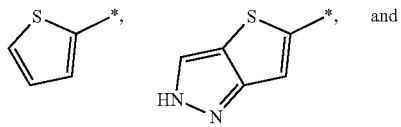

[17] The pharmaceutical composition according to the above [16], which is an ABHD6 inhibitor.

[18] The pharmaceutical composition according to the above [16] or [17], which is an agent for treating and/or preventing a disease associated with ABHD6.

[19] The pharmaceutical composition according to the above [18], wherein the disease associated with ABHD6 is pain, a neurological disease, an inflammatory disease, an autoimmune disease, a metabolic disease, or a malignant tumor.

[20] The pharmaceutical composition according to the above [18] or [19], wherein the disease associated with ABHD6 is pain, and the pain is pain associated with osteoarthritis, cancer pain, pain associated with chemotherapy, chronic low back pain, low back pain associated with osteoporosis, fracture pain, pain associated with rheumatoid arthritis, neuropathic pain, post-herpetic pain, pain associated with diabetic neuropathy, pain associated with fibromyalgia, pain associated with pancreatitis, pain associated with interstitial cystitis or bladder pain syndrome, pain associated with endometriosis, pain associated with irritable bowel syndrome, migraine, or pain associated with pulpitis.

[21] The pharmaceutical composition according to any one of the above [16] to [20], wherein the pharmaceutical composition is administered in combination with one or more selected from the group consisting of acetaminophen, non-steroidal anti-inflammatory drugs, opioid drugs, antidepressant drugs, antiepileptic drugs, N-methyl-D-aspartate antagonists, muscle relaxants, antiarrhythmic drugs, steroid drugs, and bisphosphonate drugs.

[22] An agent for treating and/or preventing a disease associated with ABHD6, containing the compound or the pharmaceutically acceptable salt thereof according to any one of the above [1] to [15].

[23] A method for preventing and/or treating a disease associated with ABHD6, the method including administering the compound or the pharmaceutically acceptable salt thereof according to any one of the above [1] to [15], or the pharmaceutical composition according to the above [16] or [17] to a patient in need of prevention and/or treatment of a disease associated with ABHD6.

[24] A compound or a pharmaceutically acceptable salt thereof according to any one of the above [1] to [15], for use in preventing and/or treating a disease associated with ABHD6.

[25] Use of the compound or the pharmaceutically acceptable salt thereof according to any one of the above [1] to [15], in the manufacture of an agent for preventing and/or treating a disease associated with ABHD6.

SYNTHESIS EXAMPLES

The solvent in parentheses shown in the description of the separation by chromatography and TLC indicates an eluting solvent or developing solvent used therefor, and the ratio represents the volume ratio.

The solvent in parentheses shown in the description of NMR indicates the solvent used for the measurement.

The compound names used in the present specification are named using a computer program ACD/Name (registered trademark), which generally performs naming according to the IUPAC nomenclature, or using a Chemdraw Ultra (Version 12.0, manufactured by Cambridge Soft), or according to the IUPAC nomenclature.

LC-MS/ELSD was performed under the following TFA conditions or formic acid conditions.

TFA conditions;

Column: YMC Triart $C_{18}$ (particle size: $1.9 \times 10^{-6}$ m; Column length: 30×2.0 mm I.D.); Flow rate: 1.0 mL/min; Column temperature: 30° C.; Mobile phase (A): 0.1% aqueous trifluoroacetic acid solution; Mobile phase (B): 0.1% trifluoroacetic acid-acetonitrile solution; Gradient (ratio of mobile phase (A): mobile phase (B)): [0 min] 95:5; [0.1 min] 95:5; [1.2 min] 5:95; [1.6 min] 5:95; Detector: UV (PDA), ELSD, MS.

Formic acid conditions;

Column: YMC Triart $C_{18}$ (particle size: $1.9 \times 10^{-6}$ m; Column length: 30×2.0 mm I.D.); Flow rate: 1.0 mL/min; Column temperature: 30° C.; Mobile phase (A): 0.1% aqueous formic acid solution; Mobile phase (B): 0.1% formic acid-acetonitrile solution; Gradient (ratio of mobile phase (A): mobile phase (B)): [0 min] 95:5; [0.1 min] 95:5; [1.2 min] 5:95; [1.6 min] 5:95; Detector: UV (PDA), ELSD, MS.

The HPLC retention time indicates the retention time under the conditions described in the LC-MS/ELSD if not stated otherwise. The description in parentheses shown in the HPLC retention time indicates the measurement conditions.

Reference Example 1: 2-Benzylhexahydrocyclopenta[c]pyrrol-4(1H)-one

To a dichloromethane solution (600 mL) of N-benzyl-N-(methoxymethyl)-N-trimethylsilylmethylamine (CAS No.: 93102-05-7, 50 g), were added 2-cyclopentenone (CAS No.: 930-30-3, 17 g) and trifluoroacetic acid (CAS No.: 76-05-1, 240 mg), and the mixture was stirred at room temperature for 16 hours. Triethylamine (430 mg) was added to the reaction solution, and the mixture was concentrated under reduced pressure. The resulting residue was purified by silica gel column chromatography to obtain the title compound (30 g).

HPLC retention time (min): 0.65 (TFA);
MS (ESI, Pos.): 226 (M+H)+.

Reference Example 2: (R)—N-((3aS, 6aR, E)-2-Benzylhexahydrocyclopenta[c]pyrrol-4(1H)-ylidene)-2-methylpropane-2-sulfinamide Titanium(IV) ethoxide (CAS No.: 3037-36-3, 46.6 g) and (R)-(+)-2-methyl-2-propanesulfinamide (CAS No.: 196929-78-9, 11.8 g) were added to a solution of the compound (20 g) prepared in Reference Example 1 in THF (300 mL), and the mixture was stirred at 60° C. for 15 hours. The reaction solution was slowly poured into a saturated aqueous sodium bicarbonate solution and dichloromethane, and filtered. The mixture was washed with saturated saline, dried over anhydrous sodium sulfate, and concentrated under reduced pressure. The resulting residue was purified by silica gel column chromatography to obtain the title compound (12.4 g).

HPLC retention time (min): 0.80 (TFA);
MS (ESI, Pos.): 319 (M+H)+.

Reference Example 3: (3aS, 6aR)-2-Benzylhexahydrocyclopenta[c]pyrrol-4(1H)-one

To a solution of the compound (20 g) prepared in Reference Example 2 in THF (60 mL), was added 2 N hydrochloric acid (60 mL), and the mixture was stirred at room temperature for 1 hour. The reaction solution was neutralized with 2 N sodium hydroxide, followed by extraction with dichloromethane. The organic layer was washed with saturated saline, dried over anhydrous sodium sulfate, and concentrated under reduced pressure. The obtained title compound was used for the next reaction without purification.

Reference Example 4: 2-Methyl-2-propanyl (3aS, 6aR)-4-oxohexahydrocyclopenta[c]pyrrole-2(1H)-carboxylate Di-tert-butyl dicarbonate (CAS No.: 24424-99-5, 9.4 g) and 20% palladium hydroxide (CAS No.: 12135-22-7, 700 mg) were added to a solution of the compound prepared in Reference Example 3 in THE (60 mL), and the mixture was stirred under a hydrogen atmosphere at room temperature for 15 hours. The reaction solution was filtered and concentrated under reduced pressure. The resulting residue was purified by silica gel column chromatography to obtain the title compound (7.0 g).
$^1$H-NMR (CD$_3$OD): δ 3.66-3.53, 3.14, 3.06-2.98, 2.76-2.71, 2.39-2.35, 2.21-2.12, 1.87 1.45.

Reference Example 5: 2-Methyl-2-propanyl (3aS, 4S, 6aR)-4-hydroxyhexahydrocyclopenta[c]pyrrole-2(1H)-carboxylate A 1 M lithium tri-sec-butylborohydride THF solution (CAS No.: 38721-52-7, 49 mL) was added to a solution of the compound (7.3 g) prepared in Reference Example 4 in THE (200 mL) at −78° C., and the mixture was stirred at −78° C. for 1 hour. A 35% aqueous hydrogen peroxide solution was slowly added to the reaction solution at 0° C. until foaming stopped, followed by extraction with dichloromethane. The organic layer was washed with saturated saline, dried over anhydrous sodium sulfate, and concentrated under reduced pressure. The resulting residue was purified by silica gel column chromatography to obtain the title compound (6.5 g).
$^1$H-NMR (CDCl$_3$): δ 4.30-4.25, 3.63-3.50, 3.38-3.30, 3.17-3.15, 2.67, 1.90-1.73, 1.73-1.54, 1.47.

Reference Example 6: 2-Methyl-2-propanyl (3aS, 4S, 6aR)-4-{[(4-methylphenyl)sulfonyl]oxy}hexahydrocyclopenta[c]pyrrole-2(1H)-carboxylate Triethylamine (12 mL), p-toluenesulfonyl chloride (CAS No.: 98-59-9, 8.2 g), and trimethylamine hydrochloride (CAS No.: 75-50-3, 820 mg) were added to a solution of the compound (6.5 g) prepared in Reference Example 5 in dichloromethane (100 mL), and the mixture was stirred at room temperature for 6 hours. A saturated aqueous sodium bicarbonate solution was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (9.3 g).
HPLC retention time (min): 1.2 (TFA);
MS (ESI, Pos.): 382 (M+H)$^+$.

Reference Example 7: 2-Methyl-2-propanyl (3aS, 4R,6aR)-4-azidohexahydrocyclopenta[c]pyrrole-2(1H)-carboxylate Sodium azide (CAS No.: 26628-22-8, 3.2 g) was added to a solution of the compound (9.3 g) prepared in Reference Example 6 in dimethyl sulfoxide (72 mL), and the mixture was stirred at 60° C. for 6 hours. Water was added to the reaction solution, followed by extraction with dichloromethane. The organic layer was washed with saturated saline, dried over anhydrous sodium sulfate, concentrated under reduced pressure, and used for the next reaction without purification.

Reference Example 8: 2-Methyl-2-propanyl (3aS, 4R,6aR)-4-aminohexahydrocyclopenta[c]pyrrole-2(1H)-carboxylate To a solution of the compound (6.5 g) prepared in Reference Example 7 in ethanol (240 mL), was added 20% palladium hydroxide (930 mg), and the mixture was stirred under a hydrogen atmosphere at room temperature for 15 hours. The reaction solution was filtered and concentrated under reduced pressure. The resulting residue was purified by silica gel column chromatography to obtain the title compound (4.5 g).
HPLC retention time (min): 0.77 (TFA);
MS (ESI, Pos.): 227 (M+H)$^+$.

Reference Example 9: 2-Methyl-2-propanyl (3aS, 4R,6aR)-4-[(6-chloro-3-pyridazinyl)amino]hexahydrocyclopenta[c]pyrrole-2(1H)-carboxylate N,N-diisopropylethylamine (hereinafter, DIPEA) (6.9 mL) and 3,6-dichloropyridazine (CAS No.: 141-30-0, 1.5 g) were added to a solution of the compound (1.5 g) prepared in Reference Example 8 in N,N-dimethylacetamide (hereinafter, DMA) (25 mL), and the mixture was stirred at 160° C. for 1 hour. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (1.5 g).
HPLC retention time (min): 0.89 (formic acid);
MS (ESI, Pos.): 339 (M+H)$^+$.

Reference Example 10: (3aS,4R,6aR)—N-(6-Chloro-3-pyridazinyl)octahydrocyclopenta[c]pyrrole-4-amine dihydrochloride To the compound (1.2 g) prepared in Reference Example 9, was added 4 N hydrochloric acid (1,4 dioxane solution, 12 mL), and the mixture was stirred at room temperature for 1 hour. The reaction solution was concentrated under reduced pressure to obtain the title compound (1.0 g).
HPLC retention time (min): 0.59 (formic acid);
MS (ESI, Pos.): 239 (M+H)$^+$.

Reference Example 10-1: rel-(3aS,4R,6aR)—N-(6-Chloro-3-pyridazinyl)octahydrocyclopenta[c]pyrrole-4-amine dihydrochloride racemic mixture The same procedures as in Reference Example 4→Reference Example 5→Reference Example 6→Reference Example 7→Reference Example 8→Reference Example 9→Reference Example 10 were carried out using the compound prepared in Reference Example 1 in place of the compound prepared in Reference Example 3 to obtain the title compound.

Example 1: {(3aS,4R,6aR)-4-[(6-Chloro-3-pyridazinyl)amino]hexahydrocyclopenta[c]pyrrol-2(1H)-yl}[5-(difluoromethyl)-2-thienyl]methanone

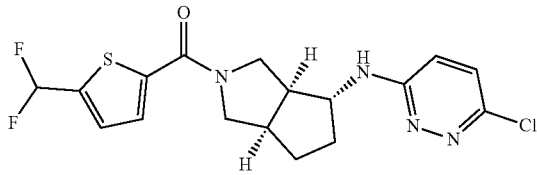 [SMILES: O=C(c1ccc(C(F)F)s1)N1C[C@@H]2CC[C@@H](Nc3ccc(Cl)nn3)[C@@H]2C1]

DIPEA (0.083 mL), 5-(difluoromethyl)thiophene-2-carboxylic acid (CAS No.: 189330-23-2, 19 mg), and O-(7-azabenzotriazol-1-yl)-N,N,N',N'-tetramethyluronium hexafluorophosphate (hereinafter, HATU) (CAS No.: 148893-10-1, 38 mg) were added to a solution of the compound (30 mg) prepared in Reference Example 10 in DMA (0.5 mL), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (32 mg).

HPLC retention time (min): 0.88 (TFA);
MS (ESI, Pos.): 399 (M+H)$^+$;
$^1$H-NMR (CDCl$_3$): δ 7.43, 7.18, 6.83, 6.63, 4.78-4.52, 4.12, 3.88, 3.67, 3.49, 2.99-2.80, 2.79-2.61, 2.36, 2.13, 1.69-1.57.

Examples 1-1 to 1-6

The same procedure as in Example 1 was carried out using a corresponding carboxylic acid compound in place of 5-(difluoromethyl)thiophene-2-carboxylic acid, and using the compound prepared in Reference Example 10 or the compound prepared in Reference Example 10-1 in place of the compound prepared in Reference Example 10 to obtain each of the title compounds.

Example 1-1: rel-1,3-Benzothiazol-2-yl{(3aS,4R,6aR)-4-[(6-chloro-3-pyridazinyl)amino]hexahydrocyclopenta[c]pyrrol-2(1H)-yl}methanone racemic mixture

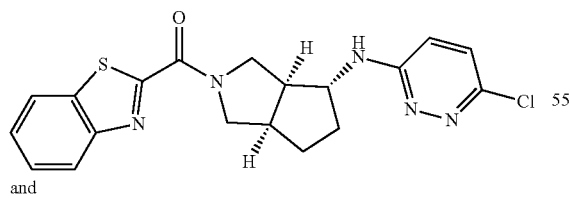

and

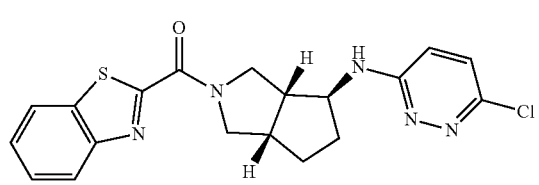

HPLC retention time (min): 1.10 (formic acid);
MS (ESI, Pos.): 400 (M+H)$^+$;
$^1$H-NMR (DMSO-d$_6$): δ 8.23-8.14, 7.64-7.55, 7.42-7.30, 6.92, 4.44-4.27, 4.14-4.07, 4.24-4.03, 3.93-3.81, 3.78-3.66, 3.55-3.47, 3.35-3.24, 3.23-3.05, 3.00-2.70, 2.61-2.54, 2.26-2.16, 2.13-1.97, 1.66-1.49.

Example 1-2: {(3aS,4R,6aR)-4-[(6-Chloro-3-pyridazinyl)amino]hexahydrocyclopenta[c]pyrrol-2(1H)-yl}(5-methyl-2-thienyl)methanone

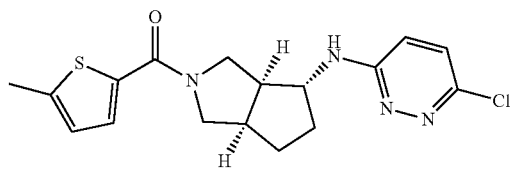 [SMILES: Cc1ccc(C(=O)N2C[C@@H]3CC[C@@H](Nc4ccc(Cl)nn4)[C@@H]3C2)s1]

HPLC retention time (min): 0.85 (TFA);
MS (ESI, Pos.): 363 (M+H)$^+$;
$^1$H-NMR (CDCl$_3$): δ 7.35-7.28, 7.16, 6.76-6.71, 6.65, 4.96, 4.14-3.96, 3.96-3.86, 3.82, 3.65, 2.88, 2.79-2.62, 2.50, 2.41-2.27, 2.18-2.04, 1.72-1.54.

Example 1-3: [(3aS,4R,6aR)-4-[(6-Chloro-3-pyridazinyl)amino]hexahydrocyclopenta[c]pyrrol-2(1H)-yl](thieno[3,2-c]pyridin-2-yl)methanone

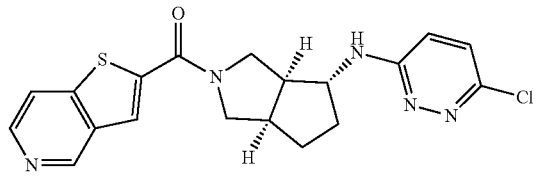 [SMILES: O=C(c1cc2cnccc2s1)N1C[C@@H]2CC[C@@H](Nc3ccc(Cl)nn3)[C@@H]2C1]

HPLC retention time (min): 0.74 (formic acid);
MS (ESI, Pos.): 400 (M+H)$^+$;
$^1$H-NMR (DMSO-d$_6$): δ 9.46-9.25, 8.63-8.43, 8.40-8.30, 8.29-8.14, 7.43-7.30, 6.97-6.83, 4.20-4.00, 3.99-3.65, 3.15-3.04, 3.04-2.79, 2.77-2.57, 2.27-2.15, 2.14-1.98, 1.70-1.58, 1.58-1.48.

Example 1-4: [(3aS,4R,6aR)-4-[(6-Chloro-3-pyridazinyl)amino]hexahydrocyclopenta[c]pyrrol-2(1H)-yl](6,7-dihydro-4H-thieno[3,2-c]pyran-2-yl)methanone

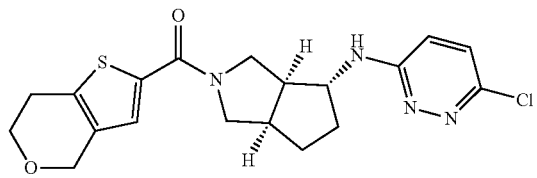 [SMILES: O=C(c1cc2c(s1)CCOC2)N1C[C@@H]2CC[C@@H](Nc3ccc(Cl)nn3)[C@@H]2C1]

HPLC retention time (min): 0.83 (TFA);
MS (ESI, Pos.): 405 (M+H)$^+$;

$^1$H-NMR (CDCl$_3$): δ 7.22-7.13, 6.66, 5.04, 4.76-4.65, 4.12, 3.98, 3.86, 3.64, 2.89, 2.70, 2.39-2.28, 2.17-2.07, 1.69-1.55.

Example 1-5: [(3aS,4R,6aR)-4-[(6-Chloro-3-pyridazinyl)amino]hexahydrocyclopenta[c]pyrrol-2(1H)-yl][4-(2-furyl)phenyl]methanone

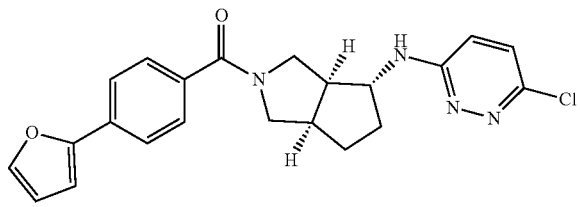 [SMILES: O=C(c1ccc(-c2ccco2)cc1)N1C[C@@H]2CC[C@@H](Nc3ccc(Cl)nn3)[C@@H]2C1]

HPLC retention time (min): 1.00 (formic acid);
MS (ESI, Pos.): 409 (M+H)$^+$;
$^1$H-NMR (DMSO-d$_6$): δ 8.14-8.07, 8.07-7.93, 7.73-7.47, 7.43-7.22, 6.98-6.88, 6.88-6.78, 4.11-3.99, 3.99-3.88, 3.76-3.65, 3.10, 2.86-2.70, 2.21-2.09, 2.09-1.98, 1.98-1.84, 1.65-1.43, 1.43-1.29.

Example 1-6: 1-Benzofuran-2-yl[(3aS,4R,6aR)-4-[(6-chloro-3-pyridazinyl)amino]hexahydrocyclopenta[c]pyrrol-2(1H)-yl]methanone

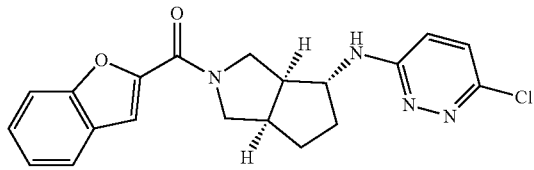 [SMILES: O=C(c1cc2ccccc2o1)N1C[C@@H]2CC[C@@H](Nc3ccc(Cl)nn3)[C@@H]2C1]

HPLC retention time (min): 1.00 (formic acid);
MS (ESI, Pos.): 383 (M+H)$^+$;
$^1$H-NMR (DMSO-d$_6$): δ 7.79-7.74, 7.71-7.65, 7.57-7.49, 7.49-7.43, 7.41-7.32, 7.31-7.25, 6.96-6.84, 4.14-4.01, 3.83-3.72, 3.34-3.25, 2.97-2.76, 2.73-2.66, 2.64-2.53, 2.25-2.15, 2.10-1.98, 1.65-1.57, 1.56-1.46.

Reference Example 11: 2-Methyl-2-propanyl (3aS,4R,6aR)-4-[(6-bromo-3-pyridazinyl)amino]hexahydrocyclopenta[c]pyrrole-2(1H)-carboxylate DIPEA (18 mL) and 3,6-dibromopyridazine (CAS No.: 17973-86-3, 6.3 g) were added to a solution of the compound (4.0 g) prepared in Reference Example 8 in DMA (25 mL), and the mixture was stirred at 160° C. for 15 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (4.0 g).
HPLC retention time (min): 0.91 (formic acid);
MS (ESI, Pos.): 383 (M+H)$^+$.

Reference Example 12: (3aS,4R,6aR)—N-(6-Bromo-3-pyridazinyl)octahydrocyclopenta[c]pyrrole-4-amine dihydrochloride To the compound (4.0 g) prepared in Reference Example 11, was added 4 N hydrochloric acid (1,4 dioxane solution, 12 mL), and the mixture was stirred at room temperature for 1 hour. The reaction solution was concentrated under reduced pressure to obtain the title compound (3.7 g).
HPLC retention time (min): 0.59 (formic acid);
MS (ESI, Pos.): 283 (M+H)$^+$.

Reference Example 12-1: rel-(3aS,4R,6aR)—N-(6-Bromo-3-pyridazinyl)octahydrocyclopenta[c]pyrrole-4-amine dihydrochloride racemic mixture The same procedures as in Reference Example 4→Reference Example 5→Reference Example 6→Reference Example 7→Reference Example 8→Reference Example 11→Reference Example 12 were carried out using the compound prepared in Reference Example 1 in place of the compound prepared in Reference Example 3 to obtain the title compound.

Example 2: [(3aS,4R,6aR)-4-[(6-Bromo-3-pyridazinyl)amino]hexahydrocyclopenta[c]pyrrol-2(1H)-yl](5-methyl-2-thienyl)methanone

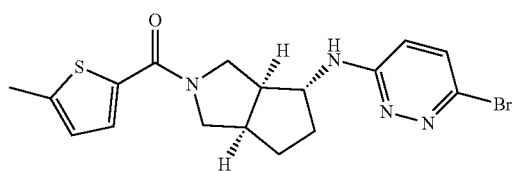 [SMILES: Cc1ccc(C(=O)N2C[C@@H]3CC[C@@H](Nc4ccc(Br)nn4)[C@@H]3C2)s1]

DIPEA (2.9 mL), 5-methyl-2-thiophenecarboxylic acid (CAS No.: 1918-79-2, 6.6 g), and HATU (3.8 g) were added to a solution of the compound (3.0 g) prepared in Reference Example 12 in DMA (20 mL), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (1.8 g).
HPLC retention time (min): 0.87 (TFA);
MS (ESI, Pos.): 407 (M+H)$^+$;
$^1$H-NMR (CDCl$_3$): δ 7.33-7.27, 6.75-6.72, 6.54, 5.00, 4.15-3.99, 3.98-3.78, 3.66, 2.88, 2.68, 2.50, 2.39-2.29, 2.14-2.03, 1.68-1.59.

Examples 2-1 to 2-14

The same procedure as in Example 2 was carried out using a corresponding carboxylic acid compound in place of 5-methyl-2-thiophenecarboxylic acid to obtain each of the title compounds.

Example 2-1: [(3aS,4R,6aR)-4-[(6-Bromo-3-pyridazinyl)amino]hexahydrocyclopenta[c]pyrrol-2(1H)-yl](6,7-dihydro-4H-thieno[3,2-c]pyran-2-yl)methanone

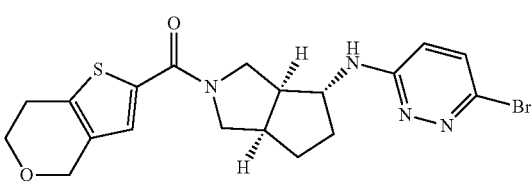 [SMILES: O=C(c1cc2c(s1)CCOC2)N1C[C@@H]2CC[C@@H](Nc3ccc(Br)nn3)[C@@H]2C1]

HPLC retention time (min): 0.93 (TFA);

MS (ESI, Pos.): 451 (M+H)⁺;

¹H-NMR (CDCl₃): δ 7.32-7.27, 7.17, 6.54, 4.77-4.63, 4.10, 4.04-3.93, 3.87, 3.65, 2.89, 2.69, 2.40-2.29, 2.17-2.07, 1.68-1.57.

Example 2-2: [(3aS,4R,6aR)-4-[(6-Bromo-3-pyridazinyl)amino]hexahydrocyclopenta[c]pyrrol-2(1H)-yl][5-(difluoromethyl)-2-thienyl]methanone

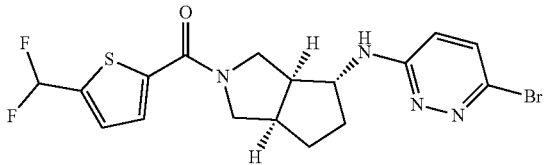 [SMILES: O=C(c1ccc(C(F)F)s1)N1C[C@@H]2CC[C@@H](Nc3ccc(Br)nn3)[C@@H]2C1]

HPLC retention time (min): 1.00 (formic acid);

MS (ESI, Pos.): 443 (M+H)⁺;

¹H-NMR (DMSO-d₆): δ 7.63-7.56, 7.50-7.47, 7.46-7.43, 7.34-7.27, 7.32, 6.86-6.73, 4.11-3.87, 3.87-3.70, 3.71-3.54, 2.96-2.72, 2.71-2.56, 2.23-2.11, 2.09-1.95, 1.59, 1.51.

Example 2-3: [(3aS,4R,6aR)-4-[(6-Bromo-3-pyridazinyl)amino]hexahydrocyclopenta[c]pyrrol-2(1H)-yl](5-methyl-1,3-thiazol-2-yl)methanone

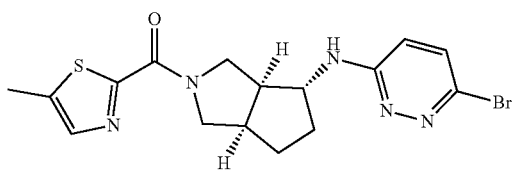 [SMILES: Cc1cnc(C(=O)N2C[C@@H]3CC[C@@H](Nc4ccc(Br)nn4)[C@@H]3C2)s1]

HPLC retention time (min): 0.96 (formic acid);

MS (ESI, Pos.): 408 (M+H)⁺;

¹H-NMR (DMSO-d₆): δ 7.77-7.68, 7.50-7.41, 7.41-7.28, 6.87-6.77, 4.29-3.93, 3.84-3.62, 3.18-3.04, 2.97-2.60, 2.24-2.11, 2.11-1.95, 1.66-1.54, 1.54-1.43.

Example 2-4: [(3aS,4R,6aR)-4-[(6-Bromo-3-pyridazinyl)amino]hexahydrocyclopenta[c]pyrrol-2(1H)-yl](thieno[3,2-c]pyridin-2-yl)-methanone

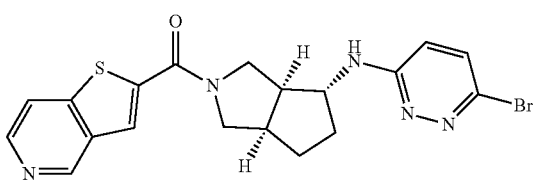 [SMILES: O=C(c1cc2cnccc2s1)N1C[C@@H]2CC[C@@H](Nc3ccc(Br)nn3)[C@@H]2C1]

HPLC retention time (min): 0.75 (formic acid);

MS (ESI, Pos.): 444 (M+H)⁺;

¹H-NMR (DMSO-d₆): δ 9.42-9.26, 8.60, 8.44-8.31, 8.31-8.17, 7.52-7.42, 7.42-7.31, 6.88-6.74, 4.17-4.00, 3.89-3.67, 3.14-3.06, 2.87, 2.28-2.14, 2.13-1.97, 1.70-1.45.

Example 2-5: [(3aS,4R,6aR)-4-[(6-Bromo-3-pyridazinyl)amino]hexahydrocyclopenta[c]pyrrol-2(1H)-yl](6,7-dihydro-4H-pyrano[3,4-d][1,3]thiazol-2-yl)methanone

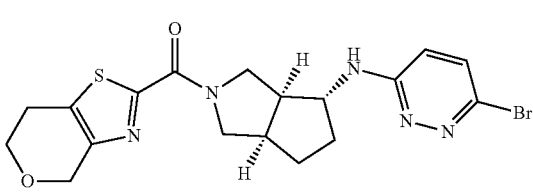 [SMILES: O=C(c1nc2c(s1)CCOC2)N1C[C@@H]2CC[C@@H](Nc3ccc(Br)nn3)[C@@H]2C1]

HPLC retention time (min): 0.84 (TFA);

MS (ESI, Pos.): 452 (M+H)⁺;

¹H-NMR (CDCl₃): δ 7.31-7.27, 6.54, 4.85-4.78, 4.73, 4.34-4.27, 4.21, 4.15-3.97, 3.95-3.84, 3.78, 3.65, 2.97, 2.90-2.71, 2.69-2.59, 2.39-2.28, 2.18-2.01, 1.69-1.61.

Example 2-6: [(3aS,4R,6aR)-4-[(6-Bromo-3-pyridazinyl)amino]hexahydrocyclopenta[c]pyrrol-2(1H)-yl][2-(dimethylamino)-1,3-thiazol-5-yl]methanone

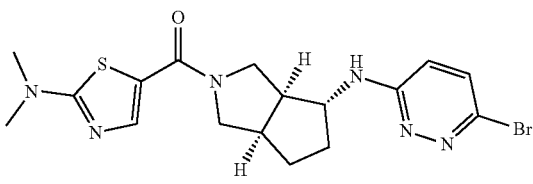 [SMILES: CN(C)c1ncc(C(=O)N2C[C@@H]3CC[C@@H](Nc4ccc(Br)nn4)[C@@H]3C2)s1]

HPLC retention time (min): 0.74 (TFA);

MS (ESI, Pos.): 438 (M+H)⁺;

¹H-NMR (CDCl₃): δ 7.57, 7.26, 6.55, 4.92, 4.15-4.02, 3.98-3.89, 3.87, 3.78, 3.61, 3.15, 2.89, 2.69, 2.39-2.29, 2.17-2.07, 1.62-1.55.

Example 2-7: [(3aS,4R,6aR)-4-[(6-Bromo-3-pyridazinyl)amino]hexahydrocyclopenta[c]pyrrol-2(1H)-yl](5,5-dioxido-6,7-dihydro-4H-thieno[3,2-c]thiopyran-2-yl)methanone

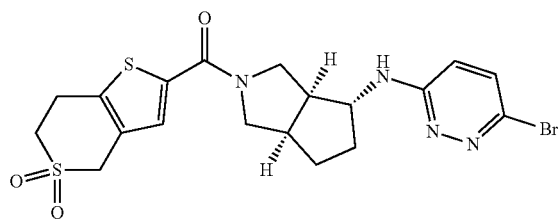 [SMILES: O=C(c1cc2c(s1)CCS(=O)(=O)C2)N1C[C@@H]2CC[C@@H](Nc3ccc(Br)nn3)[C@@H]2C1]

HPLC retention time (min): 0.88 (formic acid);

MS (ESI, Pos.): 497 (M+H)⁺;

¹H-NMR (DMSO-d₆): δ 7.46, 7.33, 6.82, 4.39, 4.11-3.99, 3.97-3.83, 3.81-3.65, 3.18-3.05, 2.99-2.72, 2.70-2.58, 2.24-2.09, 2.09-1.96, 1.58, 1.49.

Example 2-8: [(3aS,4R,6aR)-4-[(6-Bromo-3-pyridazinyl)amino]hexahydrocyclopenta[c]pyrrol-2(1H)-yl](6,7-dihydro-4H-thieno[3,2-c]thiopyran-2-yl)methanone

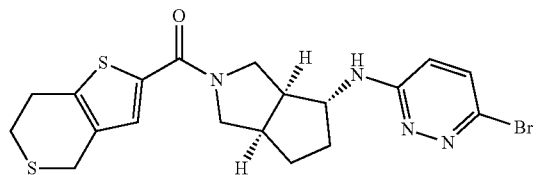 [SMILES: O=C(c1cc2c(s1)CCSC2)N1C[C@@H]2CC[C@@H](Nc3ccc(Br)nn3)[C@@H]2C1]

HPLC retention time (min): 1.00 (formic acid);

MS (ESI, Pos.): 465 (M+H)+;

$^1$H-NMR (DMSO-d$_6$): δ 7.46, 7.41-7.31, 6.86-6.77, 4.11-4.02, 4.02-3.86, 3.71, 3.69-3.58, 3.46, 3.15-3.05, 3.04-2.96, 2.94-2.88, 2.88-2.71, 2.25-2.12, 2.10-1.94, 1.68-1.54, 1.54-1.39.

Example 2-9: [(3aS,4R,6aR)-4-[(6-Bromo-3-pyridazinyl)amino]hexahydrocyclopenta[c]pyrrol-2(1H)-yl](1-methyl-1H-thieno[2,3c]pyrazol-5-yl)methanone

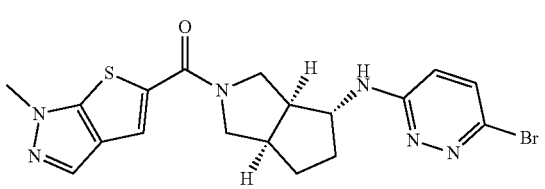 [SMILES: Cn1ncc2cc(C(=O)N3C[C@@H]4CC[C@@H](Nc5ccc(Br)nn5)[C@@H]4C3)sc21]

HPLC retention time (min): 0.90 (formic acid);

MS (ESI, Pos.): 447 (M+H)+;

$^1$H-NMR (DMSO-d$_6$): δ 7.85, 7.69-7.57, 7.52-7.43, 7.43-7.28, 6.89-6.70, 4.12-4.00, 3.96, 3.92-3.67, 3.15-3.05, 2.96-2.75, 2.75-2.57, 2.26-2.11, 2.09-1.94, 1.66-1.55, 1.55-1.44.

Example 2-10: [(3aS,4R,6aR)-4-[(6-Bromo-3-pyridazinyl)amino]hexahydrocyclopenta[c]pyrrol-2(1H)-yl][2-(dimethylamino)thieno[2,3-d][1,3]thiazol-5-yl]methanone

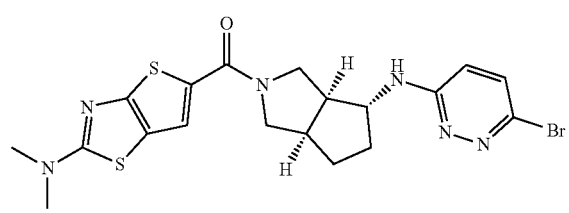 [SMILES: CN(C)c1nc2sc(C(=O)N3C[C@@H]4CC[C@@H](Nc5ccc(Br)nn5)[C@@H]4C3)cc2s1]

HPLC retention time (min): 0.88 (TFA);

MS (ESI, Pos.): 493 (M+H)+;

$^1$H-NMR (DMSO-d$_6$): δ 7.79, 7.44, 7.25, 6.79, 4.16-3.94, 3.86, 3.74, 3.56, 3.44-3.36, 3.31-3.23, 3.13, 2.87, 2.61, 2.19, 2.07-1.98, 1.63-1.47.

Example 2-11: [(3aS,4R,6aR)-4-[(6-Bromo-3-pyridazinyl)amino]hexahydrocyclopenta[c]pyrrol-2(1H)-yl](3-methyl-3H-thieno[2,3-d][1,2,3]triazol-5-yl)methanone

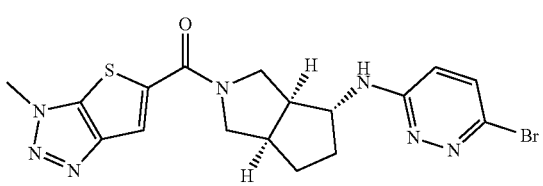 [SMILES: Cn1nnc2cc(C(=O)N3C[C@@H]4CC[C@@H](Nc5ccc(Br)nn5)[C@@H]4C3)sc21]

HPLC retention time (min): 0.87 (formic acid);

MS (ESI, Pos.): 448 (M+H)+;

$^1$H-NMR (DMSO-d$_6$): δ 7.91, 7.46, 7.44-7.36, 6.84, 4.24, 4.14-3.98, 3.95-3.61, 3.00-2.79, 2.77-2.59, 2.27-2.16, 2.11-1.98, 1.65-1.57, 1.57-1.50.

Example 2-12: [(3aS,4R,6aR)-4-[(6-Bromo-3-pyridazinyl)amino]hexahydrocyclopenta[c]pyrrol-2(1H)-yl](5-methoxy-2-furyl)methanone

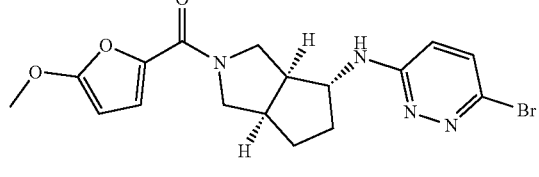

HPLC retention time (min): 0.80 (TFA);

MS (ESI, Pos.): 407 (M+H)+;

$^1$H-NMR (CDCl$_3$): δ 7.31-7.27, 7.05, 6.54, 5.31, 4.81-4.66, 4.12, 3.92, 3.94-3.77, 3.76-3.58, 2.95-2.76, 2.72-2.52, 2.34, 2.05, 1.66-1.56.

Example 2-13: [(3aS,4R,6aR)-4-[(6-Bromo-3-pyridazinyl)amino]hexahydrocyclopenta[c]pyrrol-2(1H)-yl](1,3-dimethyl-1H-thieno[2,3-c]pyrazol-5-yl)methanone

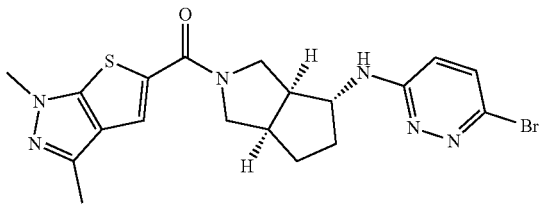 [SMILES: Cc1nn(C)c2sc(C(=O)N3C[C@@H]4CC[C@@H](Nc5ccc(Br)nn5)[C@@H]4C3)cc12]

HPLC retention time (min): 0.93 (formic acid);

MS (ESI, Pos.): 461 (M+H)+;

$^1$H-NMR (DMSO-d$_6$): δ 7.62, 7.51-7.44, 7.45-7.36, 6.88-6.79, 4.13-4.04, 3.85, 4.01-3.66, 3.36-3.24, 2.95-2.80, 2.71-2.58, 2.37, 2.26-2.15, 2.11-2.00, 1.64-1.57, 1.56-1.48.

Example 2-14: Bicyclo[2.2.2]oct-2-yl[(3aS,4R, 6aR)-4-[(6-bromo-3-pyridazinyl)amino]hexahydro-cyclopenta[c]pyrrol-2(1H)-yl]methanone

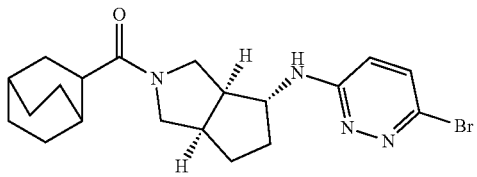 [SMILES: O=C(C1CC2CCC1CC2)N1C[C@@H]2CC[C@@H](Nc3ccc(Br)nn3)[C@@H]2C1]

HPLC retention time (min): 1.10 (formic acid);
MS (ESI, Pos.): 419 (M+H)$^+$;
$^1$H-NMR (DMSO-d$_6$): δ 7.51-7.39, 7.38-7.25, 6.85-6.74, 4.07-3.85, 3.73-3.51, 3.29-3.16, 2.87-2.59, 2.18-1.82, 1.72-1.14.

Reference Example 13: Methyl 5-[(1E)-3-ethoxy-3-oxo-1-propen-1-yl]-4-nitro-2-thiophenecarboxylate DIPEA (0.083 mL) and tripotassium phosphate (CAS No.: 7778-53-2, 1730 mg), (E)-ethyl 3-(4,4,5,5-tetramethyl-1,3,2-dioxaborolan-2-yl)acrylate (CAS No.: 1009307-13-4, 300 mg), and bis(triphenylphosphine)palladium(II) chloride (CAS No.: 13965-03-2, 63 mg) were added to a solution of methyl 5-bromo-4-nitrothiophene-2-carboxylate (CAS No.: 38239-32-6, 120 mg) in 1,2-dimethoxyethane (3 mL), and the mixture was stirred at 55° C. for 3 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (97 mg).

HPLC retention time (min): 1.20 (formic acid);
MS (ESI, Pos.): 286 (M+H)$^+$.

Reference Example 14: Methyl 4-amino-5-(3-ethoxy-3-oxopropyl)-2-thiophenecarboxylate To a solution of the compound (50 mg) prepared in Reference Example 13 in methanol (2 mL), was added 20% palladium hydroxide (100 mg), and the mixture was stirred under a hydrogen atmosphere at room temperature for 1 hour. The reaction solution was filtered and concentrated under reduced pressure. The resulting residue was purified by silica gel column chromatography to obtain the title compound (30 mg).

HPLC retention time (min): 0.80 (formic acid);
MS (ESI, Pos.): 258 (M+H)$^+$.

Reference Example 15: Methyl 5-oxo-4,5,6,7-tetrahydrothieno[3,2-b]pyridine-2-carboxylate To a solution of the compound (20 mg) prepared in Reference Example 14 in methanol (1 mL), was added p-toluenesulfonic acid monohydrate (CAS No.: 6192-52-5, 1.5 mg), and the mixture was stirred at 60° C. for 15 hours. Saturated sodium bicarbonate water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (5 mg).

HPLC retention time (min): 0.81 (formic acid);
MS (ESI, Pos.): 212 (M+H)$^+$.

Reference Example 16: Methyl 4-methyl-5-oxo-4,5,6,7-tetrahydrothieno[3,2-b]pyridine-2-carboxylate Sodium hydride (CAS No.: 7646-69-7, 2.9 mg) and iodomethane (CAS No.: 74-88-4, 22 mg) were added to a solution of the compound (5 mg) prepared in Reference Example 15 in DMF (0.25 mL), and the mixture was stirred at room temperature for 3 hours. Then, 2 N hydrochloric acid was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (7 mg).

HPLC retention time (min): 0.88 (formic acid);
MS (ESI, Pos.): 225 (M+H)$^+$.

Reference Example 17: 4-Methyl-5-oxo-4,5,6,7-tetrahydrothieno[3,2-b]pyridine-2-carboxylic acid A 2 N aqueous sodium hydroxide solution (0.5 mL) was added to a solution of the compound (7 mg) prepared in Reference Example 16 in methanol (1 mL), and the mixture was stirred at 60° C. for 1 hour. Then, 1 N hydrochloric acid was added to the reaction solution, and the precipitate was collected by filtration to obtain the title compound (5.0 mg).

Reference Example 18: 5-Chloro-3,4-dihydro-2H-pyran-6-carbaldehyde

DMF (0.70 mL) was added to a solution of phosphoryl chloride (CAS No.: 10025-87-3, 1,400 mg) in dichloromethane (5 mL) at 0° C., and the mixture was stirred at 0° C. for 1 hour. Dihydro-2H-pyran-3(4H)-one (CAS No.: 23462-75-1, 900 mg) was added to the mixed solution, and the mixture was stirred at room temperature for 2 hours. A saturated aqueous sodium bicarbonate solution was added to the reaction solution, followed by extraction with dichloromethane. The organic layer was washed with saturated saline, dried over anhydrous sodium sulfate, and concentrated under reduced pressure. The obtained title compound was used for the next reaction without purification.

Reference Example 19: Methyl [(6-formyl-3,4-dihydro-2H-pyran-5-yl)thio]acetate Triethylamine (2.5 mL) and methyl thioglycolate (CAS No.: 2365-48-2, 1,100 mg) were added to a solution of the compound prepared in Reference Example 18 in dichloroethane (20 mL), and the mixture was stirred at 70° C. for 15 hours. The reaction solution was concentrated under reduced pressure, and the obtained residue was purified by silica gel column chromatography to obtain the title compound (300 mg).

Reference Example 20: Methyl 6,7-dihydro-5H-thieno[3,2-b]pyran-2-carboxylate To a solution of the compound prepared in Reference Example 19 in methanol (10 mL), was added 28% sodium methoxide (CAS No.: 124-41-4, 0.85 mL), and the mixture was stirred at 70° C. for 1 hour. The reaction solution was concentrated under reduced pressure, and 2 N hydrochloric acid was added thereto, followed by extraction with dichloromethane. The organic layer was washed with saturated saline, dried over anhydrous sodium sulfate, and concentrated under reduced pressure. The resulting residue was purified by silica gel column chromatography to obtain the title compound (220 mg).

Reference Example 21: 6,7-Dihydro-5H-thieno[3,2-b]pyran-2-carboxylic acid

A 2 N aqueous sodium hydroxide solution (0.5 mL) was added to a solution of the compound (20 mg) prepared in Reference Example 20 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

HPLC retention time (min): 1.00 (formic acid);
MS (ESI, Pos.): 449 (M+H)$^+$;
$^1$H-NMR (DMSO-d$_6$): δ 7.55-7.43, 7.10, 6.89-6.60, 4.67-4.62, 4.17-4.07, 4.05-3.87, 3.73, 3.67, 3.42-3.40, 3.37-3.33, 3.30, 3.22-3.04, 2.79-2.70, 2.58-2.53, 2.17, 2.09-1.85, 1.71-1.37.

Reference Example 22: Dimethyl 6,7-dihydrothieno[3,2-c]pyridine-2,5(4H)-dicarboxylate Triethylamine (0.11 mL) and methyl chloroformate (CAS No.: 79-22-1, 72 mg) were added to a solution of methyl 4,5,6,7-tetrahydrothieno[3,2-c]pyridine-2-carboxylate (CAS No.: 221316-61-6, 50 mg) in dichloromethane (1 mL) at 0° C., and the mixture was stirred at room temperature for 15 hours. Then, 2 N hydrochloric acid was added to the reaction solution, followed by extraction with dichloromethane. The organic layer was washed with saturated saline, dried over anhydrous sodium sulfate, and concentrated under reduced pressure. The obtained title compound was used for the next reaction without purification.

Reference Example 23: 5-(Methoxycarbonyl)-4,5,6,7-tetrahydrothieno[3,2-c]pyridine-2-carboxylic acid A 2 N aqueous sodium hydroxide solution (0.5 mL) was added to a solution of the compound (20 mg) prepared in Reference Example 22 in methanol (1 mL), and the mixture was stirred at 50° C. for 1 hour. Then, 1 N hydrochloric acid was added to the reaction solution, and the organic layer was washed with saturated saline, dried over anhydrous sodium sulfate, and concentrated under reduced pressure. The obtained title compound was used for the next reaction without purification.

Reference Example 24: 4,4-Dimethyl-6,7-dihydrothieno[3,2-c]pyran

To a solution of 2-(2-thienyl)ethanol (CAS No.: 160774-13-8, 400 mg) in toluene (4 mL), were added 2,2-dimethoxypropane (CAS No.: 77-76-9, 0.38 mL) and iron(III) trifluoromethanesulfonate (CAS No.: 63295-48-7, 15.7 mg), and the mixture was stirred at 70° C. for 17 hours. Triethylamine (0.22 mL) was added to the reaction solution, and the mixture was concentrated under reduced pressure. The resulting residue was purified by silica gel column chromatography to obtain the title compound (284 mg).

TLC: Rf 0.50 (ethyl acetate:n-hexane=1:9);
HPLC retention time (min): 1.07 (TFA);
MS (ESI, Pos.): 169 (M+H)$^+$.

Reference Example 25: 4,4-Dimethyl-6,7-dihydrothieno[3,2-c]pyran-2-carboxylic acid A 1.6 M n-butyllithium-hexane solution (CAS No.: 109-72-8, 1.2 mL) was added to a solution of the compound (284 mg) prepared in Reference Example 24 in THF (10 mL) at −78° C., and the mixture was stirred at −78° C. for 2 hours. Thereafter, dry ice (1 g) was added to the reaction solution, and the mixture was stirred at room temperature for 2 hours. Water and a 1 N aqueous sodium hydroxide solution were added to the reaction solution, and the aqueous layer was washed with methyl tert-butyl ether. A 1 N aqueous hydrochloric acid solution was added to the aqueous layer to adjust the pH of the aqueous layer to 1, followed by extraction with ethyl acetate. The organic layer was washed with saturated saline and dried over anhydrous sodium sulfate, then concentrated under reduced pressure to obtain the title compound (306 mg).

HPLC retention time (min): 0.89 (TFA);
MS (ESI, Pos.): 213 (M+H)$^+$.

Reference Example 26: 4H-Pyrano[3,4-d]thiazol-7-one

To a solution of 2-amino-4H-pyrano[3,4-d]thiazol-7-one (CAS No.: 1253281-38-7, 873 mg) in THE (17.5 mL), was added n-pentyl nitrite (CAS No.: 463-04-7, 0.97 mL), and the mixture was stirred at 60° C. for 15 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (568 mg).

TLC: Rf 0.28 (ethyl acetate:n-hexane=1:2).

Reference Example 27: 7-Methylene-4H-pyrano[3,4-d]thiazole

A 1.3 N lithium bis(trimethylsilyl)amide THE solution (CAS No.: 4039-32-1, 0.55 mL) was added to a solution of methyltriphenylphosphonium bromide (CAS No.: 1779-49-3, 253 mg) in THE (1.5 mL) at 0° C., and the mixture was stirred at 0° C. for 1 hour. Thereafter, the compound (100 mg) prepared in Reference Example 26 was added thereto, and the mixture was stirred at 0° C. for 40 minutes. A saturated aqueous ammonium chloride solution was added to the reaction solution, and the aqueous layer was subjected to extraction with dichloromethane. The organic layer was washed with saturated saline, dried over anhydrous sodium sulfate, and concentrated under reduced pressure. The resulting residue was purified by silica gel column chromatography to obtain the title compound (90 mg).

TLC: Rf 0.5 (ethyl acetate:n-hexane=1:2).

Reference Example 28: 7-Methyl-6,7-dihydro-4H-pyrano[3,4-d][1,3]thiazole

To a solution of the compound prepared in Reference Example 27 in methanol (1.8 mL), was added 20% palladium hydroxide (10 mg), and the mixture was stirred under a hydrogen atmosphere at room temperature for 7 hours. The reaction solution was filtered and concentrated under reduced pressure. The resulting residue was purified by silica gel column chromatography to obtain the title compound (40 mg).

Reference Example 29: 7-Methyl-6,7-dihydro-4H-pyrano[3,4-d][1,3]thiazol-2-carboxylic acid A 1.6 M n-butyllithium hexane solution (0.16 mL) was added to a solution of the compound (40 mg) prepared in Reference Example 28 in THF (2 mL) at −78° C., and the mixture was stirred at −78° C. for 1 hour. Thereafter, dry ice (300 mg) was added to the reaction solution, and the mixture was stirred at room temperature for 1 hour. Water and a 1 N aqueous sodium hydroxide solution were added to the reaction solution, and the aqueous layer was washed with methyl tert-butyl ether. A 1 N aqueous hydrochloric acid solution was added to the aqueous layer to adjust the pH of the aqueous layer to 1, followed by extraction with ethyl acetate. The organic layer was washed with saturated saline and dried over anhydrous sodium sulfate, then concentrated under reduced pressure to obtain the title compound (20 mg).
HPLC retention time (min): 0.76 (TFA);
MS (ESI, Pos.): 200 (M+H)$^+$.

Reference Example 30: Methyl 5-hydroxy-2-thiophenecarboxylate

A 30% aqueous hydrogen peroxide solution (CAS No.: 7722-84-1, 0.11 mL) was added to a solution of thiophene-2-carboxylic acid methyl ester-5-boronic acid (CAS No.: 876189-21-8, 120 mg) in polyethylene glycol 200 (CAS No.: 25322-68-3, 0.64 mL), and the mixture was stirred at room temperature for 2 hours. Water was added to the reaction solution, followed by extraction with methyl tert-butyl ether. The organic layer was washed with saturated saline, dried over anhydrous sodium sulfate, and concentrated under reduced pressure. The resulting residue was purified by silica gel column chromatography to obtain the title compound (23 mg).
HPLC retention time (min): 0.84 (TFA);
MS (ESI, Pos.): 171 (M+Na)$^+$.

Reference Example 31: Methyl 5-(difluoromethoxy)-2-thiophenecarboxylate

Chlorodifluoroacetic acid (CAS No.: 76-04-0, 0.027 mL) and cesium carbonate (CAS No.: 534-17-8, 142 mg) were added to a solution of the compound (23 mg) prepared in Reference Example 30 in DMF (0.2 mL), and the mixture was stirred at 100° C. for 10 minutes. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (31 mg).
HPLC retention time (min): 1.06 (TFA);
MS (ESI, Pos.): 209 (M+H)$^+$.

Reference Example 32: 5-(Difluoromethoxy)-2-thiophenecarboxylic acid

Methanol (0.1 mL) and a 1 N aqueous lithium hydroxide solution (CAS No.: 1310-65-2, 0.2 mL) were added to a solution of the compound (31 mg) prepared in Reference Example 31 in THF (0.2 mL), and the mixture was stirred at room temperature for 16 hours. A 1 N aqueous hydrochloric acid solution was added to the reaction solution to adjust the pH of the aqueous layer to 1, followed by extraction with ethyl acetate. The organic layer was washed with saturated saline and dried over anhydrous sodium sulfate, then concentrated under reduced pressure to obtain the title compound (21 mg).
HPLC retention time (min): 0.91 (TFA);
MS (ESI, Pos.): 195 (M+H)$^+$.

Reference Example 33: Methyl 3-iodo-1H-thieno[3,2-c]pyrazole-5-carboxylate

Potassium hydroxide (CAS No.: 1310-58-3, 140 mg) and iodine (CAS No.: 7553-56-2, 570 mg) were added to a solution of methyl 1H-thieno[3,2-c]pyrazole-5-carboxylate (CAS No.: 1246552-43-1, 185 mg) in DMF (2 mL), and the mixture was stirred at 0° C. for 1 hour. Then, 2 N hydrochloric acid was added to the reaction solution, and a saturated aqueous sodium thiosulfate solution was added thereto, followed by extraction with ethyl acetate. The organic layer was washed with saturated saline, dried over anhydrous sodium sulfate, and concentrated under reduced pressure. The resulting residue was washed with hexane and ethyl acetate to obtain the title compound (180 mg).

Reference Example 34: Methyl 3-(3-hydroxy-1-propyn-1-yl)-1H-thieno[3,2-c]pyrazole-5-carboxylate Propargyl alcohol (CAS No.: 107-19-7, 11 mg), copper(I) iodide (CAS No.: 7681-65-4, 2.5 mg), tetrakis(triphenylphosphine)palladium(0) (CAS No.: 14221-01-3, 15 mg), and triethylamine (0.09 mL) were added to a solution of the compound (40 mg) prepared in Reference Example 33 in THF (1 mL), and the mixture was stirred at 60° C. for 1 hour. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (23 mg).
HPLC retention time (min): 0.84 (formic acid);
MS (ESI, Pos.): 237 (M+H)$^+$.

Reference Example 35: Methyl 3-(3-hydroxypropyl)-1H-thieno[3,2-c]pyrazole-5-carboxylate To a solution of the compound (23 mg) prepared in Reference Example 34 in methanol (1 mL), was added 20% palladium hydroxide (25 mg), and the mixture was stirred under a hydrogen atmosphere at room temperature for 6 hours. The reaction solution was filtered and concentrated under reduced pressure, and the obtained title compound was used for the next reaction without purification.

Reference Example 36: Methyl 7,8-dihydro-6H-pyrrolo[1,2-b]thieno[2,3-d]pyrazole-2-carboxylate Cyanomethylene tributylphosphorane (CAS No.: 157141-27-0, 27 mg) was added to a solution of the compound (18 mg) prepared in Reference Example 35 in toluene (0.5 mL), and the mixture was stirred at 60° C. for 1 hour. The mixture was purified by silica gel column chromatography to obtain the title compound (10 mg).
$^1$H-NMR (CDCl$_3$): δ 7.85, 4.38, 3.83, 3.10, 2.73.

Reference Example 37: 7,8-Dihydro-6H-pyrrolo[1,2-b]thieno[2,3-d]pyrazole-2-carboxylic acid A 2 N aqueous sodium hydroxide solution (0.5 mL) was added to a solution of the compound (20 mg) prepared in Reference Example 36 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 38: Methyl 5-methyl-4-(1-methyl-1H-pyrazol-4-yl)-2-thiophenecarboxylate Water (0.37 mL), 1-methyl-1H-pyrazole-4-boronic acid (CAS No.: 847818-55-7, 48 mg), cesium carbonate (124 mg), and tetrakis(triphenylphosphine)palladium(0) (15 mg) were added to a solution of methyl 4-bromo-5-methylthiophene-2-carboxylate (CAS No.: 237385-15-8, 30 mg) in toluene (0.75 mL), and the mixture was stirred at 80° C. for 13 hours. The reaction solution was subjected to extraction with ethyl acetate. The organic layer was washed with saturated saline, dried over anhydrous sodium sulfate, and concentrated under reduced pressure. The resulting residue was purified by silica gel column chromatography to obtain the title compound (10 mg).
HPLC retention time (min): 1.00 (formic acid);
MS (ESI, Pos.): 237 (M+H)+.

Reference Example 39: 5-Methyl-4-(1-methyl-1H-pyrazol-4-yl)-2-thiophenecarboxylic acid A 2 N aqueous sodium hydroxide solution (0.5 mL) was added to a solution of the compound (20 mg) prepared in Reference Example 38 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 40: Methyl 2,3-dimethyl-2H-thieno[2,3-c]pyrazole-5-carboxylate Sodium hydride (2.9 mg) and iodomethane (22 mg) were added to a solution of methyl 3-methyl-1H-thieno[2,3-c]pyrazole-5-carboxylate (CAS No.: 873072-42-5, 20 mg) in DMF (1.0 mL), and the mixture was stirred at room temperature for 3 hours. Then, 2 N hydrochloric acid was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (10 mg).
1H-NMR (CDCl$_3$): δ 7.69, 3.95, 3.89, 2.52.

Reference Example 41: 2,3-Dimethyl-2H-thieno[2,3-c]pyrazole-5-carboxylic acid A 2 N aqueous sodium hydroxide solution (0.5 mL) was added to a solution of the compound (20 mg) prepared in Reference Example 40 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 42: Methyl 2-methyl-2H-thieno[3,2-c]pyrazole-5-carboxylate Cesium carbonate (7.2 g) and iodomethane (1.6 g) were added to a solution of methyl 1H-thieno[3,2-c]pyrazole-5-carboxylate (2.0 g) in THF (40 mL), and the mixture was stirred at room temperature for 3 hours. Then, 2 N hydrochloric acid was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (1.05 g).
1H-NMR (CDCl$_3$): δ 7.70, 7.66, 4.06, 3.93.

Reference Example 43: 2-Methyl-2H-thieno[3,2-c]pyrazole-5-carboxylic acid

A 2 N aqueous sodium hydroxide solution (0.5 mL) was added to a solution of the compound (20 mg) prepared in Reference Example 42 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 44: Methyl 2-cyclopropyl-2H-thieno[3,2-c]pyrazole-5-carboxylate Cyclopropylboronic acid (CAS No.: 873072-42-5, 940 mg), sodium carbonate (CAS No.: 497-19-8, 1,200 mg), copper(II) acetate (CAS No.: 142-71-2, 1.1 g), and 1,10-phenanthroline (CAS No.: 66-71-7, 1.1 g) were added to a solution of methyl 1H-thieno[3,2-c]pyrazole-5-carboxylate (1.0 g) in dichloroethane (20 mL), and the mixture was stirred at 70° C. for 15 hours. Then, 1 N hydrochloric acid was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (200 mg).
HPLC retention time (min): 1.00 (formic acid);
MS (ESI, Pos.): 223 (M+H)+.

Reference Example 45: 2-Cyclopropyl-2H-thieno[3,2-c]pyrazole-5-carboxylic acid A 2 N aqueous sodium hydroxide solution (0.5 mL) was added to a solution of the compound (20 mg) prepared in Reference Example 44 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 46: Methyl 2-(difluoromethyl)-2H-thieno[3,2-c]pyrazole-5-carboxylate Sodium chlorodifluoroacetate (CAS No.: 1895-39-2, 2,100 mg) and potassium carbonate (1,900 mg) were added to a solution of methyl 1H-thieno[3,2-c]pyrazole-5-carboxylate (500 mg) in DMF (10 mL), and the mixture was stirred at 100° C. for 20 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (85 mg).

Reference Example 47: 2-(Difluoromethyl)-2H-thieno[3,2-c]pyrazole-5-carboxylic acid A 2 N aqueous sodium hydroxide solution (0.5 mL) was added to a solution of the compound (20 mg) prepared in Reference Example 46 in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 48: (1) Methyl 2-(2,2,2-trifluoroethyl)-2H-thieno[3,2-c]pyrazole-5-carboxylate and (2) methyl 1-(2,2,2-trifluoroethyl)-2H-thieno[3,2-c]pyrazole-5-carboxylate Cesium carbonate (720 mg) and 2,2,2-trifluoroethyl trifluoromethanesulfonate (CAS No.: 6226-25-1, 510 mg) were added to a solution of methyl 1H-thieno[3,2-c]pyrazole-5-carboxylate (200 mg) in DMF (5 mL), and the mixture was stirred at room temperature for 15 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain 61 mg of the title compound (1) and 71 mg of the title compound (2).
(1) TLC: Rf 0.31 (ethyl acetate:n-hexane=1:3);
(2) TLC: Rf 0.34 (ethyl acetate:n-hexane=1:3).

Reference Example 49: 2-(2,2,2-Trifluoroethyl)-2H-thieno[3,2-c]pyrazole-5-carboxylic acid A 2 N aqueous sodium hydroxide solution (0.5 mL) was added to a solution of the compound (60 mg) prepared in Reference Example 48 (1) in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 50: 1-(2,2,2-Trifluoroethyl)-1H-thieno[3,2-c]pyrazole-5-carboxylic acid A 2 N aqueous sodium hydroxide solution (0.5 mL) was added to a solution of the compound (60 mg) prepared in Reference Example 48 (2) in methanol (1 mL), and the mixture was stirred at 60° C. for 1 hour. Then, 1 N hydrochloric acid was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Reference Example 51: 2,3-Dimethyl-2H-thieno[3,2-c]pyrazole-5-carboxylic acid

The same procedures as in Reference Example 40→Reference Example 41 were carried out using methyl 3-methyl-1H-thieno[3,2-c]pyrazole-5-carboxylate (CAS No.: 1379258-29-3) in place of methyl 3-methyl-1H-thieno[2,3-c]pyrazole-5-carboxylate to obtain the title compound.

Example 3: 2-{[(3aS,4R,6aR)-4-[(6-Bromo-3-pyridazinyl)amino]hexahydrocyclopenta[c]pyrrol-2(1H)-yl]carbonyl}-4-methyl-6,7-dihydrothieno[3,2-b]pyridin-5(4H)-one

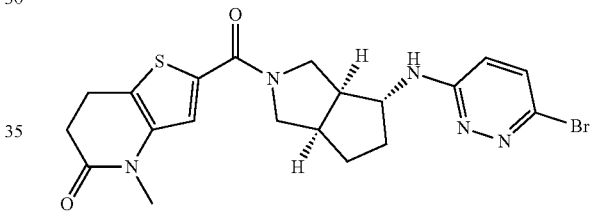

DIPEA (0.016 mL) and HATU (10 mg) were added to a solution of the compound (5 mg) prepared in Reference Example 12 and the compound (9.2 mg) prepared in Reference Example 17 in DMA (0.25 mL), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (4.7 mg).
HPLC retention time (min): 0.89 (formic acid);
MS (ESI, Pos.): 476 (M+H)$^+$;
$^1$H-NMR (DMSO-d$_6$): δ 7.44, 7.38, 7.28, 6.80, 4.10-3.96, 3.24, 3.18-3.03, 3.01-2.87, 2.85, 2.71-2.57, 2.25-2.10, 2.10-1.96, 1.62-1.45.

Examples 3-1 to 3-14

The same procedure as in Example 3 was carried out using the compound prepared in Reference Example 21, Reference Example 23, Reference Example 25, Reference Example 29, Reference Example 32, Reference Example 37, Reference Example 39, Reference Example 41, Reference Example 43, Reference Example 45, Reference Example 47, Reference Example 49, Reference Example 50, or Reference Example 51 in place of the compound prepared in Reference Example 17, and using the compound prepared in Reference Example 12 or the compound prepared in Reference Example 10 in place of the compound prepared in Reference Example 12 to obtain each of the title compounds.

Example 3-1: [(3aS,4R,6aR)-4-[(6-Bromo-3-pyridazinyl)amino]hexahydrocyclopenta[c]pyrrol-2(1H)-yl](6,7-dihydro-5H-thieno[3,2-b]pyran-2-yl)methanone

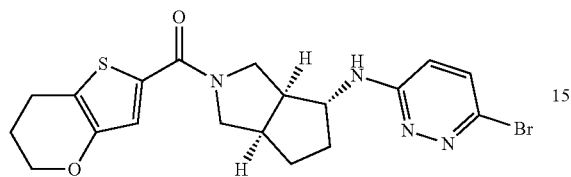

HPLC retention time (min): 0.74 (formic acid);
MS (ESI, Pos.): 400 (M+H)⁺;
¹H-NMR (DMSO-d₆): δ 9.46-9.25, 8.63-8.43, 8.40-8.30, 8.29-8.14, 7.43-7.30, 6.97-6.83, 4.20-4.00, 3.99-3.65, 3.15-3.04, 3.04-2.79, 2.77-2.57, 2.27-2.15, 2.14-1.98, 1.70-1.58, 1.58-1.48.

Example 3-2: Methyl 2-{[(3aS,4R,6aR)-4-[(6-bromo-3-pyridazinyl)amino]hexahydrocyclopenta[c]pyrrol-2(1H)-yl]carbonyl}-6,7-dihydrothieno[3,2-c]pyridine-5(4H)-carboxylate

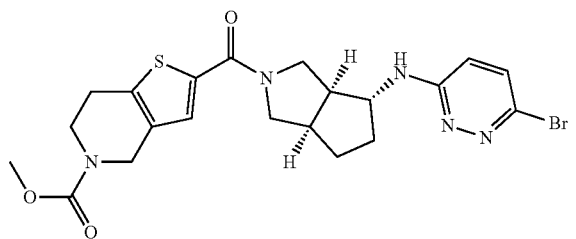 [SMILES: COC(=O)N1CCc2sc(C(=O)N3C[C@@H]4CC[C@@H](Nc5ccc(Br)nn5)[C@@H]4C3)cc2C1]

HPLC retention time (min): 0.97 (formic acid);
MS (ESI, Pos.): 506 (M+H)⁺;
¹H-NMR (DMSO-d₆): δ 7.49-7.44, 7.44-7.31, 6.86-6.78, 4.57-4.41, 4.07-4.00, 3.67, 3.64, 3.20-3.05, 2.81, 2.71-2.45, 2.27-2.12, 2.09-1.95, 1.64-1.54, 1.54-1.42.

Example 3-3: [(3aS,4R,6aR)-4-[(6-Chloro-3-pyridazinyl)amino]hexahydrocyclopenta[c]pyrrol-2(1H)-yl](4,4-dimethyl-6,7-dihydro-4H-thieno[3,2-c]pyran-2-yl)methanone

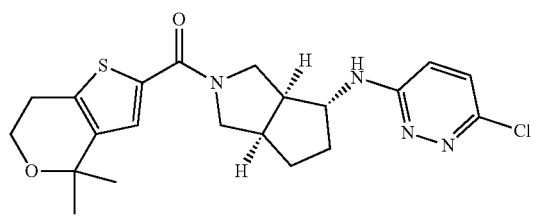 [SMILES: CC1(C)OCCc2sc(C(=O)N3C[C@@H]4CC[C@@H](Nc5ccc(Cl)nn5)[C@@H]4C3)cc21]

HPLC retention time (min): 0.88 (TFA);
MS (ESI, Pos.): 435 (M+H)⁺;
¹H-NMR (CDCl₃): δ 7.23, 7.18, 6.63, 4.70, 4.11, 3.98, 3.95-3.83, 3.66, 3.49, 2.89, 2.83, 2.69, 2.40-2.30, 2.17-2.08, 1.68-1.58, 1.48.

Example 3-4: [(3aS,4R,6aR)-4-[(6-Chloro-3-pyridazinyl)amino]hexahydrocyclopenta[c]pyrrol-2(1H)-yl](7-methyl-6,7-dihydro-4H-pyrano[3,4-d][1,3]thiazol-2-yl)-methanone

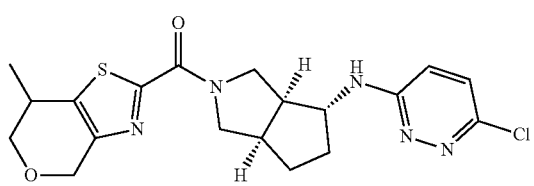 [SMILES: CC1COCc2nc(C(=O)N3C[C@@H]4CC[C@@H](Nc5ccc(Cl)nn5)[C@@H]4C3)sc21]

HPLC retention time (min): 0.88 (TFA);
MS (ESI, Pos.): 420 (M+H)⁺;
¹H-NMR (CDCl₃): δ 7.18, 6.63, 4.85-4.66, 4.25-4.17, 4.15-4.02, 3.85, 3.55-3.46, 3.22, 3.03-2.55, 2.35, 2.13, 1.68-1.57, 1.29.

Example 3-5: [(3aS,4R,6aR)-4-[(6-Chloro-3-pyridazinyl)amino]hexahydrocyclopenta[c]pyrrol-2(1H)-yl][5-(difluoromethoxy)-2-thienyl]methanone

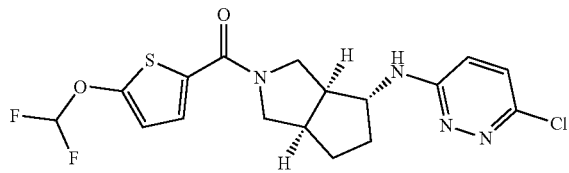 [SMILES: O=C(c1ccc(OC(F)F)s1)N1C[C@@H]2CC[C@@H](Nc3ccc(Cl)nn3)[C@@H]2C1]

HPLC retention time (min): 0.91 (TFA);
MS (ESI, Pos.): 415 (M+H)⁺;
¹H-NMR (CDCl₃): δ 7.32-7.28, 7.26-7.16, 6.67-6.61, 6.64, 4.69, 4.16-4.06, 4.02, 3.87, 3.66, 3.66, 2.88, 2.70, 2.41-2.31, 2.18-2.08, 1.69-1.58.

Example 3-6: [(3aS,4R,6aR)-4-[(6-Bromo-3-pyridazinyl)amino]hexahydrocyclopenta[c]pyrrol-2(1H)-yl](7,8-dihydro-6H-pyrrolo[1,2-b]thieno[2,3-d]pyrazol-2-yl)methanone

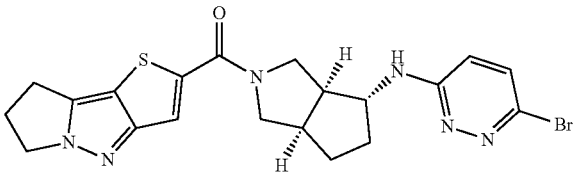 [SMILES: O=C(c1cc2nn3c(c2s1)CCC3)N1C[C@@H]2CC[C@@H](Nc3ccc(Br)nn3)[C@@H]2C1]

HPLC retention time (min): 0.92 (formic acid);
MS (ESI, Pos.): 473 (M+H)⁺;
¹H-NMR (DMSO-d₆): δ 7.63, 7.50-7.42, 7.41-7.28, 6.88-6.76, 4.32-4.21, 4.10-3.95, 3.91-3.61, 3.07-2.96, 2.96-2.77, 2.68-2.58, 2.24-2.14, 2.10-1.92, 1.69-1.55, 1.55-1.46.

Example 3-7: [(3aS,4R,6aR)-4-[(6-Bromo-3-pyridazinyl)amino]hexahydrocyclopenta[c]pyrrol-2(1H)-yl][5-methyl-4-(1-methyl-1H-pyrazol-4-yl)-2-thienyl]methanone

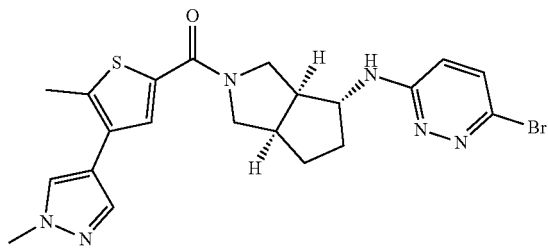 [SMILES: Cc1sc(C(=O)N2C[C@@H]3CC[C@@H](Nc4ccc(Br)nn4)[C@@H]3C2)cc1-c1cnn(C)c1]

HPLC retention time (min): 0.88 (formic acid);
MS (ESI, Pos.): 487 (M+H)+;
1H-NMR (DMSO-d6): δ 8.05-7.98, 7.78-7.70, 7.59, 7.49-7.42, 7.42-7.32, 6.87-6.76, 4.09-4.00, 3.88, 3.34-3.18, 2.94-2.75, 2.72-2.57, 2.48, 2.26-2.14, 2.09-1.95, 1.64-1.55, 1.55-1.46.

Example 3-8: [(3aS,4R,6aR)-4-[(6-Bromo-3-pyridazinyl)amino]hexahydrocyclopenta[c]pyrrol-2(1H)-yl](2,3-dimethyl-2H-thieno[2,3-c]pyrazol-5-yl)methanone

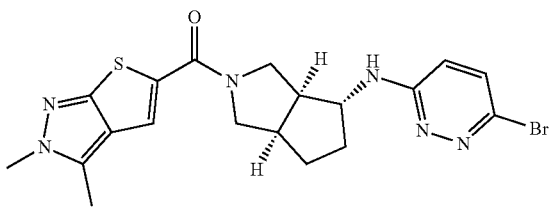 [SMILES: Cc1c2cc(C(=O)N3C[C@@H]4CC[C@@H](Nc5ccc(Br)nn5)[C@@H]4C3)sc2nn1C]

HPLC retention time (min): 0.83 (TFA);
MS (ESI, Pos.): 461 (M+H)+;
1H-NMR (CDCl3): δ 7.33-7.27, 7.26, 6.55, 4.80, 4.15-4.06, 4.02-3.93, 3.91, 3.69, 2.88, 2.70, 2.55-2.47, 2.39-2.24, 2.18-2.02, 1.69-1.61.

Example 3-9: [(3aS,4R,6aR)-4-[(6-Bromo-3-pyridazinyl)amino]hexahydrocyclopenta[c]pyrrol-2(1H)-yl](2-methyl-2H-thieno[3,2-c]pyrazol-5-yl)methanone

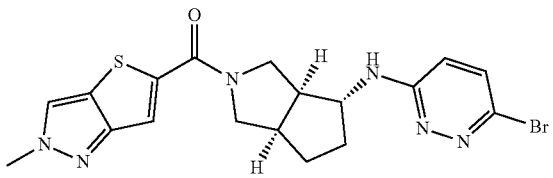 [SMILES: Cn1cc2sc(C(=O)N3C[C@@H]4CC[C@@H](Nc5ccc(Br)nn5)[C@@H]4C3)cc2n1]

HPLC retention time (min): 0.87 (TFA);
MS (ESI, Pos.): 447 (M+H)+;
1H-NMR (CDCl3): δ 7.57, 7.43, 7.33-7.27, 6.54, 4.83, 4.17-4.10, 4.10-4.02, 3.94, 3.91-3.80, 3.69, 2.92, 2.71, 2.40-2.30, 2.18-2.04, 1.70-1.61.

Example 3-10: [(3aS,4R,6aR)-4-[(6-Bromo-3-pyridazinyl)amino]hexahydrocyclopenta[c]pyrrol-2(1H)-yl](2-cyclopropyl-2H-thieno[3,2-c]pyrazol-5-yl)methanone

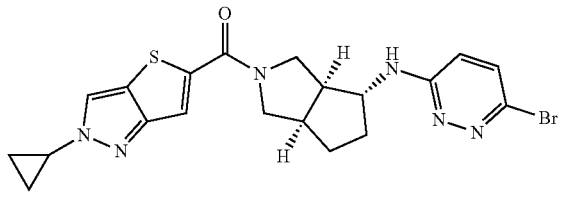 [SMILES: O=C(c1cc2nn(C3CC3)cc2s1)N1C[C@@H]2CC[C@@H](Nc3ccc(Br)nn3)[C@@H]2C1]

HPLC retention time (min): 0.86 (TFA);
MS (ESI, Pos.): 473 (M+H)+;
1H-NMR (CDCl3): δ 7.67, 7.40, 7.34-7.27, 6.55, 4.92, 4.15-3.95, 3.93, 3.90-3.78, 3.68, 2.90, 2.70, 2.39-2.28, 2.18-2.03, 1.71-1.65, 1.30-1.09.

Example 3-11: [(3aS,4R,6aR)-4-[(6-Bromo-3-pyridazinyl)amino]hexahydrocyclopenta[c]pyrrol-2(1H)-yl][2-(difluoromethyl)-2H-thieno[3,2-c]pyrazol-5-yl]methanone

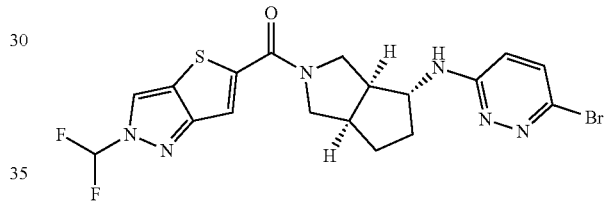

HPLC retention time (min): 0.90 (TFA);
MS (ESI, Pos.): 483 (M+H)+;
1H-NMR (CDCl3): δ 8.02, 7.48, 7.42, 7.35-7.27, 7.18, 6.71-6.49, 4.14-3.98, 3.89, 3.69, 3.05-2.83, 2.74, 2.40-2.31, 2.15, 2.05, 1.68.

Example 3-12: [(3aS,4R,6aR)-4-[(6-Bromo-3-pyridazinyl)amino]hexahydrocyclopenta[c]pyrrol-2(1H)-yl][1-(2,2,2-trifluoroethyl)-1H-thieno[3,2-c]pyrazol-5-yl]methanone

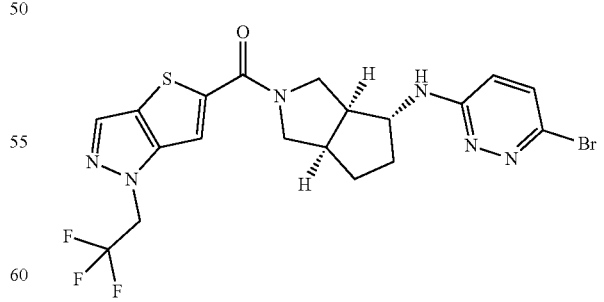

HPLC retention time (min): 1.00 (formic acid);
MS (ESI, Pos.): 515 (M+H)+;
1H-NMR (DMSO-d6): δ 7.97, 7.89-7.81, 7.52-7.43, 7.43-7.33, 6.90-6.72, 5.48-5.31, 4.19-4.05, 4.04-3.92, 3.92-3.71, 3.01-2.63, 2.27-2.15, 2.12-2.00, 1.66-1.57, 1.57-1.47.

Example 3-13: [(3aS,4R,6aR)-4-[(6-Bromo-3-pyridazinyl)amino]hexahydrocyclopenta[c]pyrrol-2(1H)-yl][2-(2,2,2-trifluoroethyl)-2H-thieno[3,2-c]pyrazol-5-yl]methanone

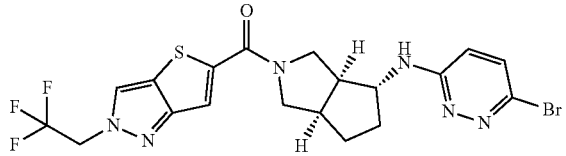 [SMILES: O=C(c1cc2nn(CC(F)(F)F)cc2s1)N1C[C@@H]2CC[C@@H](Nc3ccc(Br)nn3)[C@@H]2C1]

HPLC retention time (min): 0.90 (TFA);
MS (ESI, Pos.): 515 (M+H)$^+$;
$^1$H-NMR (CDCl$_3$): δ 7.71, 7.42, 7.26, 6.55, 4.90, 4.16-3.97, 3.94, 3.86, 3.68, 2.92, 2.72, 2.40-2.30, 2.15-2.07, 1.71-1.55.

Example 3-14: [(3aS,4R,6aR)-4-[(6-Bromo-3-pyridazinyl)amino]hexahydrocyclopenta[c]pyrrol-2(1H)-yl](2,3-dimethyl-2H-thieno[3,2-c]pyrazol-5-yl)methanone

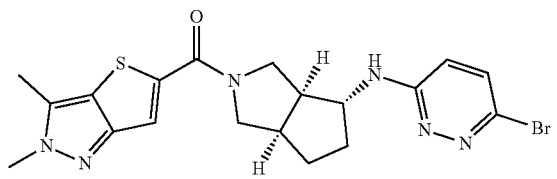 [SMILES: Cc1c2sc(C(=O)N3C[C@@H]4CC[C@@H](Nc5ccc(Br)nn5)[C@@H]4C3)cc2nn1C]

HPLC retention time (min): 0.91 (formic acid);
MS (ESI, Pos.): 461 (M+H)$^+$.

Reference Example 52: 1-(5-((3aS,4R,6aR)-4-((6-Bromopyridazin-3-yl)amino)octahydrocyclopenta[c]pyrrole-2-carbonyl)thiophen-2-yl)ethan-1-one To a solution of the compound (10 mg) prepared in Reference Example 12 in DMA (0.25 mL), were added 5-acetylthiophene-2-carboxylic acid (CAS: 4066-41-5, 6.0 mg), DIPEA (0.030 mL), and HATU (20 mg), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (15 mg).

Example 4: [(3aS,4R,6aR)-4-[(6-Bromo-3-pyridazinyl)amino]hexahydrocyclopenta[c]pyrrol-2(1H)-yl][5-(2-hydroxy-2-propanyl)-2-thienyl]methanone

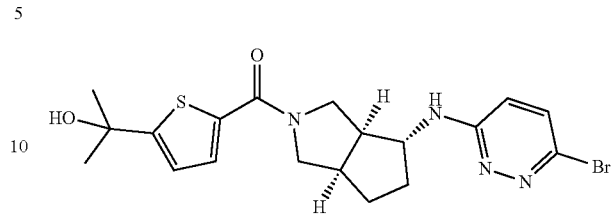

To a solution of the compound (5 mg) prepared in Reference Example 52 in THF (0.3 mL), was added 3 M methylmagnesium bromide (CAS: 75-16-1, 0.03 mL), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (1.3 mg).
HPLC retention time (min): 0.89 (formic acid);
MS (ESI, Pos.): 451 (M+H)$^+$.

Example 5: [(3aS,4R,6aR)-4-[(6-Iodo-3-pyridazinyl)amino]hexahydrocyclopenta[c]pyrrol-2(1H)-yl](5-methyl-2-thienyl)methanone

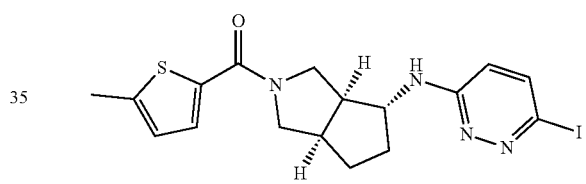

Copper(I) iodide (3.0 mg), sodium iodide (CAS: 7681-82-5, 7.4 mg), and N,N'-dimethylethylenediamine (CAS: 110-70-3, 2.8 mg) were added to a solution of the compound (10 mg) prepared in Example 2 in 1,4 dioxane (0.1 mL), and the mixture was stirred at 110° C. for 18 hours. An aqueous ammonia solution was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (7.6 mg).
HPLC retention time (min): 0.88 (TFA);
MS (ESI, Pos.): 455 (M+H)$^+$.

Example 6: rel-{(3aS,4R,6aR)-4-[(6-Bromo-3-pyridazinyl)(methyl)amino]hexahydrocyclopenta[c]pyrrol-2(1H)-yl}(5-methyl-2-thienyl)methanone racemic mixture

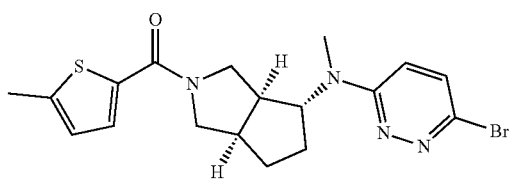

-continued and

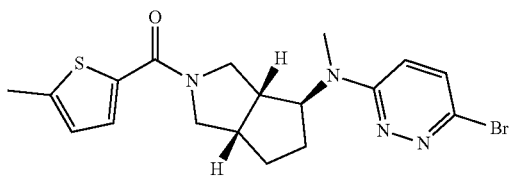

The same procedures as in Example 2→Reference Example 16 were carried out using the compound prepared in Reference Example 12-1 in place of the compound prepared in Reference Example 12 to obtain the title compound.

HPLC retention time (min): 1.10 (formic acid);

MS (ESI, Pos.): 421 (M+H)+;

$^1$H-NMR (DMSO-d$_6$): δ 7.55, 7.38, 7.19-7.10, 6.83, 4.86, 3.62, 3.27, 3.22-3.05, 2.93, 2.81, 2.49-2.43, 2.06-1.96, 1.90-1.75, 1.58-1.45.

Examples 6-1 to 6-9

The same procedures as in Example 2→Reference Example 16 were carried out using iodomethane or a corresponding halogen compound in place of iodomethane, using 5-methyl-2-thiophenecarboxylic acid or a corresponding carboxylic acid in place of 5-methyl-2-thiophenecarboxylic acid, and using the compound prepared in Reference Example 12 or the compound prepared in Reference Example 10-1 or the compound prepared in Reference Example 12-1 in place of the compound prepared in Reference Example 12 to obtain each of the title compounds.

Example 6-1: rel-{(3aS,4R,6aR)-4-[(6-Bromo-3-pyridazinyl)(butyl)amino]hexahydrocyclopenta[c]pyrrol-2(1H)-yl}(5-methyl-2-thienyl)methanone racemic mixture

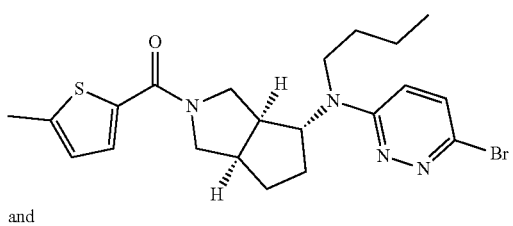

and

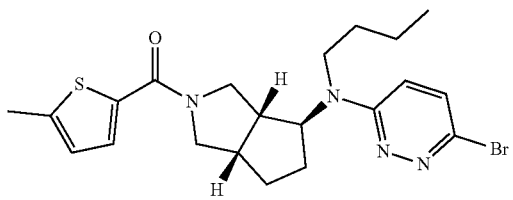

HPLC retention time (min): 1.30 (formic acid);
MS (ESI, Pos.): 463 (M+H)+;

$^1$H-NMR (DMSO-d$_6$): δ 7.51, 7.38, 7.12-7.05, 6.83, 4.66-4.58, 3.62, 3.47, 3.45-3.43, 3.35-3.25, 3.22-3.05, 2.84, 2.45, 2.06-1.91, 1.83-1.75, 1.54-1.40, 1.38-1.23, 1.18, 0.92.

Example 6-2: [(3aS,4R,6aR)-4-[Benzyl(6-bromo-3-pyridazinyl)amino]hexahydrocyclopenta[c]pyrrol-2(1H)-yl](5-methyl-2-thienyl)methanone

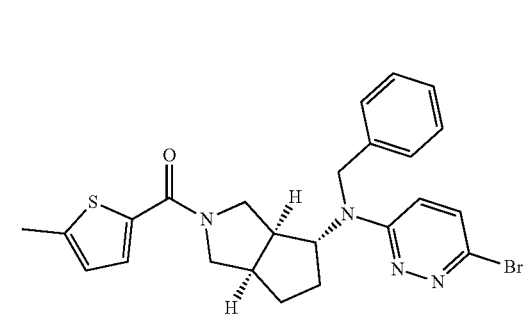 [SMILES: Cc1ccc(C(=O)N2C[C@@H]3CC[C@@H](N(Cc4ccccc4)c4ccc(Br)nn4)[C@@H]3C2)s1]

HPLC retention time (min): 1.20 (TFA);

MS (ESI, Pos.): 497 (M+H)+;

$^1$H-NMR (CDCl$_3$): δ 7.36-7.27, 7.21-7.16, 6.73, 6.48, 5.09, 4.60, 3.92-3.73, 3.62, 2.82, 2.50, 2.29-2.21, 2.14-2.03, 1.89, 1.62-1.56.

Example 6-3: [(3aS,4R,6aR)-4-[(6-Bromo-3-pyridazinyl)(methyl)amino]hexahydrocyclopenta[c]pyrrol-2(1H)-yl](6,7-dihydro-4H-thieno[3,2-c]pyran-2-yl)methanone

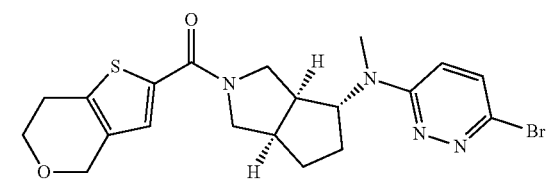 [SMILES: CN(c1ccc(Br)nn1)[C@@H]1CC[C@H]2CN(C(=O)c3cc4c(s3)CCOC4)C[C@H]21]

HPLC retention time (min): 1.00 (formic acid);

MS (ESI, Pos.): 463 (M+H)+;

$^1$H-NMR (DMSO-d$_6$): δ 7.61-7.49, 7.32, 7.21-7.06, 4.95-4.81, 4.59, 3.87, 3.82-3.56, 3.37-3.29, 3.14-3.03, 2.92, 2.09-1.93, 1.84-1.71, 1.57-1.45.

Example 6-4: rel-{(3aS,4R,6aR)-4-[(6-Chloro-3-pyridazinyl)(3-methoxypropyl)amino]hexahydrocyclopenta[c]pyrrol-2(1H)-yl}[5-(difluoromethyl)-2-thienyl]methanone racemic mixture

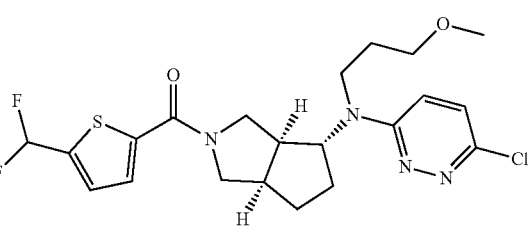

and

-continued

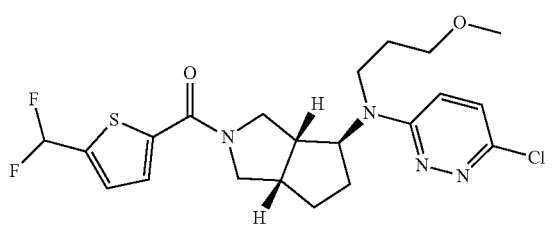

HPLC retention time (min): 1.10 (formic acid);
MS (ESI, Pos.): 471 (M+H)⁺;

$^1$H-NMR (DMSO-$d_6$): δ 7.68-7.54, 7.52-7.42, 7.43-7.21, 7.25-7.15, 4.71-4.59, 4.04-3.84, 3.64, 3.44-3.41, 3.31, 3.26, 3.24-3.15, 3.01-2.71, 2.07-1.91, 1.85-1.68, 1.58-1.44.

Example 6-5: rel-{(3aS,4R,6aR)-4-[(6-Chloro-3-pyridazinyl)(imidazo[2,1-b][1.3]thiazol-6-ylmethyl)amino]hexahydrocyclopenta[c]pyrrol-2(1H)-yl}[5-(difluoromethyl)-2-thienyl]methanone racemic mixture

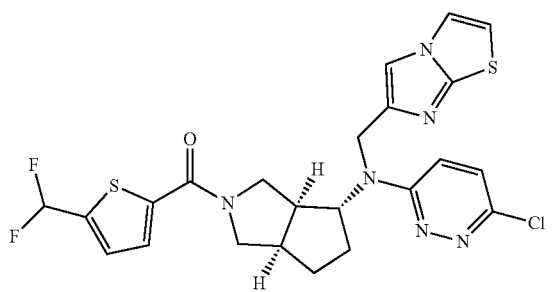

and

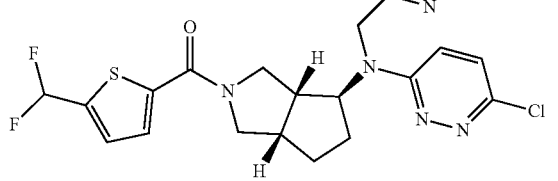

HPLC retention time (min): 0.98 (formic acid);
MS (ESI, Pos.): 535 (M+H)⁺;

$^1$H-NMR (DMSO-$d_6$): δ 7.88-7.75, 7.71-7.53, 7.53-7.17, 5.03-4.78, 4.65, 4.03-3.59, 3.15-3.05, 2.97-2.74, 2.14-1.97, 1.96-1.79, 1.58-1.43.

Example 6-6: rel-{(3aS,4R,6aR)-4-[(6-Chloro-3-pyridazinyl)(4-pyridinylmethyl)amino]hexahydrocyclopenta[c]pyrrol-2(1H)-yl}[5-(difluoromethyl)-2-thienyl]methanone racemic mixture

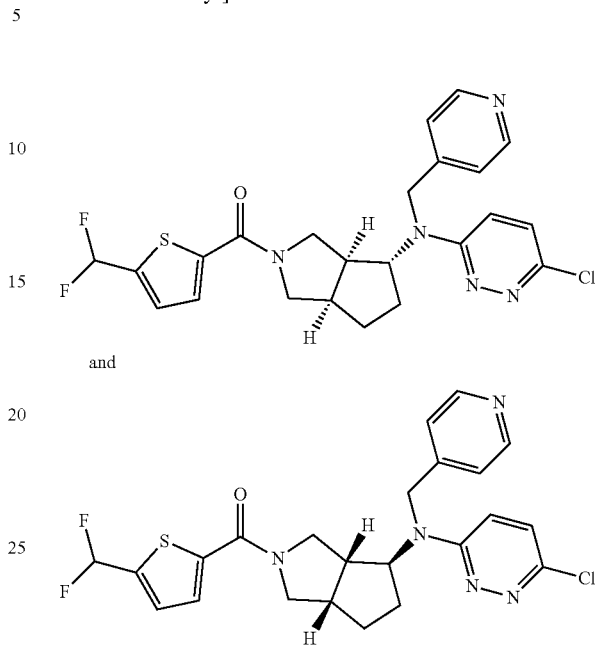

and

HPLC retention time (min): 0.88 (formic acid);
MS (ESI, Pos.): 490 (M+H)⁺;

$^1$H-NMR (DMSO-$d_6$): δ 8.61, 7.59, 7.53, 7.50-7.40, 7.24, 7.43-7.21, 4.93-4.83, 4.80, 3.95, 3.87, 3.66, 3.23-3.08, 3.00, 2.88, 2.78, 2.67, 2.55, 2.10, 1.99, 1.77-1.63, 1.62-1.45, 1.32-1.22, 1.18.

Example 6-7: rel-2-{[(6-Chloro-3-pyridazinyl)((3aS,4R,6aR)-2-{[5-(difluoromethyl)-2-thienyl]carbonyl}octahydrocyclopenta[c]pyrrol-4-yl)amino]methyl}benzonitrile racemic mixture

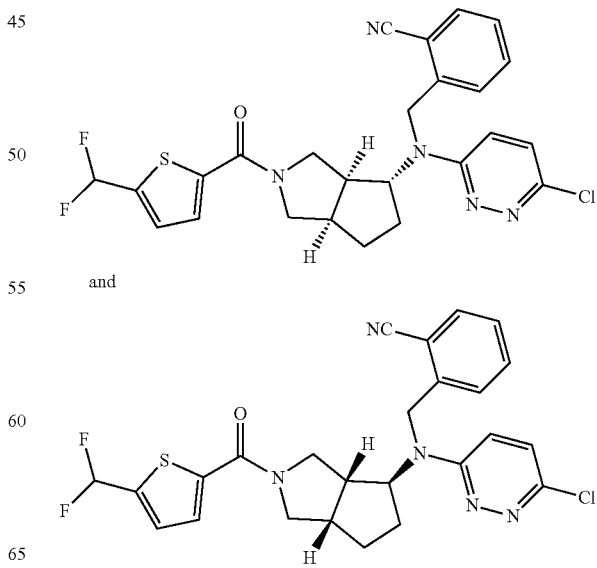

HPLC retention time (min): 1.20 (formic acid);
MS (ESI, Pos.): 514 (M+H)+;
$^1$H-NMR (DMSO-$d_6$): δ 7.91-7.84, 7.62, 7.56-7.51, 7.50-7.40, 7.43-7.22, 7.27-7.19, 4.95-4.85, 4.87-4.76, 4.02-3.87, 3.71, 3.42, 3.32-3.24, 3.14-3.05, 2.96-2.67, 2.16-2.07, 2.06-1.94, 1.57-1.38.

Example 6-8: [(3aS,4R,6aR)-4-[(6-Bromo-3-pyridazinyl)(3-fluoropropyl)amino]hexahydrocyclopenta[c]pyrrol-2(1H)-yl](5-methyl-2-thienyl)methanone

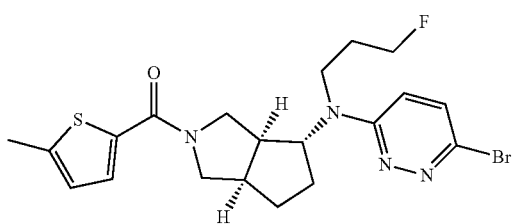 [SMILES: Cc1ccc(C(=O)N2C[C@@H]3CC[C@@H](N(CCCF)c4ccc(Br)nn4)[C@@H]3C2)s1]

HPLC retention time (min): 1.10 (TFA);
MS (ESI, Pos.): 467 (M+H)+;
$^1$H-NMR (CDCl$_3$): δ 7.32-7.28, 6.79-6.72, 4.60, 4.48, 3.82, 3.71-3.52, 2.91, 2.51, 2.20-2.02, 1.98, 1.66-1.58, 1.50, 1.33-1.19, 0.82.

Example 6-9: [(3aS,4R,6aR)-4-[(6-Bromo-3-pyridazinyl)(methyl)amino]hexahydrocyclopenta[c]pyrrol-2(1H)-yl](5-methyl-2-thienyl)methanone

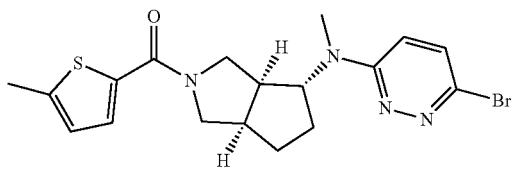 [SMILES: Cc1ccc(C(=O)N2C[C@@H]3CC[C@@H](N(C)c4ccc(Br)nn4)[C@@H]3C2)s1]

HPLC retention time (min): 0.93 (TFA);
MS (ESI, Pos.): 421 (M+H)+;
$^1$H-NMR (CDCl$_3$): δ 7.32-7.23, 6.78-6.65, 4.92-4.75, 4.01-3.85, 3.85-3.77, 3.64, 2.98, 2.92-2.77, 2.50, 2.17-2.05, 1.91-1.79, 1.61-1.52.

Reference Example 53: rel-(3aS, 6aR)-Hexahydrocyclopenta[c]pyrrol-4(1H)-one hydrochloride racemic mixture The same procedures as in Reference Example 4→Reference Example 10 were carried out using the compound prepared in Reference Example 1 in place of the compound prepared in Reference Example 3 to obtain the title compound.

Reference Example 53-1: (3aS, 6aR)-Hexahydrocyclopenta[c]pyrrol-4(1H)-one hydrochloride The same procedure as in Reference Example 10 was carried out using the compound prepared in Reference Example 3 in place of the compound prepared in Reference Example 9 to obtain the title compound.

Reference Example 54: rel-(3aS, 6aR)-2-(5-Methylthiophene-2-carbonyl)hexahydrocyclopenta[c]pyrrol-4(1H)-one racemic mixture DIPEA (22 mL) and HATU (17.6 g) were added to a solution of the compound (5.0 g) prepared in Reference Example 53 and 5-methyl-2-thiophenecarboxylic acid (6.6 g) in DMA (100 mL), and the mixture was stirred at room temperature for 3 hours. Then, 2 N hydrochloric acid was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (7.0 g).
HPLC retention time (min): 0.88 (formic acid);
MS (ESI, Pos.): 250 (M+H)+.

Reference Example 54-1: (3aS, 6aR)-2-(5-Methylthiophene-2-carbonyl)hexahydrocyclopenta[c]pyrrol-4(1H)-one The same procedure as in Reference Example 54 was carried out using the compound prepared in Reference Example 53-1 in place of the compound prepared in Reference Example 53 to obtain the title compound.

Reference Example 55: (rel-(3aS,4R,6aR)-4-(Cyclopropylamino)hexahydrocyclopenta[c]pyrrol-2(1H)-yl)(5-methylthiophen-2-yl)methanone racemic mixture Cyclopropylamine (CAS: 765-30-0, 0.25 mL) and acetic acid (0.34 mL) were added to a solution of the compound (300 mg) prepared in Reference Example 54 in dichloromethane (10 mL), and the mixture was stirred at room temperature for 10 minutes. Sodium triacetoxyborohydride (CAS: 56553-60-7, 760 mg) was added thereto, and the mixture was stirred at 40° C. for 3 hours. Then, 2 N sodium hydroxide was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (22 mg).
HPLC retention time (min): 0.78 (formic acid);
MS (ESI, Pos.): 291 (M+H)+.

Example 7: rel-{(3aS,4R,6aR)-4-[(6-Bromo-3-pyridazinyl)(cyclopropyl)amino]hexahydrocyclopenta[c]pyrrol-2(1H)-yl}(5-methyl-2-thienyl)methanone racemic mixture

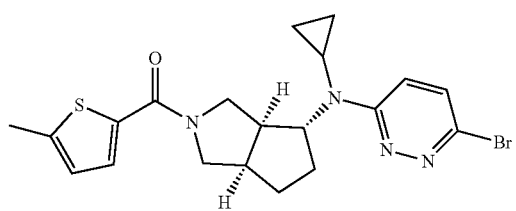

and

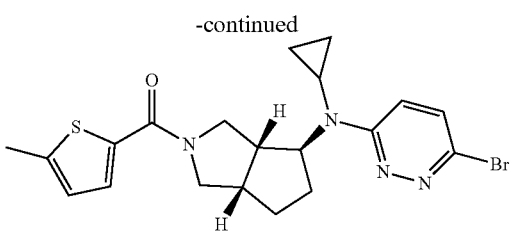

To a solution of the compound (20 mg) prepared in Reference Example 55 in tert-amyl alcohol (CAS: 75-85-4, 0.3 mL), were added 3-bromo-6-fluoropyridazine (CAS: 1353854-35-9, 39 mg) and DIPEA (0.083 mL), and the mixture was stirred at 180° C. for 1 hour in a sealed tube. The reaction solution was concentrated under reduced pressure, and then the obtained residue was purified by silica gel column chromatography to obtain the title compound (1.0 mg).

HPLC retention time (min): 1.20 (formic acid);

MS (ESI, Pos.): 447 (M+H)$^+$.

Reference Example 56: (rel-(3aS, 4S, 6aR)-4-Hydroxyhexahydrocyclopenta[c]pyrrol-2(1H)-yl)(5-methylthiophen-2-yl)methanone Racemic Mixture A 1 M lithium tri-sec-butylborohydride THF solution (8.5 mL) was added to a solution of the compound (1.4 g) prepared in Reference Example 54 in THF (42 mL) at −78° C., and the mixture was stirred at −78° C. for 1 hour. A 35% aqueous hydrogen peroxide solution was slowly added to the reaction solution at 0° C. until foaming stopped, followed by extraction with dichloromethane. The organic layer was washed with saturated saline, dried over anhydrous sodium sulfate, and concentrated under reduced pressure. The resulting residue was purified by silica gel column chromatography to obtain the title compound (600 mg).

HPLC retention time (min): 0.86 (TFA);

MS (ESI, Pos.): 252 (M+H)$^+$.

Reference Example 57: rel-(3aS, 4S, 6aR)-2-(5-Methylthiophene-2-carbonyl)octahydrocyclopenta[c]pyrrol-4-yl 4-methylbenzenesulfonate racemic mixture Triethylamine (4 mL), p-toluenesulfonyl chloride (4.1 g), and trimethylamine hydrochloride (280 mg) were added to a solution of the compound (3.6 g) prepared in Reference Example 56 in dichloromethane (70 mL), and the mixture was stirred at room temperature. A saturated aqueous sodium bicarbonate solution was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (3.6 g).

HPLC retention time (min): 1.16 (TFA);

MS (ESI, Pos.): 406 (M+H)$^+$.

Example 8: rel[(3aS,4R,6aR)-4-(3-Chloro-5,6-dihydro-7H-pyrrolo[2,3-c]pyridazin-7-yl)hexahydrocyclopenta[c]pyrrol-2(1H)-yl](5-methyl-2-thienyl)methanone Racemic Mixture

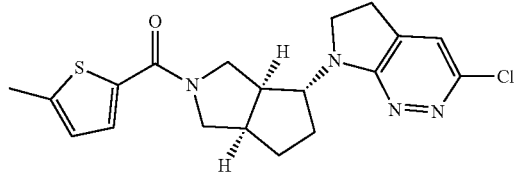

and

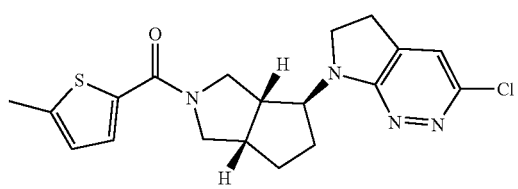

To a solution of the compound (10 mg) prepared in Reference Example 57 in THF (1 mL), were added 60% sodium hydride (3 mg) and 3-chloro-6,7-dihydro-5H-pyrrolo[2,3-c]pyridazine (CAS No.: 2089649-63-6, 7.7 mg), and the mixture was stirred at 50° C. for 20 hours. Water was added to the reaction solution, and then the resulting solution was purified by reverse phase column chromatography to obtain the title compound (1.3 mg).

HPLC retention time (min): 0.90 (formic acid);

MS (ESI, Pos.): 389 (M+H)$^+$;

$^1$H-NMR (DMSO-d$_6$): δ 7.45-7.38, 7.21-7.17, 6.88-6.80, 4.33-4.23, 3.67-3.59, 3.54-3.44, 3.08-2.99, 2.92-2.77, 2.29-2.14, 2.08-1.94, 1.94-1.76, 1.68-1.54, 1.57-1.42.

Examples 8-1 to 8-4

The same procedure as in Example 8 was carried out using a corresponding amine compound in place of 3-chloro-6,7-dihydro-5H-pyrrolo[2,3-c]pyridazine to obtain each of the title compounds.

Example 8-1: rel-[(3aS,4R,6aR)-4-(3-Chloro-7H-pyrrolo[2,3-c]pyridazin-7-yl)hexahydrocyclopenta[c]pyrrol-2(1H)-yl](5-methyl-2-thienyl)methanone racemic mixture

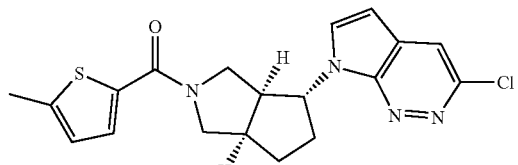

and

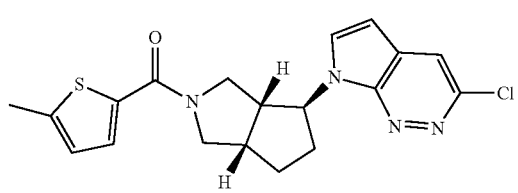

HPLC retention time (min): 1.10 (TFA);

MS (ESI, Pos.): 387 (M+H)⁺;

¹H-NMR (CDCl₃): δ 7.69, 7.55, 7.33, 6.74, 6.46, 5.14-4.96, 4.01-3.86, 3.73, 3.35-3.25, 3.13, 2.62, 2.51, 2.48-2.29, 1.80-1.65.

Example 8-2: rel-{(3aS,4R,6aR)-4-[(6-Chloro-4-methoxy-3-pyridazinyl)amino]hexahydrocyclopenta[c]pyrrol-2(1H)-yl}(5-methyl-2-thienyl)methanone Racemic Mixture

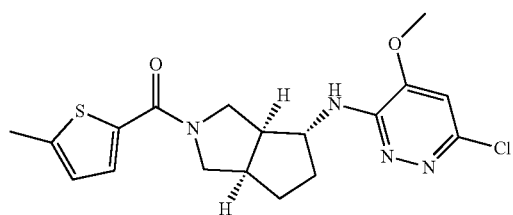

and

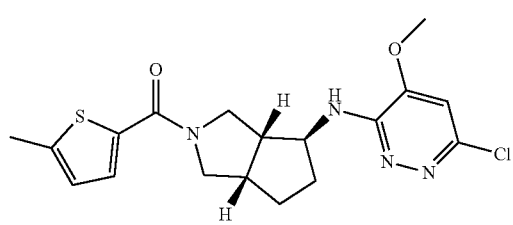

HPLC retention time (min): 0.89 (TFA);

MS (ESI, Pos.): 393 (M+H)⁺;

¹H-NMR (CDCl₃): δ 7.35-7.28, 6.76-6.70, 6.56, 4.88, 4.34-4.26, 4.15-4.02, 3.94-3.73, 3.73-3.60, 2.85, 2.74, 2.50, 2.46-2.29, 2.17-1.99, 1.70-1.60.

Example 8-3: rel-((3aS,4R,6aR)-4-((6-Chloropyridin-3-yl)amino)hexahydrocyclopenta[c]pyrrol-2(1H)-yl)(5-methylthiophen-2-yl)methanone Racemic Mixture

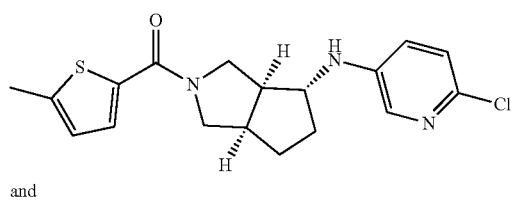

and

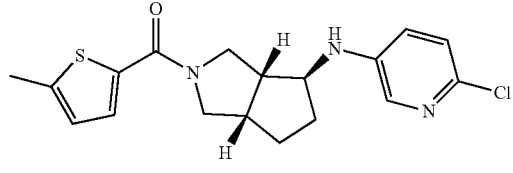

HPLC retention time (min): 1.10 (formic acid);

MS (ESI, Pos.): 362 (M+H)⁺.

Example 8-4: rel-((3aS,4R,6aR)-4-((4,6-Dichloropyridin-3-yl)amino)hexahydrocyclopenta[c]pyrrol-2(1H)-yl)(5-methylthiophen-2-yl)methanone Racemic Mixture

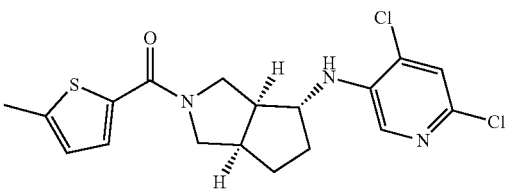

and

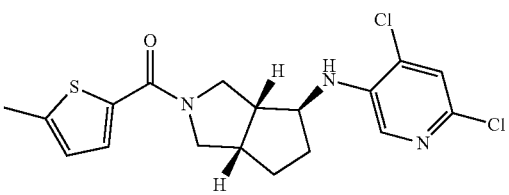

HPLC retention time (min): 1.20 (formic acid);

MS (ESI, Pos.): 396 (M+H)⁺.

Reference Example 58: rel-tert-Butyl(3aS,4R,6aR)-4-((6-chloro-4-cyanopyridazin-3-yl)amino)hexahydrocyclopenta[c]pyrrole-2(1H)-carboxylate Racemic Mixture The same procedures as in Reference Example 4→Reference Example 5→Reference Example 6→Reference Example 7→Reference Example 8→Reference Example 9 were carried out using the compound prepared in Reference Example 1 in place of the compound prepared in Reference Example 3 and using 3,6-dichloropyridazine-4-carbonitrile (CAS No.: 35857-93-3, 45 mg) in place of 3,6-dichloropyridazine to obtain the title compound.

Reference Example 59: rel-6-Chloro-3-(((3aS,4R,6aR)-octahydrocyclopenta[c]pyrrol-4-yl)amino)pyridazine-4-carbonitrile racemic mixture To the compound (100 mg) prepared in Reference Example 58, was added 4 N hydrochloric acid (1,4-dioxane solution, 3 mL), and the mixture was stirred at room temperature for 1 hour. The reaction solution was concentrated under reduced pressure to obtain the title compound (5 mg).

Example 9: rel-6-Chloro-3-({(3aS,4R,6aR)-2-[(5-methyl-2-thienyl)carbonyl]octahydrocyclopenta[c]pyrrol-4-yl}amino)-4-pyridazinecarbonitrile Racemic Mixture

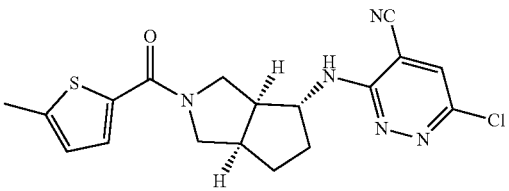

and

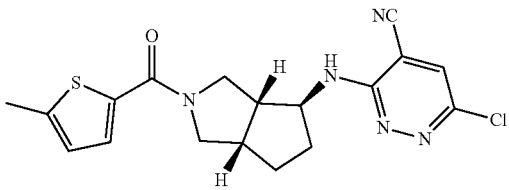

The same procedure as in Example 2 was carried out using the compound prepared in Reference Example 59 in place of the compound prepared in Reference Example 12 to obtain the title compound.
HPLC retention time (min): 1.10 (TFA);
MS (ESI, Pos.): 388 (M+H)$^+$;
$^1$H-NMR (CDCl$_3$): δ 7.42, 7.37-7.27, 6.75, 5.11, 4.47-4.39, 4.05, 3.99-3.82, 3.68, 2.91, 2.74, 2.53-2.50, 2.50-2.42, 2.21-1.98, 1.78-1.54.

Example 9-1

The same procedures as in Reference Example 9→Reference Example 10→Example 1 were carried out using a corresponding halogen compound in place of 3,6-dichloropyridazine and using a corresponding carboxylic acid in place of 5-(difluoromethyl)thiophene-2-carboxylic acid to obtain the title compound.

Example 9-1: [(3aS,4R,6aR)-4-{[6-Chloro-4-(trifluoromethyl)-3-pyridazinyl]amino}hexahydrocyclopenta[c]pyrrol-2(1H)-yl](6,7-dihydro-4H-thieno[3,2-c]pyran-2-yl)methanone

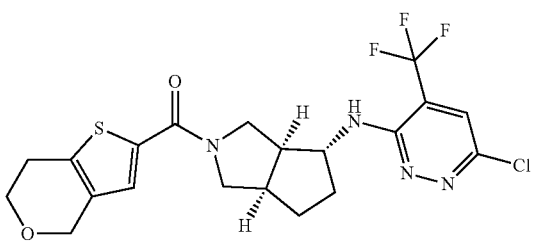 [SMILES: O=C(c1cc2c(s1)CCOC2)N1C[C@@H]2CC[C@@H](Nc3nnc(Cl)cc3C(F)(F)F)[C@@H]2C1]

HPLC retention time (min): 1.10 (formic acid);
MS (ESI, Pos.): 473 (M+H)$^+$;
$^1$H-NMR (DMSO-d$_6$): δ 7.94-7.83, 7.37-7.24, 6.85-6.70, 4.60, 4.48-4.37, 3.88, 3.82-3.63, 2.84-2.78, 2.97-2.67, 2.29-2.12, 2.10-1.98, 1.83-1.70, 1.58-1.43.

Reference Example 60: (1) [(R)-4-[tert-Butyl(dimethyl)silyl]oxy-3,5,6,6a-tetrahydro-1H-cyclopenta[c]pyrrol-2-yl]-(5-methyl-2-thienyl)methanone, and (2) [(3aR, 6aS)-6-{[dimethyl(2-methyl-2-propanyl)silyl]oxy}-3,3a,4,6a-tetrahydrocyclopenta[c]pyrrol-2(1H)-yl](5-methyl-2-thienyl)methanone Triethylamine (2.4 mL) and tert-butyldimethylsilyl trifluoromethanesulfonic acid (CAS No.: 69739-34-0, 2.0 mL) were added to a solution of the compound (4.3 g) prepared in Reference Example 54-1 in dichloromethane (86 mL), and the mixture was stirred at 40° C. for 2 hours. A saturated aqueous sodium bicarbonate solution was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (1) (1.9 g) and the title compound (2) (1.0 g).

Reference Example 61: (3aR, 6aS)-3a-Fluoro-2-(5-methylthiophene-2-carbonyl)-3,5,6,6a-tetrahydro-1H-cyclopenta[c]pyrrol-4-one To a solution of the compound (1.9 g) prepared in Reference Example 60 (1) in acetonitrile (38 mL), was added 1-chloromethyl-4-fluoro-1,4-diazoniabicyclo[2.2.2]octane bis(tetrafluoroborate) (CAS No.: 140681-55-6, 2.2 g), and the mixture was stirred at room temperature for 20 minutes. The reaction solution was concentrated under reduced pressure, and the obtained residue was purified by silica gel column chromatography to obtain the title compound (540 mg).
HPLC retention time (min): 0.95 (TFA);
MS (ESI, Pos.): 268 (M+H)$^+$.

Reference Example 62: [(3aR, 4S, 6aS)-3a-Fluoro-4-hydroxy-1,3,4,5,6,6a-hexahydrocyclopenta[c]pyrrol-2-yl]-(5-methyl-2-thienyl)methanone Sodium borohydride (CAS No.: 16940-66-2, 405 mg) was added to a solution of the compound (1.9 g) prepared in Reference Example 61 in methanol (19 mL) and THF (19 mL) at 0° C., and the mixture was stirred at 0° C. for 1 hour. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (872 mg).
HPLC retention time (min): 0.88 (TFA);
MS (ESI, Pos.): 270 (M+H)$^+$.

Reference Example 63: [(3aR,4R,6aS)-3a-Fluoro-2-(5-methylthiophene-2-carbonyl)-1.3.4.5.6.6a-hexahydro-1H-cyclopenta[c]pyrrol-4-yl]-4-methylbenzenesulfonate Triethylamine (1.4 mL), p-toluenesulfonyl chloride (1.2 g), and trimethylamine hydrochloride (154 mg) were added to a solution of the compound (872 mg) prepared in Reference Example 62 in dichloromethane (13 mL), and the mixture was stirred at room temperature for 23 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (1.0 g).
HPLC retention time (min): 1.16 (TFA);
MS (ESI, Pos.): 424 (M+H)$^+$.

Reference Example 64: [(3aR,4R,6aS)-4-Azide-3a-fluoro-1.3.4.5.6.6a-hexahydrocyclopenta[c]pyrrol-2-yl]-(5-methyl-2-thienyl)methanone Sodium azide (560 mg) was added to a solution of the compound (1.4 g) prepared in Reference Example 63 in dimethyl sulfoxide (13 mL), and the mixture was stirred at 100° C. for 90 hours. Water was added to the reaction solution, followed by extraction with dichloromethane. The organic layer was washed with saturated saline, dried over anhydrous sodium sulfate, and concentrated under reduced pressure. The obtained title compound was used for the next reaction without purification.

HPLC retention time (min): 1.08 (TFA);

MS (ESI, Pos.): 295 (M+H)$^+$.

Reference Example 65: [(3aR,4R,6aS)-4-Amino-3a-fluoro-1,3,4,5,6,6a-hexahydrocyclopenta[c]pyrrol-2-yl]-(5-methyl-2-thienyl)methanone To a solution of the compound (892 mg) prepared in Reference Example 64 in ethanol (18 mL), was added 20% palladium hydroxide (1.8 g), and the mixture was stirred at room temperature for 15 hours under a hydrogen atmosphere. The reaction solution was filtered and concentrated under reduced pressure, and the obtained title compound was used for the next reaction without purification.

HPLC retention time (min): 0.72 (TFA);

MS (ESI, Pos.): 269 (M+H)$^+$.

Example 10: [(3aR,4R,6aS)-4-[(6-Bromopyridazin-3-yl)amino]-3a-fluoro-1.3.4.5.6,6a-hexahydrocyclopenta[c]pyrrol-2-yl]-(5-methyl-2-thienyl)methanone

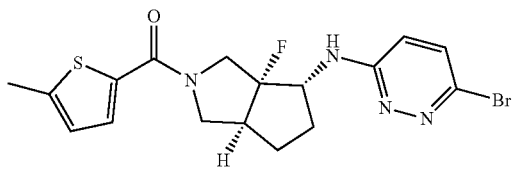 [SMILES: Cc1ccc(C(=O)N2C[C@@H]3CC[C@@H](Nc4ccc(Br)nn4)[C@]3(F)C2)s1]

DIPEA (0.91 mL) and 3-bromo-6-fluoropyridazine (619 mg) were added to a solution of the compound (470 mg) prepared in Reference Example 65 in 2-methyl-2-butanol (9.4 mL), and the mixture was stirred at 180° C. for 3 hours. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (141 mg).

HPLC retention time (min): 1.00 (TFA);

MS (ESI, Pos.): 427 (M+H)$^+$.

Reference Example 66: (3aR,4R,6aS)—N-(6-Bromo-3-pyridazinyl)-3a-fluorooctahydrocyclopenta[c]pyrrole-4-amine Methanol (1 mL) and a 5 N aqueous sodium hydroxide solution (1 mL) were added to a solution of the compound (40 mg) prepared in Example 10 in THF (2 mL), and the mixture was stirred at 50° C. for 16 hours. Water was added to the reaction solution, followed by extraction with ethyl acetate. The organic layer was washed with saturated saline, dried over anhydrous sodium sulfate, and concentrated under reduced pressure. The obtained title compound was used for the next reaction without purification.

Example 11: [(3aR,4R,6aS)-4-[(6-Bromo-3-pyridazinyl)amino]3a-fluorohexahydrocyclopenta[c]pyrrol-2(1H)-yl](6,7-dihydro-4H-thieno[3,2-c]pyran-2-yl)methanone

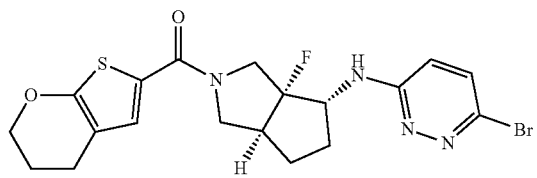 [SMILES: O=C(c1cc2c(s1)OCCC2)N1C[C@@H]2CC[C@@H](Nc3ccc(Br)nn3)[C@]2(F)C1]

DIPEA (0.02 mL) and HATU (31 mg) were added to a solution of the compound prepared in Reference Example 66 and 6,7-dihydro-4H-thieno[3,2-c]pyran-2-carboxylic acid (14 mg) in DMA (0.22 mL), and the mixture was stirred at room temperature for 3 hours. Then, 2 N hydrochloric acid was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (22 mg).

HPLC retention time (min): 0.89 (TFA);

MS (ESI, Pos.): 467 (M+H)$^+$;

$^1$H-NMR (CDCl$_3$): δ 7.29, 7.24-7.16, 6.59, 4.78, 4.75-4.67, 4.56, 4.28, 4.22-4.08, 4.01-3.89, 3.61, 2.89, 2.51-2.40, 2.26-2.17, 1.86-1.75, 1.60, 1.52-1.34.

Examples 11-1 to 11-3

The same procedure as in Example 11 was carried out using a corresponding carboxylic acid compound in place of 6,7-dihydro-4H-thieno[3,2-c]pyran-2-carboxylic acid to obtain each of the title compounds.

Example 11-1: [(3aR,4R,6aS)-4-[(6-Bromo-3-pyridazinyl)amino]-3a-fluorohexahydrocyclopenta[c]pyrrol-2(1H)-yl](2-cyclopropyl-2H-thieno[3,2-c]pyrazol-5-yl)methanone

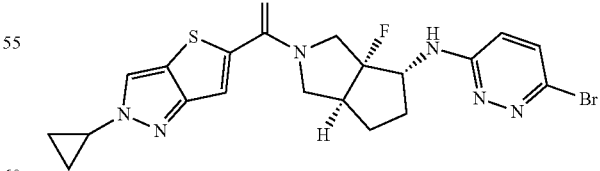

HPLC retention time (min): 0.91 (TFA);

MS (ESI, Pos.): 491 (M+H)$^+$;

$^1$H-NMR (DMSO-d$_6$): δ 8.17, 7.64, 7.47, 7.30, 6.92, 4.55-4.41, 4.00, 2.89, 2.73-2.68, 2.56-2.53, 2.29-2.16, 2.14-2.01, 1.87-1.72, 1.47-1.35, 1.28-1.12, 1.12-1.01.

Example 11-2: [(3aR,4R,6aS)-4-[(6-Bromo-3-pyridazinyl)amino]3a-fluorohexahydrocyclopenta[c]pyrrol-2(1H)-yl][5-(fluoromethyl)-2-thienyl]methanone

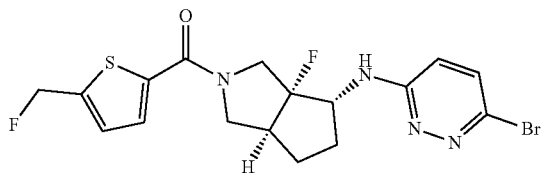 [SMILES: O=C(c1ccc(CF)s1)N1C[C@@H]2CC[C@@H](Nc3ccc(Br)nn3)[C@]2(F)C1]

HPLC retention time (min): 0.92 (TFA);
MS (ESI, Pos.): 443 (M+H)+;
1H-NMR (CDCl3): δ 7.40, 7.31, 7.28, 7.10, 6.60, 5.54, 5.42, 4.84-4.74, 4.62-4.48, 4.27-4.13, 4.01-3.93, 3.87, 3.61, 3.49, 3.00-2.83, 2.50, 2.19, 2.28-2.14, 1.61-1.58, 1.53-1.36.

Example 11-3: [(3aR,4R,6aS)-4-[(6-Bromo-3-pyridazinyl)amino]3a-fluorohexahydrocyclopenta[c]pyrrol-2(1H)-yl][5-(2-fluoroethyl)-2-thienyl]methanone

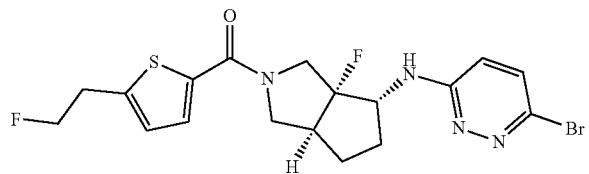 [SMILES: O=C(c1ccc(CCF)s1)N1C[C@@H]2CC[C@@H](Nc3ccc(Br)nn3)[C@]2(F)C1]

HPLC retention time (min): 0.94 (TFA);
MS (ESI, Pos.): 457 (M+H)+;
1H-NMR (CDCl3): δ 7.36-7.27, 6.87, 6.59, 4.71, 4.59, 4.19, 4.01, 3.63, 3.49, 3.28-3.17, 2.98-2.79, 2.57-2.41, 2.28-2.14, 1.87-1.73, 1.61-1.57, 1.53-1.45.

Example 12: {(3aR,4R,6aS)-4-[(6-Chloro-3-pyridazinyl)amino]-3a-fluorohexahydrocyclopenta[c]pyrrol-2(1H)-yl}(6,7-dihydro-4H-thieno[3,2-c]pyran-2-yl)methanone

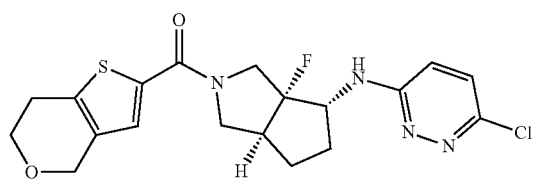 [SMILES: O=C(c1cc2c(s1)CCOC2)N1C[C@@H]2CC[C@@H](Nc3ccc(Cl)nn3)[C@]2(F)C1]

The same procedures as in Example 10→Reference Example 66→Example 11 were carried out using 3,6-dichloropyridazine in place of 3-bromo-6-fluoropyridazine and using a corresponding carboxylic acid in place of 6,7-dihydro-4H-thieno[3,2-c]pyran-2-carboxylic acid to obtain the title compound.

HPLC retention time (min): 0.89 (TFA);
MS (ESI, Pos.): 423 (M+H)+;

1H-NMR (CDCl3): δ 7.22-7.15, 6.70, 4.85, 4.71, 4.66-4.47, 4.27, 4.19-4.09, 4.03-3.90, 3.61, 2.96-2.82, 2.45, 2.27-2.15, 1.88-1.66, 1.58-1.37.

Reference Example 67: (3aS, 5R, 6aR)-5-Fluoro-2-(5-methylthiophene-2-carbonyl)-1,3,3a,5,6,6a-hexahydrocyclopenta[c]pyrrol-4-one To a solution of the compound (1.3 g) prepared in Reference Example 60(2) in acetonitrile (25 mL), was added 1-chloromethyl-4-fluoro-1,4-diazoniabicyclo[2.2.2]octane bis(tetrafluoroborate) (1.5 g), and the mixture stirred at room temperature for 3 hours. The reaction solution was concentrated under reduced pressure, water was added to the obtained residue, followed by extraction with ethyl acetate. The organic layer was washed with saturated saline, dried over anhydrous sodium sulfate, and concentrated under reduced pressure. The resulting residue was purified by silica gel column chromatography to obtain the title compound (633 mg).

HPLC retention time (min): 0.81 (TFA);
MS (ESI, Pos.): 304 (M+H)+.

Reference Example 68: [(3aS, 4R, 5R, 6aR)-5-Fluoro-4-hydroxy-3,3a,4,5,6,6a-hexahydro-1H-cyclopenta[c]pyrrol-2-yl]-(5-methyl-2-thienyl)methanone Sodium borohydride (106 mg) was added to a solution of the compound (500 mg) prepared in Reference Example 67 in methanol (10 mL) at 0° C., and the mixture was stirred at 0° C. for 1 hour. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (200 mg).

Reference Example 69: [(3aS, 4R, 5R, 6aR)-5-Fluoro-2-(5-methylthiophene-2-carbonyl)-3,3a,4,5,6,6a-hexahydro-1H-cyclopenta[c]pyrrol-4-yl]4-methylbenzenesulfonate DIPEA (0.23 mL), p-toluenesulfonyl chloride (127 mg), and trimethylamine hydrochloride (21 mg) were added to a solution of the compound (120 mg) prepared in Reference Example 68 in acetonitrile (1.2 mL), and the mixture was stirred at room temperature for 24 hours. Water was added to the reaction solution, followed by extraction with dichloromethane. After concentration, the obtained residue was purified by silica gel column chromatography to obtain the title compound (190 mg).

HPLC retention time (min): 1.13 (TFA);
MS (ESI, Pos.): 424 (M+H)+.

Reference Example 70: [(3aS, 4S, 5R, 6aR)-4-Azide-5-fluorohexahydrocyclopenta[c]pyrrol-2(1H)-yl](5-methyl-2-thienyl)methanone Sodium azide (145 mg) was added to a solution of the compound (190 mg) prepared in Reference Example 69 in dimethyl sulfoxide (0.8 mL), and the mixture was stirred at 100° C. for 17 hours. Water was added to the reaction solution, followed by extraction with ethyl acetate. The organic layer was washed with saturated saline, dried over anhydrous sodium sulfate, and concentrated under reduced pressure. The obtained title compound was used for the next reaction without purification.
HPLC retention time (min): 1.05 (TFA);
MS (ESI, Pos.): 295 (M+H)⁺.

Reference Example 71: [(3aS, 4S, 5R, 6aR)-4-Amino-5-fluoro-3,3a,4,5,6,6a-hexahydro-1H-cyclopenta[c]pyrrol-2-yl]-(5-methyl-2-thienyl)methanone To a solution of the compound prepared in Reference Example 70 in ethanol (2 mL), was added 20% palladium hydroxide (50 mg), and the mixture was stirred under a hydrogen atmosphere at room temperature for 2 hours. The reaction solution was filtered and concentrated under reduced pressure, and the obtained title compound was used for the next reaction without purification.
HPLC retention time (min): 0.75 (TFA);
MS (ESI, Pos.): 269 (M+H)⁺.

Example 13: [(3aS, 4S, 5R, 6aR)-4-[(6-Bromopyridazin-3-yl)amino]-5-fluoro-3,3a,4,5,6,6a-hexahydro-1H-cyclopenta[c]pyrrol-2-yl]-(5-methyl-2-thienyl)methanone

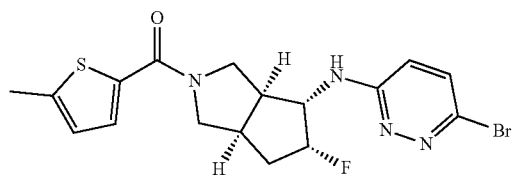 [SMILES: Cc1ccc(C(=O)N2C[C@@H]3C[C@@H](F)[C@@H](Nc4ccc(Br)nn4)[C@@H]3C2)s1]

DIPEA (0.19 mL) and 3-bromo-6-fluoropyridazine (132 mg) were added to a solution of the compound (50 mg) prepared in Reference Example 71 in 2-methyl-2-butanol (0.23 mL), and the mixture was stirred at 160° C. for 1 hour. The reaction solution was purified by reverse phase column chromatography to obtain the title compound (8.9 mg).
HPLC retention time (min): 0.94 (TFA);
MS (ESI, Pos.): 426 (M+H)⁺;
¹H-NMR (CDCl₃): δ 7.32, 7.28-7.26, 6.73, 6.62, 5.42-5.10, 4.89, 4.51-4.38, 4.13-3.88, 3.63, 3.09-2.99, 2.82-2.75, 2.50, 1.95-1.77.

Reference Example 72: (3aS, 6aR)-2-(6,7-Dihydro-4H-thieno[3,2-c]pyran-2-ylcarbonyl)hexahydrocyclopenta[c]pyrrol-4(1H)-one To a solution of the compound (2.8 g) prepared in Reference Example 53-1 in DMA (230 mL), were added 6,7-dihydro-4H-thieno[3,2-c]pyran-2-carboxylic acid (4.6 g), DIPEA (13 mL), and HATU (9.5 g), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (4.1 g).

Reference Example 73: [(3aS, 6aR)-6-{[Dimethyl (2-methyl-2-propanyl)silyl]oxy}-3,3a,4,6a-tetrahydrocyclopenta[c]pyrrol-2(1H)-yl](6,7-dihydro-4H-thieno[3,2-c]pyran-2-yl)methanone Triethylamine (2.8 mL) and tert-butyldimethylsilyl trifluoromethanesulfonate (2.3 mL) were added to a solution of the compound (2.0 g) prepared in Reference Example 72 in dichloromethane (40 mL) at 0° C., and the mixture was stirred at 50° C. for 22 hours. A saturated aqueous sodium bicarbonate solution was added to the reaction solution, followed by extraction with dichloromethane. The organic layer was washed with saturated saline, dried over anhydrous sodium sulfate, and concentrated under reduced pressure. The obtained title compound was used for the next reaction without purification.

Reference Example 74: (3aS, 5R, 6aR)-2-(6,7-Dihydro-4H-thieno[3,2-c]pyran-2-ylcarbonyl)-5-methylhexahydrocyclopenta[c]pyrrol-4(1H)-one Iodomethane (9.5 g) and 1 M tetra-N-butylammonium fluoride (CAS No. 429-41-4, 0.74 mL, THF solution) were added to a solution of the compound prepared in Reference Example 73 in DMF (10 mL), and the mixture was stirred at room temperature for 3 hours. The reaction solution was concentrated under reduced pressure, water was added to the obtained residue, followed by extraction with ethyl acetate. The organic layer was washed with saturated saline, dried over anhydrous sodium sulfate, and concentrated under reduced pressure. The resulting residue was purified by silica gel column chromatography to obtain the title compound (100 mg).

Example 14: [(3aS, 4R, 5R, 6aR)-4-[(6-Bromo-3-pyridazinyl)amino]-5-methylhexahydrocyclopenta[c]pyrrol-2(1H)-yl](6,7-dihydro-4H-thieno[3,2-c]pyran-2-yl)methanone

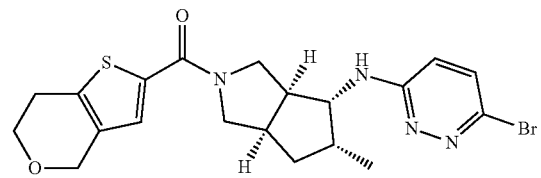 [SMILES: C[C@@H]1C[C@H]2CN(C(=O)c3cc4c(s3)CCOC4)C[C@H]2[C@@H]1Nc1ccc(Br)nn1]

The same procedures as in Reference Example 62→Reference Example 63→Reference Example 64→Reference Example 65→Example 10 were carried out using the compound prepared in Reference Example 74 in place of the compound prepared in Reference Example 61 to obtain the title compound.
HPLC retention time (min): 0.86 (TFA);
MS (ESI, Pos.): 463 (M+H)⁺;
¹H-NMR (CDCl₃): δ 7.33-7.28, 7.13, 6.65-6.58, 5.21, 4.70, 4.04-3.83, 3.66, 2.93-2.85, 2.76, 2.55, 1.88-1.69, 0.95.

Reference Example 75: (3aS, 6aR)-2-(6,7-Dihydro-4H-thieno[3,2-c]pyran-2-carbonyl)spiro[3,3a,6,6a-tetrahydro-1H-cyclopenta[c]pyrrole-5,1'-cyclopropan]-4-one To a solution of the compound (300 mg) prepared in Reference Example 72 in dimethyl sulfoxide (7.5 mL), were added 1,8-diazabicyclo[5.4.0]undec-7-ene (CAS No.: 6674-22-2, 0.31 mL) and diphenyl vinyl sulfonium triflate (CAS No.: 247129-88-0, 410 mg), and the mixture was stirred at room temperature for 1 hour. Water and a 1 N aqueous hydrochloric acid solution were added to the reaction solution, followed by extraction with ethyl acetate. The organic layer was washed with saturated saline, dried over anhydrous sodium sulfate, and concentrated under reduced pressure. The resulting residue was purified by silica gel column chromatography to obtain the title compound (100 mg).
HPLC retention time (min): 0.90 (TFA);
MS (ESI, Pos.): 318 (M+H)+.

Reference Example 76: [(3aS,4R,6aR)-4-Hydroxyspiro[1,3,3a,4,6,6a-hexahydrocyclopenta[c]pyrrole-5,1'-cyclopropan]-2-yl]-(6,7-dihydro-4H-thieno[3,2-c]pyran-2-yl)methanone Sodium borohydride (25 mg) was added to a solution of the compound (138 mg) prepared in Reference Example 75 in methanol (2.8 mL) at 0° C., and the mixture was stirred at 0° C. for 30 minutes. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (95 mg).
HPLC retention time (min): 0.91 (TFA);
MS (ESI, Pos.): 320 (M+H)+.

Reference Example 77: [(3aS, 4S, 6aR)-4-Azidospiro[1,3,3a,4,6,6a-hexahydrocyclopenta[c]pyrrole-5,1'-cyclopropan]-2-yl]-(6,7-dihydro-4H-thieno[3,2-c]pyran-2-yl)methanone Triphenylphosphine (CAS No.: 603-35-0, 102 mg), a 2.2 M diethyl azodicarboxylate solution (CAS No.: 1972-28-7, 0.18 mL), and diphenylphosphoryl azide (CAS No.: 26386-88-9, 82 mg) were added to a solution of the compound (95 mg) prepared in Reference Example 76 in THF (0.2 mL), and the mixture was stirred at room temperature for 30 minutes. The reaction solution was purified by silica gel column chromatography to obtain the title compound (43 mg).
HPLC retention time (min): 1.08 (TFA);
MS (ESI, Pos.): 345 (M+H)+.

Reference Example 78: [(3aS, 4S, 6aR)-4-Aminospiro[1,3,3a,4,6,6a-hexahydrocyclopenta[c]pyrrole-5,1'-cyclopropan]-2-yl]-(6,7-dihydro-4H-thieno[3,2-c]pyran-2-yl)methanone To a solution of the compound (43 mg) prepared in Reference Example 77 in methanol (1 mL), was added 20% palladium hydroxide (20 mg), and the mixture was stirred under a hydrogen atmosphere at room temperature for 30 minutes. The reaction solution was filtered, concentrated under reduced pressure, and purified by silica gel column chromatography to obtain the title compound (20 mg).
HPLC retention time (min): 0.73 (TFA);
MS (ESI, Pos.): 319 (M+H)+.

Example 15: [(3aS, 4S, 6aR)-4-[(6-Bromopyridazin-3-yl)amino]spiro[1,3,3a,4,6,6a-hexahydrocyclopenta[c]pyrrole-5,1'-cyclopropan]-2-yl]-(6,7-dihydro-4H-thieno[3,2-c]pyran-2-yl)methanone

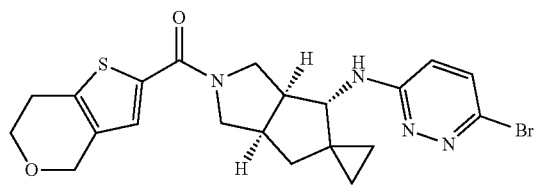 [SMILES: O=C(c1cc2c(s1)CCOC2)N1C[C@@H]2CC3(CC3)[C@@H](Nc3ccc(Br)nn3)[C@@H]2C1]

DIPEA (0.92 mL) and 3-bromo-6-fluoropyridazine (18.9 mg) were added to a solution of the compound (17 mg) prepared in Reference Example 78 in 2-methyl-2-butanol (0.5 mL), and the mixture was stirred at 180° C. for 4 hours. Water was added to the reaction solution, followed by extraction with dichloromethane. The organic layer was purified by silica gel column chromatography to obtain the title compound (13 mg).
HPLC retention time (min): 0.97 (TFA);
MS (ESI, Pos.): 477 (M+H)+;
1H-NMR (CD3OD): δ 7.37, 7.34-7.18, 6.84, 4.68, 4.12-3.91, 3.80, 2.97, 2.93-2.81, 2.36, 2.07-1.95, 1.50, 1.41-1.17, 0.74-0.65, 0.60, 0.53-0.35.

Reference Example 79: 2-Methyl-2-propanyl rel-[(3aS,4R,6aR)-2-benzyl-6-oxooctahydrocyclopenta[c]pyrrol-4-yl]carbamate racemic mixture tert-Butyl N-(4-oxocyclopenta-2-en-1-yl)carbamate (CAS No.: 657396-97-9, 17 g) and trifluoroacetic acid (58 mg) were added to a dichloromethane solution (20 mL) of N-benzyl-N-(methoxymethyl)-N-trimethylsilylmethylamine (3.6 g), and the mixture was stirred at room temperature for 16 hours. Triethylamine (430 mg) was added to the reaction solution, and the mixture was concentrated under reduced pressure. The resulting residue was purified by silica gel column chromatography to obtain the title compound (300 mg).
HPLC retention time (min): 0.86 (TFA);
MS (ESI, Pos.): 331 (M+H)+.

Reference Example 80: 2-Methyl-2-propanyl rel-[(3aS,4R,6aR)-2-benzyl-6,6-difluorooctahydrocyclopenta[c]pyrrol-4-yl]carbamate racemic mixture Bis(2-methoxyethyl)aminosulfur trifluoride (CAS No.: 202289-38-1, 1.2 g) was added to a solution of the compound (300 mg) prepared in Reference Example 79 in dichloromethane (5 mL) at 0° C., and the mixture was stirred at room temperature for 15 hours. A saturated aqueous sodium bicarbonate solution was added to the reaction solution, followed by extraction with dichloromethane. The mixture was washed with saturated saline, dried over anhydrous sodium sulfate, and concentrated under reduced pressure. The resulting residue was purified by silica gel column chromatography to obtain the title compound (120 mg).
HPLC retention time (min): 0.91 (TFA);
MS (ESI, Pos.): 353 (M+H)+.

Reference Example 81: 2-Methyl-2-propanyl rel-[(3aS,4R,6aR)-6,6-difluorooctahydrocyclopenta[c]pyrrol-4-yl]carbamate racemic mixture To a solution of the compound (120 mg) prepared in Reference Example 80 in ethanol (10 mL), was added 20% palladium hydroxide (120 mg), and the mixture was stirred under a hydrogen atmosphere at room temperature for 2 hours. The reaction solution was filtered and concentrated under reduced pressure. The obtained residue was used for the next reaction without purification.

Reference Example 82: 2-Methyl-2-propanyl rel-[(3aS,4R,6aR)-2-(6,7-dihydro-4H-thieno[3,2-c]pyran-2-ylcarbonyl)-6,6-difluorooctahydrocyclopenta[c]pyrrol-4-yl]carbamate racemic mixture To a solution of the compound prepared in Reference Example 81 in DMA (3 mL), were added 6,7-dihydro-4H- thieno[3,2-c]pyran-2-carboxylic acid (112 mg), DIPEA (0.26 mL), and HATU (210 mg), and the mixture was stirred at room temperature for 3 hours. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (100 mg).

HPLC retention time (min): 1.00 (formic acid);
MS (ESI, Pos.): 429 (M+H)$^+$.

Reference Example 83: rel-[(3aR,6R,6aS)-6-Amino-4,4-difluorohexahydrocyclopenta[c]pyrrol-2(1H)-yl](6,7-dihydro-4H-thieno[3,2-c]pyran-2-yl)methanone racemic mixture To the compound (100 mg) prepared in Reference Example 82, was added 4 N hydrochloric acid (1,4-dioxane solution, 3 mL), and the mixture was stirred at room temperature for 1 hour. The reaction solution was concentrated under reduced pressure to obtain the title compound (80 mg).

Example 16: [(3aR,6R,6aS)-6-[(6-Bromo-3-pyridazinyl)amino]-4,4-difluorohexahydrocyclopenta[c]pyrrol-2(1H)-yl](6,7-dihydro-4H-thieno[3,2-c]pyran-2-yl)methanone

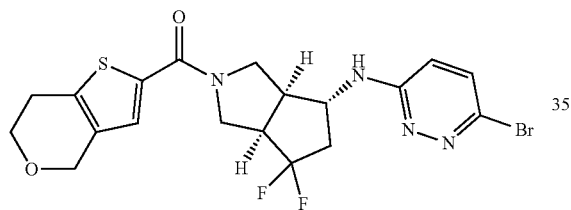

DIPEA (0.24 mL) and 3,6-dibromopyridazine (120 mg) were added to a solution of the compound (80 mg) prepared in Reference Example 83 in DMA (1 mL), and the mixture was stirred at 160° C. for 1 hour. Water was added to the reaction solution, followed by extraction with dichloromethane. The organic layer was washed with saturated saline, dried over anhydrous sodium sulfate, and concentrated under reduced pressure. The obtained residue was purified by silica gel column chromatography, and then two diastereomers were separated by supercritical fluid chromatography (CHIRALPAK IC, CO2:methanol=70:30) to obtain a low-polarity substance (19 mg).

HPLC retention time (min): 1.00 (TFA);
MS (ESI, Pos.): 485 (M+H)$^+$;
$^1$H-NMR (DMSO-d$_6$): δ 7.54-7.45, 7.36-7.35, 7.40-7.32, 6.85, 4.62, 4.23-4.15, 3.88, 3.57-3.50, 3.38-3.31, 3.31-3.16, 2.99-2.88, 2.83, 2.30-2.17.

Reference Example 84: 2-Bromo-5-[2-(2-fluoroethoxy)ethyl]thiophene

To a solution of 2-(5-bromothiophen-2-yl)ethan-1-ol (CAS No.: 57070-78-7, 653 mg) in dimethylacetamide (15 mL), were added 1-iodo-2-fluoroethane (CAS No.: 762-51-6, 1.52 mL) and sodium hydride (757 mg), and the mixture was stirred at room temperature for 17 hours. Thereafter, the mixture was stirred at 60° C. for 24 hours. Water was added to the reaction solution, followed by extraction with a mixed solvent of ethyl acetate and n-hexane. The organic layer was washed with water, dried over anhydrous sodium sulfate, and then concentrated under reduced pressure. The resulting residue was purified by silica gel column chromatography to obtain the title compound (396 mg).

HPLC retention time (min): 0.828 (TFA);
$^1$H-NMR (CDCl$_3$): δ 6.86, 6.61, 4.66-4.61, 4.54-4.49, 3.77-3.66, 3.04.

Reference Example 85: 5-[2-(2-Fluoroethoxy)ethyl]-2-thiophene carboxylic acid

Water (0.135 mL), trans-bis(acetato)bis[2-(di-O-tolylphosphino)benzyl]dipalladium(II) (CAS No.: 172418-32-5, 141 mg), DBU (0.673 mL), tri-tert-butylphosphonium tetrafluoroborate (CAS No.: 131274-22-1, 43 mg), and molybdenum hexacarbonyl (CAS No.: 13939-06-5, 595 mg) were added to a solution of the compound (396 mg) prepared in Reference Example 84 in THF (1 mL). The reaction solution was heated at 120° C. for 1 hour. A 1 M aqueous hydrochloric acid solution and ethyl acetate were added to the reaction solution, and the mixture was filtered. The organic layer was washed with water, then dried over anhydrous sodium sulfate, and concentrated under reduced pressure. The resulting residue was purified by silica gel column chromatography to obtain the title compound (190 mg).

$^1$H-NMR (CDCl$_3$): δ 7.72, 6.91, 4.72-4.61, 4.55-4.49, 3.84-3.68, 3.15, 2.50.

Reference Example 86: [(3aS,4R,6aR)-4-[(6-Bromo-3-pyridazinyl)amino]hexahydrocyclopenta[c]pyrrol-2(1H)-yl]{5-[2-(2-fluoroethoxy)ethyl]-2-thienyl}methanone DIPEA (0.024 mL) and 1H-benzotriazol-1-yloxytripyrrolidinophosphonium hexafluorophosphate (hereinafter, PyBOP, 22 mg, CAS No.: 128625-52-5) were added to a solution of the compound (10 mg) prepared in Reference Example 12 and the compound (9.2 mg) prepared in Reference Example 85 in DMF (1.0 mL), and the mixture was stirred at room temperature for 1 hour. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (5.0 mg).

HPLC retention time (min): 0.88 (TFA);
MS (ESI, Pos.): 483 (M+H)$^+$.

Example 17: [(3aS,4R,6aR)-4-[(6-Bromo-3-pyridazinyl)(methyl)amino]hexahydrocyclopenta[c]pyrrol-2(1H)-yl]{5-[2-(2-fluoroethoxy)ethyl]-2-thienyl}methanone

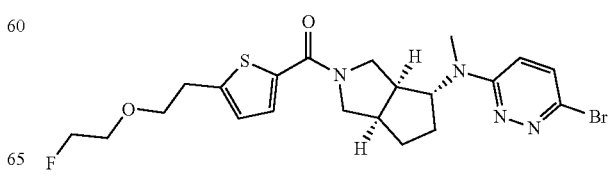

Sodium hydride (4.1 mg) was added to a solution of the compound (5.0 mg) prepared in Reference Example 86 in DMF (1.0 mL). After stirring at room temperature for 15 minutes, iodomethane (0.003 mL) was added thereto, and the mixture was further stirred at room temperature for 1 hour. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (3.9 mg).

HPLC retention time (min): 0.95 (TFA);
MS (ESI, Pos.): 497 (M+H)$^+$;
$^1$H-NMR (CDCl$_3$): δ 7.34-7.27, 6.82, 6.70, 4.84, 4.64-4.61, 4.53-4.49, 3.91, 3.83, 3.80-3.63, 3.11, 2.98, 2.92-2.77, 2.17-2.08, 1.90-1.80.

Reference Example 87:
5-(2-Fluoroethoxy)-2-thiophenecarboxylic acid

Sodium hydride (1,313 mg) was added to a solution of 2-fluoroethanol (CAS No.: 371-62-0, 1,578 mg) in DMA (15 mL) at room temperature, and then 5-fluorothiophene-2-carboxylic acid (CAS No.: 4377-58-6, 600 mg) was added thereto. The reaction solution was stirred at 100° C. for 2 days. Water was added to the reaction solution, followed by extraction with a mixed solvent of ethyl acetate and n-hexane. The organic layer was washed with water, dried over anhydrous sodium sulfate, and then concentrated under reduced pressure. The obtained residue was dissolved in methanol (4 mL), trimethylsilyldiazomethane (CAS No.: 18107-18-1, 1 mL) was added thereto, and the mixture was stirred at room temperature for 1 hour. The reaction solution was purified by silica gel column chromatography to obtain a methyl ester compound (60 mg). The methyl ester compound (60 mg) thus obtained was dissolved in methanol (4 mL), and then a 2 M aqueous sodium hydroxide solution (1.5 mL) was added thereto. The reaction solution was stirred at 50° C. for 18 hours. Then, 1 M hydrochloric acid was added to the reaction solution, followed by extraction with ethyl acetate. The organic layer was washed with water and dried over anhydrous sodium sulfate, then concentrated under reduced pressure to obtain the title compound (57 mg).

HPLC retention time (min): 0.83 (TFA);
MS (ESI, Pos.): 191 (M+H)$^+$;
$^1$H-NMR (CDCl$_3$): δ 7.53, 6.28, 4.84-4.79, 4.72-4.67, 4.38-4.27.

Reference Example 88: [(3aS,4R,6aR)-4-[(6-Bromo-3-pyridazinyl)amino]hexahydrocyclopenta[c]pyrrol-2(1H)-yl][5-(2-fluoroethoxy)-2-thienyl]methanone DIPEA (0.024 mL) and PyBOP (22 mg) were added to a solution of the compound (10 mg) prepared in Reference Example 12 and the compound (8.1 mg) prepared in Reference Example 87 in DMF (1.0 mL), and the mixture was stirred at room temperature for 1 hour. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (7.0 mg).

HPLC retention time (min): 0.89 (TFA);
MS (ESI, Pos.): 455 (M+H)$^+$.

Example 18: [(3aS,4R,6aR)-4-[(6-Bromo-3-pyridazinyl)(methyl)amino]hexahydrocyclopenta[c]pyrrol-2(1H)-yl][5-(2-fluoroethoxy)-2-thienyl]methanone

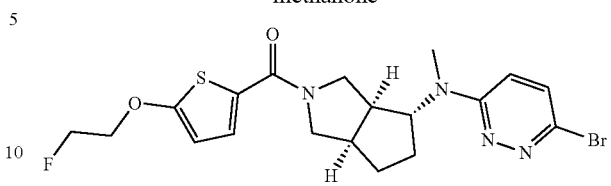

Sodium hydride (6.1 mg) was added to a solution of the compound (7.0 mg) prepared in Reference Example 88 in DMF (1.0 mL), and the mixture was stirred at room temperature for 15 minutes. Thereafter, iodomethane (0.005 mL) was added thereto, and the mixture was further stirred at room temperature for 1 hour. Water was added to the reaction solution, followed by extraction with dichloromethane. The organic layer was washed with saturated saline, dried over anhydrous sodium sulfate, and concentrated under reduced pressure. The resulting residue was purified by silica gel column chromatography to obtain the title compound (3.9 mg).

HPLC retention time (min): 0.95 (TFA);
MS (ESI, Pos.): 469 (M+H)$^+$;
$^1$H-NMR (CDCl$_3$): δ 7.28, 7.19, 6.71, 6.24, 4.91-4.78, 4.71-4.66, 4.37-4.33, 4.30-4.26, 3.95-3.78, 3.63, 2.98, 2.92-2.77, 2.17-2.09, 1.91-1.80, 1.60.

Reference Example 89: 2-{2-[(6-Bromo-3-pyridazinyl){(3aS,4R,6aR)-2-[(5-methyl-2-thienyl)carbonyl]octahydrocyclopenta[c]pyrrol-4-yl}amino]ethoxy}ethyl 4-methylbenzenesulfonate Sodium hydride (88 mg) was added to a solution of the compound (300 mg) prepared in Example 2 in DMF (7.4 mL), and the mixture was stirred at room temperature for 30 minutes. Diethylene glycol ditosylate (CAS No.: 7460-82-4, 305 mg) was then added thereto, and the mixture was stirred at room temperature for 4 hours. An aqueous sodium bicarbonate solution was added to the reaction solution, followed by extraction with dichloromethane. The organic layer was dried over anhydrous sodium sulfate and then concentrated under reduced pressure. The resulting residue was purified by silica gel column chromatography to obtain the title compound (100 mg).

HPLC retention time (min): 1.18 (TFA);
MS (ESI, Pos.): 649 (M+H)$^+$.

Example 19: [(3aS,4R,6aR)-4-{(6-Bromo-3-pyridazinyl)[2-(2-fluoroethoxy)ethyl]amino}hexahydrocyclopenta[c]pyrrol-2(1H)-yl](5-methyl-2-thienyl)methanone

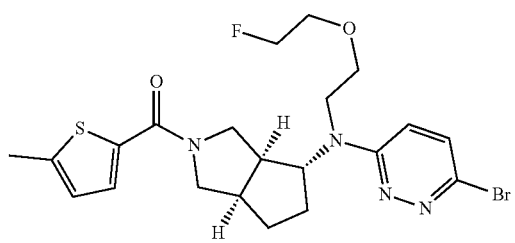 [SMILES: Cc1ccc(C(=O)N2C[C@@H]3CC[C@@H](N(CCOCCF)c4ccc(Br)nn4)[C@@H]3C2)s1]

Potassium fluoride (27 mg) and 4,7,13,16,21,24-hexaoxa-1,10-diazabicyclo[8.8.8]hexacosane (CAS No.: 23978-09-8, 174 mg) were added to a solution of the compound (100 mg) prepared in Reference Example 89 in acetonitrile (1.5 mL), and the mixture was stirred at 80° C. for 40 minutes. The reaction solution was concentrated under reduced pressure, and the obtained residue was purified by silica gel column chromatography to obtain the title compound (41.6 mg).

HPLC retention time (min): 1.05 (TFA);
MS (ESI, Pos.): 497 (M+H)$^+$;
$^1$H-NMR (CDCl$_3$): δ 7.37-7.30, 7.28-7.21, 6.85, 6.73, 4.60-4.53, 4.48-4.41, 4.32-4.23, 3.89, 3.87-3.79, 3.78-3.61, 3.04-2.83, 2.50, 2.20-2.01, 1.98-1.87.

Pharmacological Experimental Example 1:
Evaluation of ABHD6 Enzyme Inhibitory Activity First, 1-arachidonoyl glycerol (Cayman Chemical) as a substrate was prepared with an assay buffer containing 50 mM tris-HCl (pH 7.4), 100 mM NaCl, and 0.05% BSA, so as to have a final concentration of 10 μmol/L. Then, a compound was added therein so as to have a final concentration of 0.0003, 0.001, 0.003, 0.01, 0.03, 0.1, 0.3, 1, 3, or 10 μmol/L (DMSO: final concentration of 0.3%). In addition, solutions to which DMSO was added so as to have a final concentration of 0.3% were prepared as a group to which the compound was not added. The enzyme reaction was started by adding recombinant human ABHD6 (33-337) prepared with the same assay buffer to a mixed solution of the substrate and the compound so as to have a final concentration of 300 μg/mL. The recombinant human ABHD6 (33-337) was a GST-tagged ABHD6, and one which was expressed in E. coli, then purified with a Gluta-thione-Sepharose 4B resin, and then concentrated was used. The enzyme reaction was carried out at room temperature using a 384-well microplate made of polypropylene, and wells to which no enzyme was added were designated as a blank group.

One hour after the start of the enzyme reaction, methanol containing, as an internal standard substance, arachidonic acid-d8 (Cayman Chemical) and 1% formic acid was added to stop enzymatic reaction. The upper part of the enzyme reaction plate was sealed with aluminum, and centrifugation was performed at 560 g for 5 minutes at room temperature. Then, arachidonic acid as an enzyme reaction product and arachidonic acid-ds as the internal standard substance were quantified with RapidFire (registered trademark)-Mass Spectrometry system. The ratio of the quantitative values of the respective substances was taken, and the inhibition rate of arachidonic acid production at each compound concentration was calculated with the average of the blank group as 100% inhibition and the average of the group to which the compound was not added as 0% inhibition to determine the IC$_{50}$ value.

From the above pharmacological experiments, it was found that the compound of the present disclosure had potent ABHD6 inhibitory activity. For example, the IC$_{50}$ values of some compounds of the present disclosure are shown in Table 1 below.

TABLE 1

| Example No. | IC$_{50}$ (μM) |
|---|---|
| 1 | 0.001 |
| 1-2 | 0.001 |
| 1-4 | 0.001 |
| 2 | <0.001 |
| 2-1 | 0.001 |
| 2-6 | 0.002 |
| 2-14 | 0.002 |
| 3 | 0.005 |
| 3-6 | 0.002 |
| 3-9 | 0.001 |
| 3-10 | 0.001 |
| 5 | 0.001 |
| 6 | 0.002 |
| 6-2 | 0.001 |
| 8-1 | 0.001 |
| 9 | 0.002 |
| 10 | <0.001 |
| 12 | 0.001 |
| 15 | 0.001 |
| 16 | 0.001 |

Pharmacological Experimental Example 2:
Measurement of Binding Affinity for Human ABHD6

The binding affinity of the test compound for human ABHD6 was measured using bioluminescence resonance energy transfer (hereinafter, abbreviated as BRET) as an index. The bioluminescence resonance energy transfer is induced by the proximity of a probe molecule and a Nano-Luc-human ABHD6 fusion protein, which is caused by allowing a fluorescent probe molecule and a test compound to act in a competitive manner using HEK293 cells forcibly expressing the NanoLuc-human ABHD6 fusion protein.

<Compound Treatment>

The test compound and the compound described in Example 2 as a control substance were each dissolved in dimethyl sulfoxide (DMSO) to prepare a 10 mmol/L solution. The prepared 10 mmol/L solution was thawed at the time of use, serially diluted with DMSO, and subjected to an experiment.

<Cell Culture>

HEK293 cells expressing a NanoLuc-human ABHD6 fusion protein were statically cultured at 37° C. in the presence of 5% CO$_2$ using inactivated (56° C., 30 min) 9.8 vol % non-dialyzed-FBS (containing 0.5 vol % GENETI-CIN and 1% penicillin-streptomycin). The subculture was performed by the following method.

The culture medium was removed, and the cells were washed once with phosphate buffered saline without Ca$^{2+}$ and Mg$^{2+}$. An appropriate amount of trypsin-EDTA was added, and the cells were incubated at room temperature. After the cells were detached, a culture medium in a volume 10-fold the volume of trypsin-EDTA (0.05%) was added to stop an enzyme reaction. The cells were collected in a centrifuge tube, and centrifuged at room temperature for 3 minutes at 120 g, and the supernatant was removed. The cells were suspended in an appropriate amount of culture medium and seeded in a culture flask.

HEK293 cells expressing a NanoLuc-human ABHD6 fusion protein were prepared, and then cryopreserved so as to be 5.0×10$^6$ cells/mL/vial in CELLBANKER2, and the cells were subjected to an experiment. HBSS (+) containing 20 mmol/L HEPES (pH 7.3) and 0.1% BSA was prepared and used as an assay buffer. The cells were thawed and suspended in the assay buffer to prepare a cell suspension of 2×10$^5$ cells/mL. The cell suspension (25 L) was added to a 384-well assay plate to which a test compound has been added in advance, to start the reaction. The plate was allowed to stand at 37° C. for 30 minutes in the presence of 5% $CO_2$. Then, a probe molecule (10 mmol/L in DMSO) having a fluorophore was diluted with the assay buffer so as to have a final concentration of 100 nmol/L, and added to the assay plate in an amount of 15 μL each. Further, this was allowed to stand at 37° C. for 30 minutes in the presence of 5% $CO_2$. Then, a Nano-Glo (registered trademark) Vivazine (trademark) substrate (Promega Corporation) was diluted with the assay buffer according to the method described in the protocol, and added to the assay plate in an amount of 10 μL each, and this was allowed to stand at room temperature for 1 hour. Thereafter, the luminescence and fluorescence intensity were measured using a GloMax (registered trademark) discover system. The ratio between the emission intensity through the 450 nm bandpass filter and the fluorescence intensity through the 600 nm longpass filter was defined as the measured value of each sample. The measured value of the group containing the control substance at a final concentration of 30 μmol/L was defined as 100% inhibition. The measured value of the group not containing the compound was defined as 0% inhibition. The $IC_{50}$ value of the test compound was determined from the measured value at each test compound concentration.

In the cell evaluation system, it was observed that the compound of the present disclosure had potent ABHD6 binding activity. For example, the $IC_{50}$ values of some compounds of the present disclosure are shown in Table 2 below.

TABLE 2

| Example No. | $IC_{50}$ (μM) |
| --- | --- |
| 1 | 0.011 |
| 1-2 | 0.005 |
| 1-4 | 0.002 |
| 2 | 0.001 |
| 2-1 | 0.003 |
| 2-6 | 0.025 |
| 2-14 | 0.016 |
| 3 | 0.062 |
| 3-6 | 0.006 |
| 3-9 | 0.005 |
| 3-10 | 0.002 |
| 5 | 0.003 |
| 6 | 0.005 |
| 6-2 | 0.001 |
| 8-1 | 0.005 |
| 9 | 0.008 |
| 10 | 0.002 |
| 12 | 0.001 |
| 15 | 0.001 |
| 16 | 0.004 |

Pharmacological Experimental Example 3:
Evaluation of ABHD6 Selectivity

A fluorescent probe molecule and a test compound were allowed to act using a rat brain membrane fraction, followed by protein separation by electrophoresis. Then, the binding affinity of the test compound was measured using the fluorescence intensity of ABHD6, MAGL, and FAAH as an index.

<Compound Treatment>
The test compound was dissolved in dimethyl sulfoxide (DMSO) to prepare a 10 mmol/L solution. The prepared 10 mmol/L solution was thawed at the time of use, serially diluted with DMSO, and adjusted to a concentration 50 times higher than the final concentration.

<Preparation of Rat Brain Membrane Fraction>
The rat was exsanguinated under anesthesia, and then the brain thereof was extracted. Then, 1 mL of ice-cooled phosphate buffered saline (PBS, pH 7.5) was added per 200 mg of the brain, and this was homogenized by a homogenizer. The homogenate solution was centrifuged at 1,000 g and 4° C. for 10 minutes, and then the supernatant was collected. The obtained supernatant was centrifuged at 100,000 g and 4° C. for 45 minutes, ice-cold PBS was added to the sediment, and the mixture was resuspended to obtain a membrane fraction. The protein concentration in the prepared brain membrane fraction solution was quantified, and the fraction solution was stored in a freezer at −80° C. until use.

<ABPP>
The brain membrane fraction solution was prepared to 3 mg/mL with PBS. Then, 1 μL of DMSO or the compound solution was added to 50 μL of the 3 mg/mL membrane fraction solution, and this was reacted at 37° C. for 30 minutes. Thereafter, 1 μL of a probe molecule (ActivX (trade name) TAMRA-FP Serine Hydrolase Probe, final concentration: 1 μmol/L, DMSO solution) having a fluorophore was added thereto, and this was reacted at room temperature for 30 minutes. The reaction was stopped with a 4× sodium dodecyl sulfate polyacrylamide gel electrophoresis (SDS-PAGE) loading buffer. The sample was heat-treated at 95° C. for 5 minutes, and then protein separation was performed by SDS-PAGE using a 10% acrylamide gel. In the gel after SDS-PAGE, fluorescence was visualized with a chemiluminescence imaging system.

In each band of ABHD6, MAGL, and FAAH, the $IC_{50}$ value of the test compound was determined from the fluorescence intensity at each test compound concentration with the fluorescence band intensity of the control group (DMSO-treated group) as 0% inhibition. As a result, it was found that the compound of the present disclosure had selective inhibitory activity on ABHD6 against MAGL and FAAH.

Pharmacological Experimental Example 4:
Analgesic Effect on Sodium
Monoiodoacetate-Induced Model Rat The analgesic effect of the compound of the present disclosure was evaluated using a sodium monoiodoacetate (hereinafter, abbreviated as MIA) (Sigma-Aldrich Japan)-induced model rat.

(1) Preparation of MIA-Induced Model Rat
The periphery of the knee of the right hind limb of the rat was shaved under isoflurane anesthesia, and 25 μL of a 120 mg/mL MIA solution was administered into the joint space of the right hind limb using a glass syringe with a 29 G injection needle (BD Roads, Becton, Dickinson and Company, Japan). The normal control group received 25 μL of physiological saline.

(2) Group Configuration and Grouping
Rats were divided into groups consisting of a normal control group, an onset control group, a test substance administration group, and a tramadol administration group or a morphine administration group. Except for the normal control group, the right hind limb load weight ratio (measurement method will be described later) of the MIA-induced 13 or 14 days later model rat prepared by the method of (1) above was measured, and the rats were divided into groups so that the right hind limb load weight ratio was not biased in each group.

(3) Administration of Test Substance, Tramadol, or Morphine

The compound of the present disclosure as a test substance was dissolved in a solubilizing medium (7:3 solution of Kolliphor: PEG) to prepare a 0.4 or 8 mg/mL solution. The prepared solution was diluted four times with distilled water to prepare a 0.1 or 2 mg/mL solution (final concentration of solubilizing medium: 25%). Tramadol as a positive control drug was dissolved in physiological saline to prepare a 2 mg/mL solution. Alternatively, morphine as a positive control drug was dissolved in physiological saline to prepare a 0.6 mg/mL solution. The test substance was orally administered at 5 mL/kg 5 hours before the evaluation, and tramadol and morphine were subcutaneously administered at 5 mL/kg 1 hour before the evaluation.

(4) Measurement of Right Hind Limb Load Weight Ratio

The load weights of the left and right hind limbs were measured using a Linton Incapacitance Tester (MJS Technology INC., UK). Specifically, the rat was transferred to a dedicated cage on the Linton Incapacitance Tester, and the posture of the rat was adjusted so that the left and right hind limbs thereof separately ride on two pairs of weight measuring sensors. After confirming that the posture of the rat was not biased left and right and front and back, the load weight of each of the left and right hind limbs was measured for 3 seconds. The measurement of the load weight was repeated three times per individual rat. In order to obtain a stable measured value, the rat was placed in a dedicated cage for 5 days or more and acclimated for 20 minutes or more between the day of MIA induction and 14 days after induction. Furthermore, the rat was also acclimated for about 10 minutes immediately before the load weight measurement to measure the load weight. The load weights of left and right hind limbs before grouping 14 days after MIA induction, and the normal control group, the onset control group, the test substance administration group (5 hours after administration), the tramadol administration group (1 hour after administration), and the morphine administration group (1 hour after administration) after 14 days were measured. The load weight ratio of the right hind limb in the load weight of both hind limbs was calculated based on the average of load weights of left and right hind limbs, from the following Formula 1. The improvement rate of the right hind limb load weight ratio at the time of administration of the compound of the present disclosure as a test substance was calculated based on the right hind limb load weight ratio of each group 14 days after MIA induction, from the following Formula 2. Then, the analgesic effect of the test substance (compound of the present disclosure) was evaluated.

Right hind limb load weight ratio $B$ (%)=$\{A_R/(A_R+A_L)\} \times 100$    [Mathematical Formula 1]

$A_R$: Load weight of right hind limb (average of values obtained by measuring the same individual three times)

$A_L$: Load weight of left hind limb (average of values obtained by measuring the same individual three times)

Improvement rate of test substance (%)=$\{1-(B_T-B_C)/(B_N-B_C)\} \times 100$    [Mathematical Formula 2]

$B_C$: Average of right hind limb load weight ratios in normal control group $B_N$: Average of right hind limb load weight ratios in onset control group $B_T$: Average of right hind limb load weight ratios in test substance administration group As a result, it was found that the analgesic effect of the compound of the present disclosure was equivalent to or more than that of tramadol and morphine which are widely used as analgesics.

FORMULATION EXAMPLES

The following components are mixed by an ordinary method and compressed to obtain about 10,000 tablets containing 10 mg of the active ingredient in one tablet.

{(3aS,4R,6aR)-4-[(6-Chloro-3-pyridazinyl)amino]hexahydrocyclopenta[c]pyrrol-2(1H)-yl}[5-(difluoromethyl)-2-thienyl]methanone . . . 100 g
Carboxymethylcellulose calcium (disintegrant) . . . 20 g
Magnesium stearate (lubricant) . . . 10 g
Microcrystalline cellulose . . . 870 g

INDUSTRIAL APPLICABILITY

The compound of the present disclosure has ABHD6 inhibitory activity, and thus a drug containing the compound of the present disclosure as an active ingredient is useful as an agent for preventing and/or treating a disease associated with ABHD6.

The invention claimed is:

1. A compound of the following formula:

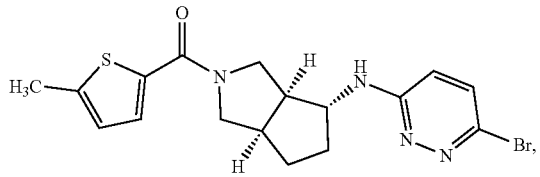 [SMILES: Cc1ccc(C(=O)N2C[C@@H]3CC[C@@H](Nc4ccc(Br)nn4)[C@@H]3C2)s1]

or a pharmaceutically acceptable salt thereof.

2. The compound of claim 1, which is [(3aS,4R,6aR)-4-[(6-bromo-3-pyridazinyl)amino]hexahydrocyclopenta[c]pyrrol-2(1H)-yl](5-methyl-2-thienyl)methanone.

3. A pharmaceutical composition containing a pharmaceutically acceptable carrier and the compound of claim 1, or a pharmaceutically acceptable salt thereof, as an active ingredient.

4. A pharmaceutical composition containing a pharmaceutically acceptable carrier and the compound of claim 2, as an active ingredient.

* * * * *